US012742210B2

(12) United States Patent
Fry et al.

(10) Patent No.: US 12,742,210 B2
(45) **Date of Patent: *Sep. 22, 2026**

(54) METHOD AND KIT FOR CHARACTERIZING MICROORGANISMS

(71) Applicant: FRY LABORATORIES, LLC, Scottsdale, AZ (US)

(72) Inventors: Stephen E. Fry, Scottsdale, AZ (US); Jeremy Ellis, Mesa, AZ (US)

(73) Assignee: Fry Laboratories, LLC, Scottsdale, AZ (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/323,688

(22) Filed: May 18, 2021

(65) Prior Publication Data

US 2021/0388419 A1 Dec. 16, 2021

Related U.S. Application Data

(63) Continuation of application No. 15/888,584, filed on Feb. 5, 2018, now abandoned, which is a continuation of application No. 14/196,999, filed on Mar. 4, 2014, now Pat. No. 9,914,979.

(60) Provisional application No. 61/772,425, filed on Mar. 4, 2013.

(51) Int. Cl.

| | |
|---|---|
| ***C12Q 1/689*** | (2018.01) |
| ***C12Q 1/6804*** | (2018.01) |
| ***C12Q 1/6869*** | (2018.01) |
| ***C12Q 1/6888*** | (2018.01) |
| ***G16B 20/00*** | (2019.01) |
| ***G16B 20/20*** | (2019.01) |
| ***G16B 30/00*** | (2019.01) |
| *C12N 15/10* | (2006.01) |

(52) U.S. Cl.
CPC .......... *C12Q 1/689* (2013.01); *C12Q 1/6804* (2013.01); *C12Q 1/6869* (2013.01); *C12Q 1/6888* (2013.01); *G16B 20/00* (2019.02); *G16B 20/20* (2019.02); *G16B 30/00* (2019.02); *C12N 15/1093* (2013.01); *C12Q 2600/16* (2013.01)

(58) Field of Classification Search
CPC .... C12Q 1/689; C12Q 1/6804; C12Q 1/6869; C12Q 1/6888; C12Q 2600/16
See application file for complete search history.

(56) References Cited

U.S. PATENT DOCUMENTS

| | | | |
|---|---|---|---|
| 4,683,195 A | 7/1987 | Mullis et al. | |
| 4,739,044 A | 4/1988 | Stabinsky | |
| 4,757,141 A | 7/1988 | Fung et al. | |
| 4,883,202 A | 11/1989 | Wahl | |
| 4,996,143 A | 2/1991 | Heller et al. | |
| 4,997,928 A | 3/1991 | Hobbs, Jr. | |
| 5,130,238 A | 7/1992 | Malek et al. | |
| 5,210,015 A | 5/1993 | Gelfand et al. | |
| 5,231,191 A | 7/1993 | Woo et al. | |
| 5,432,272 A | 7/1995 | Benner | |
| 5,436,134 A | 7/1995 | Haugland et al. | |
| 5,487,792 A | 1/1996 | King et al. | |
| 5,487,972 A | 1/1996 | Gelfand et al. | |
| 5,532,129 A | 7/1996 | Heller | |
| 5,538,848 A | 7/1996 | Livak et al. | |
| 5,565,322 A | 10/1996 | Heller | |
| 5,658,751 A | 8/1997 | Yue et al. | |
| 5,804,375 A | 9/1998 | Gelfand et al. | |
| 5,849,492 A | 12/1998 | Rogan | |
| 5,866,336 A | 2/1999 | Nazarenko et al. | |
| 5,925,517 A | 7/1999 | Tyagi et al. | |
| 5,994,056 A | 11/1999 | Higuchi | |
| 6,210,891 B1 | 4/2001 | Nyren et al. | |
| 6,214,555 B1 * | 4/2001 | Leushner | C12Q 1/703 435/6.12 |
| 6,214,979 B1 | 4/2001 | Gelfand et al. | |
| 6,258,568 B1 | 7/2001 | Nyren | |
| 6,274,320 B1 | 8/2001 | Rothberg et al. | |
| 6,775,622 B1 | 8/2004 | Holloway | |
| 7,057,026 B2 | 6/2006 | Barnes et al. | |
| 7,414,116 B2 | 8/2008 | Milton et al. | |
| 7,414,163 B1 | 8/2008 | Boldingh et al. | |
| 7,427,672 B2 | 9/2008 | Imanishi et al. | |

(Continued)

FOREIGN PATENT DOCUMENTS

| | | |
|---|---|---|
| DE | 102008019712 | 10/2009 |
| EP | 0500224 | 8/1992 |

(Continued)

OTHER PUBLICATIONS

Claesson et al. (Nucleic acids research 38.22 (2010): e200-e200; 13 pages). (Year: 2010).*

(Continued)

*Primary Examiner* — Sahana S Kaup

(74) *Attorney, Agent, or Firm* — Mughal Gaudry & Franklin PC

(57) ABSTRACT

The present disclosure provides methods of characterizing one or more microorganisms and kits for characterizing at least one microorganism. Exemplary methods include preparing an amplicon library, sequencing a characteristic gene sequence to obtain a gene sequence, and characterizing the one or more microorganisms based on the gene sequence using a computer-based genomic analysis of the gene sequence. Exemplary kits include at least one forward primer including an adapter sequence and a priming sequence, for a target sequence, and at least one reverse primer.

17 Claims, 21 Drawing Sheets

Specification includes a Sequence Listing.

(56) References Cited

U.S. PATENT DOCUMENTS

| | | | | |
|---|---|---|---|---|
| 8,241,573 | B2 | 8/2012 | Banerjee et al. | |
| 9,589,101 | B2 | 3/2017 | Fry et al. | |
| 9,914,979 | B2 | 3/2018 | Fry et al. | |
| 10,494,671 | B2 * | 12/2019 | Hendricks | C12N 9/93 |
| 2003/0096239 | A1 | 5/2003 | Gunderson et al. | |
| 2003/0099928 | A1 | 5/2003 | Burlage | |
| 2003/0119015 | A1 | 6/2003 | Frazer et al. | |
| 2005/0164219 | A1 | 7/2005 | Whitcombe et al. | |
| 2005/0233335 | A1 | 10/2005 | Wittwer et al. | |
| 2006/0019253 | A1 | 1/2006 | Wittwer et al. | |
| 2006/0211028 | A1 | 9/2006 | Mao et al. | |
| 2007/0020672 | A1 | 1/2007 | Wittwer et al. | |
| 2008/0261222 | A1 | 10/2008 | Rogan et al. | |
| 2009/0026082 | A1 | 1/2009 | Rothberg et al. | |
| 2009/0127589 | A1 | 5/2009 | Rothberg et al. | |
| 2010/0035252 | A1 | 2/2010 | Rothberg et al. | |
| 2010/0137143 | A1 | 6/2010 | Rothberg et al. | |
| 2010/0188073 | A1 | 7/2010 | Rothberg et al. | |
| 2010/0197507 | A1 | 8/2010 | Rothberg et al. | |
| 2010/0282617 | A1 | 11/2010 | Rothberg et al. | |
| 2010/0300559 | A1 | 12/2010 | Schultz et al. | |
| 2010/0300895 | A1 | 12/2010 | Nobile et al. | |
| 2010/0301398 | A1 | 12/2010 | Rothberg et al. | |
| 2010/0304982 | A1 | 12/2010 | Hinz et al. | |
| 2014/0249036 | A1 | 9/2014 | Fry et al. | |
| 2014/0249037 | A1 | 9/2014 | Fry et al. | |
| 2015/0254398 | A1 | 9/2015 | Fry et al. | |
| 2017/0293716 | A1 | 10/2017 | Fry et al. | |

FOREIGN PATENT DOCUMENTS

| | | |
|---|---|---|
| EP | 2964785 | 1/2016 |
| WO | 9106678 | 5/1991 |
| WO | 0186001 | 11/2001 |
| WO | 02063479 | 8/2002 |
| WO | 2007123744 | 11/2007 |
| WO | 2013169998 | 11/2013 |

OTHER PUBLICATIONS

Andersson et al.( PloS one 3.7 (2008); 8 pages). (Year: 2008).*
Amar et al. (Diabetologia 54.12 (2011): 3055-3061). (Year: 2011).*
Huson et al. (Genome research 17.3 (2007): 377-386.). (Year: 2007).*
Whiteley et al. ("Microbial 16S rRNA Ion Tag and community metagenome sequencing using the Ion Torrent (PGM) Platform." Journal of microbiological methods 91.1 (2012): 80-88.) (Year: 2012).*
"GS FLX Titanium Sequencing Method Manual", 2009, pp. 1-92.
"Technical Bulletin: Genome Sequencer FLX System", 2009, pp. 1-11.
U.S. Appl. No. 14/196,999 , Advisory Action, Mailed on Apr. 4, 2017, 3 pages.
U.S. Appl. No. 14/196,999 , Advisory Action, Mailed on Jun. 24, 2016, 5 pages.
U.S. Appl. No. 14/196,999 , Final Office Action, Mailed on Mar. 30, 2016, 18 pages.
U.S. Appl. No. 14/196,999 , Final Office Action, Mailed on Dec. 13, 2016, 24 pages.
U.S. Appl. No. 14/196,999 , Non Final Office Action, Mailed on Jul. 20, 2016, 21 pages.
U.S. Appl. No. 14/196, 999 , Non-Final Office Action, Mailed on Nov. 4, 2015, 15 pages.
U.S. Appl. No. 14/196,999 , Non-Final Office Action, Mailed on Jun. 16, 2017, 20 pages.
U.S. Appl. No. 14/196,999 , "Notice of Allowability", Nov. 13, 2017, 2 pages.
U.S. Appl. No. 14/196,999 , Notice of Allowance, Mailed on Oct. 20, 2017, 5 pages.
U.S. Appl. No. 14/196,999 , "Restriction Requirement", Jun. 24, 2015, 8 pages.
U.S. Appl. No. 14/197,014 , Advisory Action, Mailed on Apr. 11, 2016, 3 pages.
U.S. Appl. No. 14/197,014 , Final Office Action, Mailed on Jan. 20, 2016, 17 pages.
U.S. Appl. No. 14/197,014 , Non-Final Office Action, Mailed on Aug. 25, 2015, 17 pages.
U.S. Appl. No. 14/197,014 , Non-Final Office Action, Mailed on Sep. 23, 2016, 49 pages.
U.S. Appl. No. 14/197,014 , "Restriction Requirement", Jun. 1, 2015, 6 pages.
U.S. Appl. No. 14/197,027 , Final Office Action, Mailed on May 24, 2016, 18 pages.
U.S. Appl. No. 14/197,027 , Non-Final Office Action, Mailed on Jan. 29, 2016, 12 pages.
U.S. Appl. No. 14/197,027 , Notice of Allowance, Mailed on Nov. 23, 2016, 19 pages.
U.S. Appl. No. 15/411,350 , First Action Interview Pilot Program Pre-Interview Communication, Mailed on Mar. 21, 2017, 4 pages.
U.S. Appl. No. 15/411,350 , Notice of Allowance, Mailed on May 10, 2017, 7 pages.
U.S. Appl. No. 15/630,072 , First Action Interview Pilot Program Pre-Interview Communication, Mailed on Dec. 7, 2017, 5 pages.
U.S. Appl. No. 15/888,584 , Final Office Action, Mailed on Nov. 24, 2020, 27 pages.
U.S. Appl. No. 15/888,584 , Non-Final Office Action, Mailed on Apr. 15, 2020, 24 pages.
Amar et al., "Involvement of Tissue Bacteria in the Onset of Diabetes in Humans: Evidence for a Concept", Diabetologia, vol. 54, No. 12, Dec. 2011, pp. 3055-3061.
Andersson et al., "Comparative Analysis of Human Gut Microbiota by Barcoded Pyrosequencing", Plos One, vol. 3, No. 7, e2836, Jul. 30, 2008, pp. 1-8.
Austin et al., "Microbiologic Response to Treatment of Bacterial Vaginosis with Topical Clindamycin or Metronidazole", J. Clin. Microbiol., vol. 43, No. 9, Sep. 2005, pp. 4492-4497.
Baker et al., "Review and Re-analysis of Domain-Specific 16S Primers", Journal of Microbiological Methods, vol. 55, No. 3, Dec. 2003, pp. 541-555.
Bengtsson et al., "A New Minor Groove Binding Asymmetric Cyanine Reporter Dye for Real-time PCR", Nucleic Acids Research, vol. 31, No. 8, e45, Feb. 18, 2003, 5 pages.
Bernard et al., "Homogeneous Multiplex Genotyping of Hemochromatosis Mutations with Fluorescent Hybridization Probes", The American Journal of Pathology, vol. 153, No. 4, Oct. 1998, pp. 1055-1061.
Bokulich et al., "Next-Generation Sequencing Reveals Significant Bacterial Diversity of Botrytized Wine", PLoS One, vol. 7, No. 5, e36357, May 2012, pp. 1-10.
Bustin et al., "Pitfalls of Quantitative Real-Time Reverse-Transcription Polymerase Chain Reaction", Journal of Biomolecular Techniques, vol. 15, No. 3, Sep. 2004, pp. 155-166.
Bustin , "Quantification of Mrna Using Real-time Reverse Transcription PCR (RT-PCR): Trends and Problems", Endocrinology, vol. 29, No. 1, Aug. 2002, pp. 23-29.
Cardullo et al., "Detection of Nucleic Acid Hybridization by Nonradiative Fluorescence Resonance Energy Transfer", Proc. Natl. Acad. Sci., vol. 85, Dec. 1988, pp. 8790-8804.
Carroll et al., "Alterations in Composition and Diversity of the Intestinal Microbiota in Patients with Diarrhea-Predominant Irritable Bowel Syndrome", Neurogastroenterol & Motil, vol. 24, No. 6, Jun. 2012, pp. 521-e248.
Cha-Aim et al., "Fusion PCR Via Novel Overlap Sequences", Methods in Molecular Biology, vol. 852, Jan. 2012, pp. 97-110.
Chakravorty et al., "A Detailed Analysis of 16S Ribosomal RNA Gene Segments for the Diagnosis of Pathogenic Bacteria", J Microbiol Methods vol. 69, Issue 2, May 2007, pp. 330-339.
Claesson et al., "Comparative Analysis of Pyrosequencing and a Phylogenetic Microarray for Exploring Microbial Community Structures in the Human Distal Intestine", PLoS One, vol. 4, Issue 8, e6669, Aug. 2009, pp. 1-13.
Claesson et al., "Comparison of Two Next-Generation Sequencing Technologies for Resolving Highly Complex Microbiota Compo-

(56) References Cited

OTHER PUBLICATIONS sition Using Tandem Variable 16S rRNA Gene Regions", Nucleic Acids Research, vol. 38, No. 22, e200, Sep. 29, 2010, pp. 1-13.
Cushion et al., "Biofilm Formation by *Pneumocystis*", Spp. Eukaryot Cell, vol. 8, No. 2, Feb. 2009, pp. 197-206.
Dowd et al., "Bacterial Tag-encoded FLX Amplicon Pyrosequencing (bTEFAP) for Microbiome Studies: Bacterial Diversity in the Ileum of Newly Weaned *Salmonella*-Infected Pigs", Foodborne Pathogens and Disease, vol. 5, No. 4, Aug. 2008, pp. 459-472.
Ecker et al., "The Microbial Rosetta Stone Database: A Compilation of Global and Emerging Infectious Microorganisms and Bioterrorist Threat Agents", BMC Microbiology, vol. 5, No. 19, Apr. 25, 2005, 17 pages.
Application No. EP14717240.7 , Notice of Decision to Grant, Mailed on Jul. 30, 2020, 2 pages.
Application No. EP14717240.7 , Office Action, Mailed on Aug. 10, 2018, 4 pages.
Application No. EP14717240.7 , Office Action, Mailed on Sep. 22, 2017, 7 pages.
EP14717240.7 , "Summons to Attend Oral Proceedings", Sep. 3, 2019, 4 pages.
Espy et al., "Real-Time PCR in Clinical Microbiology: Applications for Routine Laboratory Testing", Clinical Microbiology Reviews, vol. 19, No. 1, Jan. 2006, pp. 165-256.
Fettweis et al., "The Vaginal Microbiome: Disease, Genetics and the Environment", Nature Precedings, Mar. 2011, pp. 1-6.
Giachetti et al., "Highly Sensitive Multiplex Assay for Detection of Human Immunodeficiency Virus Type 1 and Hepatitis C Virus RNA", Journal of Clinical Microbiology, vol. 40, No. 7, Apr. 13, 2002, pp. 2408-2419.
Giusti et al., "Synthesis and Characterization of 5'-fluorescent-Dye-Labeled Oligonucleotides", PCR Methods and Applications, vol. 2, No. 3, Feb. 1993, pp. 223-227.
Guo et al., "Enhanced Discrimination of Single Nucleotide Polymorphisms by Artificial Mismatch Hybridization", Nature Biotechnology, vol. 15, Apr. 1997, pp. 331-335.
Gupta et al., "A General Method for the Synthesis of 3'-sulfhydryl and Phosphate Group Containing Oligonucleotides", Nucleic Acids Research, vol. 19, No. 11, Jun. 11, 1991, pp. 3019-3025.
Hall-Stoodley et al., "Evolving Concepts in Biofilm Infections", Cell Microbiology, vol. 11, Mar. 30, 2009, pp. 1034-1043.
Harwich Jr. et al., "Genomic Sequence Analysis and Characterization of *Sneathia amnii* Sp. Nov", BMC Genomics, vol. 13(Suppl. 8), No. 517, Dec. 2012, pp. 1-9.
Hasman et al., "Rapid Whole-Genome Sequencing for Detection and Characterization of 1-20 Microorganisms From Clinical Samples", J. Clin. Microbiology vol. 52, No. 1, Jan. 2014, pp. 139-146.
Higuchi et al., "Kinetic PCT Analysis: Real-time Monitoring of DNA Amplification Reactions", Biotechnology, vol. 11, Jul. 21, 1993, pp. 1026-1030.
Huson et al., "Megan Analysis of Metagenomic Data", Genome Research, vol. 17, No. 3, Mar. 2007, pp. 377-386.
Ince et al., "Amyotrophic Lateral Sclerosis: Current Issues in Classification, Pathogenesis, and Molecular Pathology", Neuropathology and Applied Neurobiology, vol. 24, No. 2, Apr. 1998, pp. 104-117.
Janda et al., "16S rRNA Gene Sequencing for Bacterial Identification in the Diagnostic Laboratory: Pluses, Perils, and Pitfalls", Journal of Clinical Microbiology, vol. 45, No. 9, Sep. 2007, pp. 2761-2764.
Johnson et al., "A Third Base Pair for the Ploymerase Chain Reaction: Inserting IsoC and IsoG", Nucleic Acids Research, vol. 32, No. 6, Mar. 29, 2004, pp. 1937-1941.
Junemann et al., "Bacterial Community Shift in Treated Periodontitis Patients Revealed by Ion Torrent 16S rRNA Gene Amplicon Sequencing", PLoS One , vol. 7, No. 8, e41606, Aug. 1, 2012, 8 pages.
Knapp et al., "Diet-Related Composition of the Gut Microbiota of Lumbricus Rubellus as Revealed by a Molecular Fingerprinting Technique and Cloning", Soil Biology & Biochemistry vol. 41, No. 11, Nov. 2009, pp. 2299-2307.
Koshkin et al., "Reaction of Prostaglandin Endoperoxide Synthase with Cis, Cis-Eicosa-11, 14-Dienoic Acid", The Journal of Biological Chemistry, vol. 273, No. 11, Mar. 13, 1998, pp. 6046-6049.
Kumar et al., "Target Region Selection is a Critical Determinant of Community Fingerprints Generated by 16S Pyrosequencing", PLOS One, vol. 6, No. 6, e20956, Jun. 29, 2011, 8 pages.
Lay et al., "Real-Time Fluorescence Genotyping of Factor V Leiden During Rapid-Cycle PCR", Clinical Chemistry, vol. 43, No. 12, Dec. 1997, pp. 2262-2267.
Liu et al., "Short Pyrosequencing Reads Suffice for Accurate Microbial Community Analysis", Nucleic Acids Research, vol. 35, No. 18, e120, Sep. 18, 2007, pp. 1-10.
Luna et al., "DNA Pyrosequencing-Based Bacterial Pathogen Identification in a Pediatric Hospital Setting", Journal of Clinical Microbiology, vol. 45, No. 9, Sep. 2007, pp. 2985-2992.
Milani et al., "Assessing the Fecal Microbiota: An Optimized Ion Torrent 16S rRNA Gene-Based Analysis Protocol", PLoS One, vol. 8, Issue 7, e68739, Jul. 2013, pp. 1-12.
Moser et al., "Enzymatic Repair of an Expanded Genetic Information System", Nucleic Acids Research, vol. 31, No. 17, Sep. 1, 2003, pp. 5048-5053.
Murata et al., "Simultaneous Comparison of Three Protein Sequences", Proc Natl Acad Sci U S A., vol. 82, May 1985, pp. 3073-3077.
Nazarenko et al., "A Closed Tube Format for Amplification and Detection of DNA Based on Energy Transfer", Nucleic Acids Research, Oxford University Press, vol. 25, Issue No. 12, 1997, pp. 2516-2521.
Nazarenko et al., "Multiplex Quantitative PCR using Self-Quenched Primers Labeled with a Single Fluorophore", Nucleic Acids Research, vol. 30, No. 9, Feb. 27, 2002, 37 pages.
Nelson et al., "Bifunctional Oligonucleotide Probes Synthesized Using a Novel CPG Support are Able to Detect Single Base Pair Mutations", Nucleic Acids Research, vol. 17, No. 18, Aug. 11, 1989, pp. 7187-7194.
Nocker et al., "Discrimination Between Live and Dead Cells in Bacterial Communities From Environmental Water Samples Analyzed by 454 Pyrosequencing", International Microbiology, vol. 13, No. 2, May 29, 2010, pp. 59-65.
Nygren et al., "The Interactions Between the Fluorescent Dye Thiazole Orange and DNA", Biopolymers, vol. 46, Jan. 30, 1998, pp. 39-51.
O'Fallon et al., "The Emerging Threat of Multidrug-resistant Gram-negative Organisms in Long-term Care Facilities.", J Gerontol A Biol Sci Med Sci., vol. 64, No. 1, Jan. 2009, pp. 138-141.
Oldmeadow et al., "Model Selection in Bayesian Segmentation of Multiple DNA Alignments", Bioinformatics, vol. 27, No. 5, Mar. 1, 2011, pp. 604-610.
Oldmeadow et al., "Multiple Evolutionary Rate Classes in Animal Genome Evolution", Molecular Biology and Evolution, vol. 27, No. 4, Apr. 2010, pp. 942-953.
Park et al., "Bacterial Community Analysis During Fermentation of Ten Representative Kinds of Kimchi with Barcoded Pyrosequencing", Food Microbiology, vol. 30, No. 1, May 2012, pp. 197-204.
Application No. PCT/US2014/020408 , International Search Report and Written Opinion, Mailed on Sep. 1, 2014, 13 pages.
Application No. PCT/US2015/018533 , International Search Report and Written Opinion, Mailed on Jul. 8, 2015, 9 pages.
Petrosino et al., "Metagenomic Pyrosequencing and Microbial Identification", Clinical Chemistry, vol. 55, No. 5, May 2009, pp. 856-866.
Peyret et al., "Nearest-Neighbor Thermodynamics and NMR of DNA Sequences with Internal A* A, C*C, G*G*G, and T*T Mismatches", Biochemistry, vol. 38, Oct. 21, 1999, pp. 3468-3477.
Quail et al., "A Tale of Three Next Generation Sequencing Platforms: Comparison of Ion Torrent, Pacific Biosciences and Illumina Miseq Sequencers", BMC Genomics, vol. 13, No. 341, Jul. 24, 2012, pp. 1-13.
Salipante et al., "Rapid 16s rRNA Next-generation Sequencing of Polymicrobial Clinical Samples for Diagnosis of Complex Bacterial Infections", Plos One, vol. 8, No. 5, e65226, May 29, 2013, 13 pages.

(56) References Cited

OTHER PUBLICATIONS

Sano et al., "Immuno-PCR: Very Sensitive Antigen Detection by Means of Specific Antibody-DNA Conjugates", Science, vol. 258, No. 5079, Oct. 2, 1992, pp. 120-122.
Schmeider et al., "Fast Identification and Removal of Sequence Contamination from Genomic and Metagenomic Datasets", PLoS One , vol. 6, Issue 3, e17288, Mar. 9, 2011, 11 pages.
Sharma et al., "A General Method for the Synthesis of 3 '-sulfhydryl and Phosphate Group Containing Oligonucleotides", Nucleic Acids Research, vol. 19, No. 11, Jun. 11, 1991, pp. 3019-3025.
Smith et al., "Evaluation of the Bacterial Diversity of Pressure Ulcers Using BTEFAP Pyrosequencing", BMC Med. Genomics, vol. 3, No. 41, Sep. 21, 2010, pp. 1-12.
Sproat et al., "The Synthesis of Protected 5'-Mercapto-2',5'-Dideoxyribonucleoside-3'-O-Phosphoramidites, Uses of 5'-Mercapto-Oligodeoxyribonucleotides", Nucleic Acids Research, vol. 15, No. 12, Jun. 25, 1987, pp. 4837-4848.
Srinivasan et al., "Novel Etoposide Analogue Modulates Expression of Angiogenesis Associated microRNAs and Regulates Cell Proliferation by Targeting STAT3 in Breast Cancer.", PLoS One., vol. 10, No. 11, Nov. 9, 2015, pp. 1-22.
Steelman et al., "Pyrosequencing of 165 rRNA Genes in Fecal Samples Reveals High Diversity of Hindgut Microflora in Horses and Potential Links to Chronic Laminitis", BMC Veterinary Research, vol. 8, No. 231, Nov. 27, 2012, pp. 1-11.
Sul et al., "Bacterial Community Comparisons by Taxonomy-Supervised Analysis Independent of Sequence Alignment and Clustering", Proc. Natl. Acad. Sci., USA, vol. 108, No. 35, Aug. 30, 2011, pp. 14637-14642.
Thomas et al., "Metagenomics—a Guide from Sampling to Data Analysis", Microbial Informatics and Experimentation, vol. 2, No. 3, Feb. 3, 2012, 12 pages.
Urich et al., "Simultaneous Assessment of Soil Microbial Community Structure and Function through Analysis of the Meta-Transcriptome", PLoS One, vol. 3, No. 6, e2527, Jun. 25, 2008, pp. 1-13.
Voelkerding et al., "Next-Generation Sequencing: From Basic Research to Diagnostics", Clinical Chemistry, vol. 55, No. 4, Apr. 2009, pp. 641-658.
Wahlestedt et al., "Potent and Nontoxic Antisense Oligonucleotides Containing Locked Nucleic Acids", PNAS, vol. 97, No. 10, May 9, 2000, pp. 5633-5638.
Walker et al., "Strand Displacement Amplification—an Isothermal, In Vitro DNA Amplification Technique", Nucleic Acids Research, vol. 20, No. 7, Mar. 10, 1992, pp. 1691-1696.
Whitcombe et al., "Detection of PCR Products Using Self-Probing Amplicons and Fluorescence", Nature Biotechnology, vol. 17, May 21, 1999, pp. 804-807.
Whiteley et al., "Microbial 16s rRNA lon Tag and Community Metagenome Sequencing Using the Ion Torrent (PGM) Platform", Journal of Microbiological Methods, vol. 91, No. 1, Oct. 1, 2012, pp. 80-88.
Wilhelm et al., "Real-Time Polymerase Chain Reaction", Biotechniques, ChemBioChem, vol. 4, Nov. 2003, pp. 1120-1128.
Willi et al., "From Haemobartonella to Hemoplasrna: Molecular Methods Provide New Insights", Veterinary Microbiology, vol. 125, Jun. 26, 2007, pp. 197-209.
Wittwer et al., "The LightCyclerTM: A Microvolume Multisample Fluorimeter With Rapid Temperature Control", Biotechniques, vol. 22, No. 1, Jan. 1997, pp. 176-181.
Yergeau et al., "Next-Generation Sequencing of Microbial Communities in the Athabasca River and Its Tributaries in Relation to Oil Sands Mining Activities", Applied and Environmental Microbiology, vol. 78, No. 21, Nov. 2012, pp. 7626-7637.
Zipper et al., "Investigations on DNA Intercalation and Surface Binding by SYBR Green I, Its Structure Determination and Methodological Implications", Nucleic Acids Research, vol. 32, No. 12, Jun. 23, 2004, 10 pages.
Zuckerman et al., "Efficient Methods for Attachment of Thiol Specific Probes to the 3' Ends of Synthetic Oligodeoxyribonucleotides", Nucleic Acids Res., vol. 15, No. 13, Jul. 10, 1987, pp. 5305-5321.

* cited by examiner

| Description (E-Value) | Genus Antibiotics | Noted Resistance |
|---|---|---|
| Sphingomonas paucimobilis | Amikacin, sulbactum, and co-trimoxazole. | Ampicillin, cefotaxim, gentamycin, tetracyclin, beta-lactams, ciprofloxacin, and cotrimoxazole. |
| Acidovorax avenae | Not well characterized. | Not well characterized. |

| | | | | | |
|---|---|---|---|---|---|
| Patient: | Sample, Sample | Sample #: | 008 | Sample Type: | Dental Abcess |
| Doctor: | Sample Sample, M.D. | Birth: | 03/14/1879 | Collection Date: | 10/01/2013 |
| Gender: | Male | Prepared By: | AE | Received Date: | 10/02/2013 |

Pan-Bacterial Metagenomics

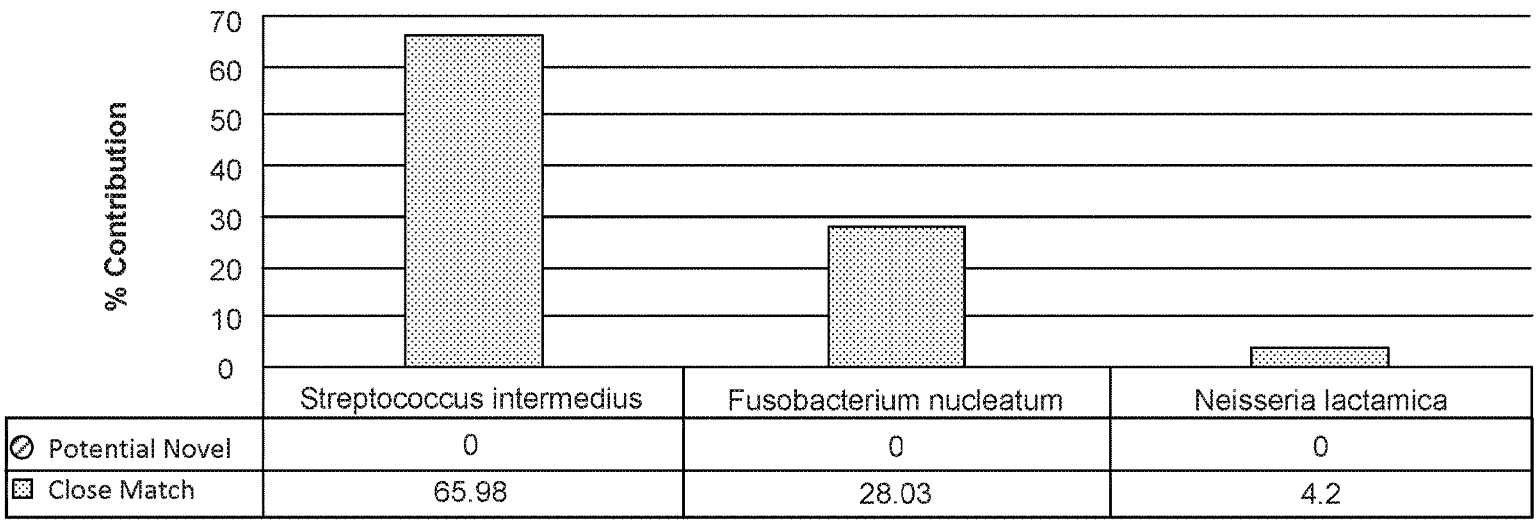

| | Streptococcus intermedius | Fusobacterium nucleatum | Neisseria lactamica |
|---|---|---|---|
| Potential Novel | 0 | 0 | 0 |
| Close Match | 65.98 | 28.03 | 4.2 |

| Description (E-Value) | Genus Antibiotics | Noted Resistance |
|---|---|---|
| Streptococcus intermedius | Penicillin, amoxicillin, intramuscular benzathine pencicillin G, erythromycin, clindamycin, cephalosporins, cephalexin,cefuroxime, axetil, and cefdinir. | Beta-lactams and macrolides. |
| Fusobacterium nucleatum | Metronidazole, piperacillin/tazobactum, ticarcillin/clavulanate, amoxicillin/sulbactum, ampicillin/sulbactum, ertupenem, imipenem, meropenem, clindamycin, and cefoxitin. | Penicillin, erythromycin and other macrolides. |
| Neisseria lactamica | Third-generation cephalosporins (cefotaxime and ceftriaxone). | Penicillin family. |

FIG. 16

Complete Significant Contribution:

| Species Name | Close Match | Potential Novel | Total Percent | Match Count | Novel Count | Total Count |
|---|---|---|---|---|---|---|
| Streptococcus intermedius | 65.98 | 0 | 65.98 | 2968 | 0 | 2968 |
| Fusobacterium nucleatum | 28.03 | 0 | 28.03 | 1261 | 0 | 1261 |
| Neisseria lactamica | 4.2 | 0 | 4.2 | 189 | 0 | 189 |

Antibiotic Susceptibility:

Neisseria species:

Active antibiotics for Neisseria include third-generation cephalosporin antibiotics such as cefotaxime and ceftriaxone. Some species have been shown to be resistant to the penicillin family of antibiotics. References: Tunkel AR, Hartman BJ, Kaplan SL, Kaufman BA, Roos KL, Scheld WM, Whitley RJ (November 2004). "Practice guidelines for the management of bacterial meningitis". Clin Infect Dis 39 (9): 1267-84. "UK doctors advised gonorrhoea has turned drug resistant BBC News. 10 October 2011.

Fusobacterium species:

Antibiotic susceptibility varies among Fusobacterium species. Treatment of Fusobacterium infections depends on the site of infections. Antibiotics used to treat Fusobacterium infections include: Metronidazole, piperacillin/tazobactum, ticarcillin/clavulanate, amoxicillin/sulbactum, ampicillin/sulbactum, ertupenem, imipenem, meropenem, clindamycin, and cefoxitin. Some resistance to penicillin noted with widespread resistance to erythromycin and other macrolides. References: Citron, D. M., Poxton, I. R., & Baron, E. J. (2007). Bacteroides, Porphyromonas, Prevotella, Fusobacterium, and Other Anaerobic Gram-Negative Rods. In P. R. Murray, E. J. Baron, M. L. Landry, J. H. Jorgensen & M. A. Pfaller (Eds.), Manual of Clinical Microbiology (9th ed., pp. 911-932). Washington, D.C.: ASM Press. Riordan, T. (2007). Human infection with Fusobacterium necrophorum (Necrobacillosis), with a focus on Lemierre's syndrome. Clinical Microbiology Reviews, 20(4), 622-659. doi:10.1128/CMR.00011-07. Boyanova, L., Kolarov, R., & Mitov, I. (2007). Antimicrobial resistance and the management of anaerobic infections. Expert Review of Anti-Infective Therapy, 5(4), 685-701.

Streptococcus species:

Active antibiotics for Streptococcus include: penicillin, amoxicillin, intramuscular benzathine pencicillin G, erythromycin, clindamycin, cephalosporins, cephalexin, cefuroxime axetil, and cefdinir. Penicillin has been reported to be ineffective in some cases. Beta-lactams and macrolides have been reported as an inactive antibiotics. References: Hooton TM. A comparison of azithromycin and penicillin V for the treatment of streptococcal pharyngitis. Am J Med. 1991 Sep 12;91(3A):23S-26S.PubMed. Cohen R, Reinert P, De La Rocque F, Levy C, Boucherat M, Robert M, Navel M, Brahimi N, Deforche D, Palestro B, Bingen E. Comparison of two dosages of azithromycin for three days versus penicillin V for ten days in acute group A streptococcal tonsillopharyngitis. Pediatr Infect Dist J. 2002 Apr;21(4):297-303. Casey JR, Pichichero ME. Meta-analysis of cephalosporin versus penicillin treatment of group A streptococcal tonsillopharyngitis in children. Pediatrics. 2004 Apr;113(4):866-82. Scholz H. Streptococcal-A tonsillopharyngitis: a 5-day course of cefuroxime axetil versus a 10-day course of penicillin V. results depending on the children's age. Chemotherapy. Baltimore RS (February 2010). "Re-evaluation of antibiotic treatment of streptococcal pharyngitis". Curr. Opin. Pediatr. 22 (1): 77-82. Shulman, ST; Bisno, AL; Clegg, HW; Gerber, MA; Kaplan, EL; Lee, G; Martin, JM; Van Beneden, C (2012 Sep 9). "Clinical Practice Guideline for the Diagnosis and Management of Group A Streptococcal Pharyngitis: 2012 Update by the Infectious Diseases Society of America.". Clinical infectious diseases : an official publication of the Infectious Diseases Society of America. Choby BA (March 2009). "Diagnosis and treatment of streptococcal pharyngitis". Am Fam Physician 79 (5): 383-90. Albrich, W; Monnet, DL; Harbarth, S (2004). "Antibiotic selection pressure and resistance in Streptococcus pneumoniae and Streptococcus pyogenes". Emerging Infect. Dis. 10 (3): 514-7. PMC 3322805. PMID 15109425.

FIG. 17

| Description (E-Value) | Genus Antibiotics | Noted Resistance |
|---|---|---|
| Babesia microti | Unknown. | Unknown. |
| Babesia species | Refer to Babesia microti. | Refer to Babesia microti. |

| Description (E-Value) | Genus Antibiotics | Noted Resistance |
|---|---|---|
| Perkinsus species | Unknown. | Unknown. |
| Perkinsus marinus | Refer to Perkinsus species. | Refer to Perkinsus species. |
| Perkinsus mediterraneus | Refer to Perkinsus species. | Refer to Perkinsus species. |

Semi-Pan-Protozoal Metagenomics

| Description (E.Value) | Genus Antibiotics | Noted Resistance |
|---|---|---|
| Toxoplasma gondii | Unknown. | Unknown. |
| Hammondia triffittae | Unknown. | Unknown. |

| Description (E-Value) | Genus Antibiotics | Noted Resistance |
|---|---|---|
| Schizosaccharomyces japonicus | Unknown. | Unknown. |
| Saccharomyces cerevisiae | Unknown. | Unknown. |
| Trichocomaceae species | Unknown. | Unknown. |

```
SEQUENCE LISTING

<160> NUMBER OF SEQ ID NOS: 74

<210> SEQ ID NO 1
<211> LENGTH: 10
<212> TYPE: DNA
<213> ORGANISM: Artificial sequence
<220> FEATURE:
<223> OTHER INFORMATION: Primer

<400> SEQUENCE: 1

ctaaggtaac                                                        10


<210> SEQ ID NO 2
<211> LENGTH: 10
<212> TYPE: DNA
<213> ORGANISM: Artificial sequence
<220> FEATURE:
<223> OTHER INFORMATION: Primer

<400> SEQUENCE: 2

taaggagaac                                                        10


<210> SEQ ID NO 3
<211> LENGTH: 10
<212> TYPE: DNA
<213> ORGANISM: Artificial sequence
<220> FEATURE:
<223> OTHER INFORMATION: Primer

<400> SEQUENCE: 3

aagaggattc                                                        10


<210> SEQ ID NO 4
<211> LENGTH: 10
<212> TYPE: DNA
<213> ORGANISM: Artificial sequence
<220> FEATURE:
<223> OTHER INFORMATION: Primer

<400> SEQUENCE: 4

taccaagatc                                                        10


<210> SEQ ID NO 5
<211> LENGTH: 10
<212> TYPE: DNA
<213> ORGANISM: Artificial sequence
<220> FEATURE:
<223> OTHER INFORMATION: Primer

<400> SEQUENCE: 5

cagaaggaac                                                        10


<210> SEQ ID NO 6
<211> LENGTH: 10
<212> TYPE: DNA
<213> ORGANISM: Artificial sequence
<220> FEATURE:
<223> OTHER INFORMATION: Primer

<400> SEQUENCE: 6
```

-continued

```
ctgcaagttc                                                            10


<210> SEQ ID NO 7
<211> LENGTH: 10
<212> TYPE: DNA
<213> ORGANISM: Artificial sequence
<220> FEATURE:
<223> OTHER INFORMATION: Primer

<400> SEQUENCE: 7

ttcgtgattc                                                            10


<210> SEQ ID NO 8
<211> LENGTH: 10
<212> TYPE: DNA
<213> ORGANISM: Artificial sequence
<220> FEATURE:
<223> OTHER INFORMATION: Primer

<400> SEQUENCE: 8

ttccgataac                                                            10


<210> SEQ ID NO 9
<211> LENGTH: 10
<212> TYPE: DNA
<213> ORGANISM: Artificial sequence
<220> FEATURE:
<223> OTHER INFORMATION: Primer

<400> SEQUENCE: 9

tgagcggaac                                                            10


<210> SEQ ID NO 10
<211> LENGTH: 10
<212> TYPE: DNA
<213> ORGANISM: Artificial sequence
<220> FEATURE:
<223> OTHER INFORMATION: Primer

<400> SEQUENCE: 10

ctgaccgaac                                                            10


<210> SEQ ID NO 11
<211> LENGTH: 10
<212> TYPE: DNA
<213> ORGANISM: Artificial sequence
<220> FEATURE:
<223> OTHER INFORMATION: Primer

<400> SEQUENCE: 11

tcctcgaatc                                                            10


<210> SEQ ID NO 12
<211> LENGTH: 10
<212> TYPE: DNA
<213> ORGANISM: Artificial sequence
<220> FEATURE:
<223> OTHER INFORMATION: Primer

<400> SEQUENCE: 12

taggtggttc                                                            10


<210> SEQ ID NO 13
<211> LENGTH: 10
<212> TYPE: DNA
<213> ORGANISM: Artificial sequence
```

```
<220> FEATURE:
<223> OTHER INFORMATION: Primer

<400> SEQUENCE: 13

tctaacggac                                                              10


<210> SEQ ID NO 14
<211> LENGTH: 10
<212> TYPE: DNA
<213> ORGANISM: Artificial sequence
<220> FEATURE:
<223> OTHER INFORMATION: Primer

<400> SEQUENCE: 14

ttggagtgtc                                                              10


<210> SEQ ID NO 15
<211> LENGTH: 10
<212> TYPE: DNA
<213> ORGANISM: Artificial sequence
<220> FEATURE:
<223> OTHER INFORMATION: Primer

<400> SEQUENCE: 15

tctagaggtc                                                              10


<210> SEQ ID NO 16
<211> LENGTH: 10
<212> TYPE: DNA
<213> ORGANISM: Artificial sequence
<220> FEATURE:
<223> OTHER INFORMATION: Primer

<400> SEQUENCE: 16

tctggatgac                                                              10


<210> SEQ ID NO 17
<211> LENGTH: 3
<212> TYPE: DNA
<213> ORGANISM: Artificial sequence
<220> FEATURE:
<223> OTHER INFORMATION: Primer

<400> SEQUENCE: 17

gat                                                                      3


<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18

agagtttgat cctggctcag                                                   20


<210> SEQ ID NO 19
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (10)..(11)
<223> OTHER INFORMATION: n = pyrimidine (t/u or c)
<220> FEATURE:
```

<221> NAME/KEY: misc_feature
<222> LOCATION: (15)..(15)
<223> OTHER INFORMATION: n = purine (g or a)

<400> SEQUENCE: 19
ccgtcaattn ntttnagttt 20

<210> SEQ ID NO 20
<211> LENGTH: 19
<212> TYPE: DNA
<213> ORGANISM: Artificial sequence
<220> FEATURE:
<223> OTHER INFORMATION: Primer

<400> SEQUENCE: 20
ggttaccttg ttacgactt 19

<210> SEQ ID NO 21
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (8)..(8)
<223> OTHER INFORMATION: n = pyrimidine (t/u or c)
<220> FEATURE:
<221> NAME/KEY: misc_feature
<222> LOCATION: (12)..(12)
<223> OTHER INFORMATION: n = keto (g or t/u)

<400> SEQUENCE: 21
taaaactnaa angaattgac ggg 23

<210> SEQ ID NO 22
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n = strong interaction 3H-bonds (g or c)
<220> FEATURE:
<221> NAME/KEY: misc_feature
<222> LOCATION: (10)..(10)
<223> OTHER INFORMATION: n = pyrimidine (t/u or c)

<400> SEQUENCE: 22
actgctgcnn cccgtaggag tct 23

<210> SEQ ID NO 23
<211> LENGTH: 15
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n = pyrimidine (t/u or c)

<400> SEQUENCE: 23
naacgagcgc aaccc 15

<210> SEQ ID NO 24
<211> LENGTH: 15

-continued

<212> TYPE: DNA
<213> ORGANISM: Artificial sequence
<220> FEATURE:
<223> OTHER INFORMATION: Primer

<400> SEQUENCE: 24
gggttgcgct cgttg 15

<210> SEQ ID NO 25
<211> LENGTH: 21
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (17)..(17)
<223> OTHER INFORMATION: n = weak interaction 2H-bonds (a or t/u)

<400> SEQUENCE: 25
gactcctacg ggaggcngca g 21

<210> SEQ ID NO 26
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n = purine (g or a)

<400> SEQUENCE: 26
ccgtcaattc ctttnagttt 20

<210> SEQ ID NO 27
<211> LENGTH: 18
<212> TYPE: DNA
<213> ORGANISM: Artificial sequence
<220> FEATURE:
<223> OTHER INFORMATION: Primer

<400> SEQUENCE: 27
ggattagata ccctggta 18

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
gactaccagg gtatctaatc 20

<210> SEQ ID NO 29
<211> LENGTH: 19
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n = amino (a or c)

<400> SEQUENCE: 29

-continued gtgccagcng ccgcggtaa 19

<210> SEQ ID NO 30
<211> LENGTH: 19
<212> TYPE: DNA
<213> ORGANISM: Artificial sequence
<220> FEATURE:
<223> OTHER INFORMATION: Primer

<400> SEQUENCE: 30
gtattaccgc ggctgctgg 19

<210> SEQ ID NO 31
<211> LENGTH: 30
<212> TYPE: DNA
<213> ORGANISM: Artificial sequence
<220> FEATURE:
<223> OTHER INFORMATION: Primer

<400> SEQUENCE: 31
ccatctcatc cctgcgtgtc tccgactcag 30

<210> SEQ ID NO 32
<211> LENGTH: 23
<212> TYPE: DNA
<213> ORGANISM: Artificial sequence
<220> FEATURE:
<223> OTHER INFORMATION: Primer

<400> SEQUENCE: 32
cctctctatg ggcagtcggt gat 23

<210> SEQ ID NO 33
<211> LENGTH: 38
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (33)..(33)
<223> OTHER INFORMATION: n = a, g, or t/u, but not c

<400> SEQUENCE: 33
cctctctatg ggcagtcggt gatctgctgc ctnccgta 38

<210> SEQ ID NO 34
<211> LENGTH: 38
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (25)..(25)
<223> OTHER INFORMATION: n = pyrimidine (t/u or c)
<220> FEATURE:
<221> NAME/KEY: misc_feature
<222> LOCATION: (30)..(30)
<223> OTHER INFORMATION: n = pyrimidine (t/u or c)
<220> FEATURE:
<221> NAME/KEY: misc_feature
<222> LOCATION: (31)..(31)
<223> OTHER INFORMATION: n = a, g, or t/u but not c
<220> FEATURE:
<221> NAME/KEY: misc_feature
<222> LOCATION: (37)..(37)
<223> OTHER INFORMATION: n = a, g, c or t/u, or unknown, or other

<400> SEQUENCE: 34

-continued cctctctatg ggcagtcggt gatantgggn ntaaagng 38

<210> SEQ ID NO 35
<211> LENGTH: 63
<212> TYPE: DNA
<213> ORGANISM: Artificial sequence
<220> FEATURE:
<223> OTHER INFORMATION: Primer

<400> SEQUENCE: 35
ccatctcatc cctgcgtgtc tccgactcag ctaaggtaac gatagagttt gatcctggct 60
cag 63

<210> SEQ ID NO 36
<211> LENGTH: 63
<212> TYPE: DNA
<213> ORGANISM: Artificial sequence
<220> FEATURE:
<223> OTHER INFORMATION: Primer

<400> SEQUENCE: 36
ccatctcatc cctgcgtgtc tccgactcag taaggagaac gatagagttt gatcctggct 60
cag 63

<210> SEQ ID NO 37
<211> LENGTH: 63
<212> TYPE: DNA
<213> ORGANISM: Artificial sequence
<220> FEATURE:
<223> OTHER INFORMATION: Primer

<400> SEQUENCE: 37
ccatctcatc cctgcgtgtc tccgactcag aagaggattc gatagagttt gatcctggct 60
cag 63

<210> SEQ ID NO 38
<211> LENGTH: 63
<212> TYPE: DNA
<213> ORGANISM: Artificial sequence
<220> FEATURE:
<223> OTHER INFORMATION: Primer

<400> SEQUENCE: 38
ccatctcatc cctgcgtgtc tccgactcag taccaagatc gatagagttt gatcctggct 60
cag 63

<210> SEQ ID NO 39
<211> LENGTH: 63
<212> TYPE: DNA
<213> ORGANISM: Artificial sequence
<220> FEATURE:
<223> OTHER INFORMATION: Primer

<400> SEQUENCE: 39
ccatctcatc cctgcgtgtc tccgactcag cagaaggaac gatagagttt gatcctggct 60
cag 63

<210> SEQ ID NO 40
<211> LENGTH: 63
<212> TYPE: DNA
<213> ORGANISM: Artificial sequence
<220> FEATURE:

-continued

<223> OTHER INFORMATION: Primer

<400> SEQUENCE: 40
ccatctcatc cctgcgtgtc tccgactcag ctgcaagttc gatagagttt gatcctggct 60
cag 63

<210> SEQ ID NO 41
<211> LENGTH: 63
<212> TYPE: DNA
<213> ORGANISM: Artificial sequence
<220> FEATURE:
<223> OTHER INFORMATION: Primer

<400> SEQUENCE: 41
ccatctcatc cctgcgtgtc tccgactcag ttcgtgattc gatagagttt gatcctggct 60
cag 63

<210> SEQ ID NO 42
<211> LENGTH: 63
<212> TYPE: DNA
<213> ORGANISM: Artificial sequence
<220> FEATURE:
<223> OTHER INFORMATION: Primer

<400> SEQUENCE: 42
ccatctcatc cctgcgtgtc tccgactcag ttccgataac gatagagttt gatcctggct 60
cag 63

<210> SEQ ID NO 43
<211> LENGTH: 63
<212> TYPE: DNA
<213> ORGANISM: Artificial sequence
<220> FEATURE:
<223> OTHER INFORMATION: Primer

<400> SEQUENCE: 43
ccatctcatc cctgcgtgtc tccgactcag tgagcggaac gatagagttt gatcctggct 60
cag 63

<210> SEQ ID NO 44
<211> LENGTH: 63
<212> TYPE: DNA
<213> ORGANISM: Artificial sequence
<220> FEATURE:
<223> OTHER INFORMATION: Primer

<400> SEQUENCE: 44
ccatctcatc cctgcgtgtc tccgactcag ctgaccgaac gatagagttt gatcctggct 60
cag 63

<210> SEQ ID NO 45
<211> LENGTH: 63
<212> TYPE: DNA
<213> ORGANISM: Artificial sequence
<220> FEATURE:
<223> OTHER INFORMATION: Primer

<400> SEQUENCE: 45
ccatctcatc cctgcgtgtc tccgactcag tcctcgaatc gatagagttt gatcctggct 60
cag 63

<210> SEQ ID NO 46
<211> LENGTH: 63
<212> TYPE: DNA
<213> ORGANISM: Artificial sequence
<220> FEATURE:
<223> OTHER INFORMATION: Primer

<400> SEQUENCE: 46
ccatctcatc cctgcgtgtc tccgactcag taggtggttc gatagagttt gatcctggct 60
cag 63

<210> SEQ ID NO 47
<211> LENGTH: 63
<212> TYPE: DNA
<213> ORGANISM: Artificial sequence
<220> FEATURE:
<223> OTHER INFORMATION: Primer

<400> SEQUENCE: 47
ccatctcatc cctgcgtgtc tccgactcag tctaacggac gatagagttt gatcctggct 60
cag 63

<210> SEQ ID NO 48
<211> LENGTH: 63
<212> TYPE: DNA
<213> ORGANISM: Artificial sequence
<220> FEATURE:
<223> OTHER INFORMATION: Primer

<400> SEQUENCE: 48
ccatctcatc cctgcgtgtc tccgactcag ttggagtgtc gatagagttt gatcctggct 60
cag 63

<210> SEQ ID NO 49
<211> LENGTH: 63
<212> TYPE: DNA
<213> ORGANISM: Artificial sequence
<220> FEATURE:
<223> OTHER INFORMATION: Primer

<400> SEQUENCE: 49
ccatctcatc cctgcgtgtc tccgactcag tctagaggtc gatagagttt gatcctggct 60
cag 63

<210> SEQ ID NO 50
<211> LENGTH: 63
<212> TYPE: DNA
<213> ORGANISM: Artificial sequence
<220> FEATURE:
<223> OTHER INFORMATION: Primer

<400> SEQUENCE: 50
ccatctcatc cctgcgtgtc tccgactcag tctggatgac gatagagttt gatcctggct 60
cag 63

<210> SEQ ID NO 51
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)

<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 51
ccatctcatc cctgcgtgtc tccgactcag ctaaggtaac gatccgtcaa ttnntttnag 60
ttt 63

<210> SEQ ID NO 52
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 52
ccatctcatc cctgcgtgtc tccgactcag taaggagaac gatccgtcaa ttnntttnag 60
ttt 63

<210> SEQ ID NO 53
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 53
ccatctcatc cctgcgtgtc tccgactcag aagaggattc gatccgtcaa ttnntttnag 60
ttt 63

<210> SEQ ID NO 54
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 54
ccatctcatc cctgcgtgtc tccgactcag taccaagatc gatccgtcaa ttnntttnag 60
ttt 63

<210> SEQ ID NO 55
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 55
ccatctcatc cctgcgtgtc tccgactcag cagaaggaac gatccgtcaa ttnntttnag 60
ttt 63

<210> SEQ ID NO 56
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 56
ccatctcatc cctgcgtgtc tccgactcag ctgcaagttc gatccgtcaa ttnntttnag 60
ttt 63

<210> SEQ ID NO 57
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 57
ccatctcatc cctgcgtgtc tccgactcag ttcgtgattc gatccgtcaa ttnntttnag 60
ttt 63

<210> SEQ ID NO 58
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)

<223> OTHER INFORMATION: n = purine (c or a)

<400> SEQUENCE: 58
ccatctcatc cctgcgtgtc tccgactcag ttccgataac gatccgtcaa ttnntttnag 60
ttt 63

<210> SEQ ID NO 59
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (c or a)

<400> SEQUENCE: 59
ccatctcatc cctgcgtgtc tccgactcag tgagcggaac gatccgtcaa ttnntttnag 60
ttt 63

<210> SEQ ID NO 60
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (c or a)

<400> SEQUENCE: 60
ccatctcatc cctgcgtgtc tccgactcag ctgaccgaac gatccgtcaa ttnntttnag 60
ttt 63

<210> SEQ ID NO 61
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 61
ccatctcatc cctgcgtgtc tccgactcag tcctcgaatc gatccgtcaa ttnntttnag 60
ttt 63

<210> SEQ ID NO 62
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 62
ccatctcatc cctgcgtgtc tccgactcag taggtggttc gatccgtcaa ttnntttnag 60
ttt 63

<210> SEQ ID NO 63
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 63
ccatctcatc cctgcgtgtc tccgactcag tctaacggac gatccgtcaa ttnntttnag 60
ttt 63

<210> SEQ ID NO 64
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 64
ccatctcatc cctgcgtgtc tccgactcag ttggagtgtc gatccgtcaa ttnntttnag 60
ttt 63

<210> SEQ ID NO 65
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 65

-continued

```
ccatctcatc cctgcgtgtc tccgactcag tctagaggtc gatccgtcaa ttnntttnag     60

ttt                                                                   63


<210> SEQ ID NO 66
<211> LENGTH: 63
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (53)..(54)
<223> OTHER INFORMATION: n = pyrimidine (t/u or c)
<220> FEATURE:
<221> NAME/KEY: misc_feature
<222> LOCATION: (58)..(58)
<223> OTHER INFORMATION: n = purine (g or a)

<400> SEQUENCE: 66

ccatctcatc cctgcgtgtc tccgactcag tctggatgac gatccgtcaa ttnntttnag     60

ttt                                                                   63


<210> SEQ ID NO 67
<211> LENGTH: 50
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (31)..(50)
<223> OTHER INFORMATION: n = a, g, c, or t/u, or unknown, or other

<400> SEQUENCE: 67

ccatctcatc cctgcgtgtc tccgactcag nnnnnnnnnn nnnnnnnnnn                50


<210> SEQ ID NO 68
<211> LENGTH: 43
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (24)..(43)
<223> OTHER INFORMATION: n = a, g, c, or t/u, or unknown, or other

<400> SEQUENCE: 68

cctctctatg ggcagtcggt gatnnnnnnn nnnnnnnnnn nnn                       43


<210> SEQ ID NO 69
<211> LENGTH: 44
<212> TYPE: DNA
<213> ORGANISM: Artificial sequence
<220> FEATURE:
<223> OTHER INFORMATION: Primer

<400> SEQUENCE: 69

cctctctatg ggcagtcggt gatcactggt tcaaggttct ggag                      44


<210> SEQ ID NO 70
<211> LENGTH: 41
<212> TYPE: DNA
<213> ORGANISM: Artificial sequence
<220> FEATURE:
<223> OTHER INFORMATION: Primer

<400> SEQUENCE: 70
```

cctctctatg ggcagtcggt gatcatttca cccgcagcct a 41

<210> SEQ ID NO 71
<211> LENGTH: 51
<212> TYPE: DNA
<213> ORGANISM: Artificial sequence
<220> FEATURE:
<223> OTHER INFORMATION: Primer

<400> SEQUENCE: 71
ccatctcatc cctgcgtgtc tccgactcag cactggttca aggttctgga g 51

<210> SEQ ID NO 72
<211> LENGTH: 48
<212> TYPE: DNA
<213> ORGANISM: Artificial sequence
<220> FEATURE:
<223> OTHER INFORMATION: Primer

<400> SEQUENCE: 72
ccatctcatc cctgcgtgtc tccgactcag catttcaccc gcagccta 48

<210> SEQ ID NO 73
<211> LENGTH: 90
<212> TYPE: DNA
<213> ORGANISM: Artificial sequence
<220> FEATURE:
<223> OTHER INFORMATION: Target amplicon
<220> FEATURE:
<221> NAME/KEY: misc_feature
<222> LOCATION: (61)..(61)
<223> OTHER INFORMATION: n = a or g

<400> SEQUENCE: 73
cactggttca aggttctgga gttctccatg aaacttgggt taattttgct cagagtatcc 60
ngagttagcc actaggctgc gggtgaaatg 90

<210> SEQ ID NO 74
<211> LENGTH: 90
<212> TYPE: DNA
<213> ORGANISM: Artificial sequence
<220> FEATURE:
<223> OTHER INFORMATION: Target amplicon
<220> FEATURE:
<221> NAME/KEY: misc_feature
<222> LOCATION: (30)..(30)
<223> OTHER INFORMATION: n = c or t

<400> SEQUENCE: 74
catttcaccc gcagcctagt ggctaactcn ggatactctg agcaaaatta acccaagttt 60
catggagaac tccagaacct tgaaccagtg 90

METHOD AND KIT FOR CHARACTERIZING MICROORGANISMS

CROSS-REFERENCE TO RELATED APPLICATIONS

This application is a continuation of U.S. patent application Ser. No. 15/888,584, filed Feb. 5, 2018, which claims priority to Ser. No. 14/196,999, filed Mar. 4, 2014, now U.S. Pat. No. 9,914,979, which claims the benefit of provisional application Ser. No. 61/772,425, entitled PAN-BACTERIAL METAGENOMICS ASSAY, and filed Mar. 4, 2013, the contents of which are hereby incorporated by reference.

TECHNICAL FIELD

The present disclosure generally relates to methods and kits suitable for use in the diagnostic field for identification of one or more microorganisms.

BACKGROUND

A variety of diagnostic tests are used to assist in the treatment of patients with infections. Currently, there are four main modalities to test for the presence of bacterial infections, which are centered on a main diagnostic technology core. These four main modalities are:

1. Microscopy;
2. Serology;
3. Molecular; and
4. Culture.

Each of these modalities has strengths and weaknesses. Microscopy can detect a large number of infections; however, it often lacks specificity to identify which species or even genus to which a particular infection belongs. Serology can remotely detect the body's immune response to an infectious agent; however, this technique assumes the patient is immuno-competent and only assays a specific bacterium at a time. Molecular diagnostics, typically based on PCR methods, is highly sensitive, but it suffers a similar issue as serology, whereby it only tests for a specific organism (or sometimes only a specific strain) at a time. Culture methods are unable to detect many strains of organisms that are currently unculturable.

Many clinical microbiological identification methods rely on passing through legacy technologies. One such technology is the culture method used as a primary enrichment step. Culture depends partially on the assumption that a disease-causing organism is cultivatable. Non-culturable organisms may be entirely missed as an etiologic agent and emerging or unique organisms could easily be misidentified. Molecular identification tests rely upon the amplification of pathogen specific DNA. These tests are sensitive; however, they usually can only detect only a limited number of organisms or genetic variants. Moreover, the starting material for molecular identification typically relies on culture methods. It is fairly well accepted that the majority of bacteria are present in polymicrobial communities and cannot be cultivated.

A number of microbial detection and identification systems have been developed. New protein-based diagnostics such as MALDI TOF mass spectroscopy systems are now approved in Europe and are pending approval in the United States. These systems include the Bruker and bioMerieux systems. These systems usually require culture first, rely on a limited reductionist diagnostic approach, or have a limited throughput.

Blood stream infections (BSIs) are now the most expensive type of hospital-acquired infection (HAI). A patient's average length of hospital stay is also affected with sepsis patients staying an average of about 23.3 days. Furthermore, it is estimated that up to 40% of patients receive inadequate initial antibiotic treatment that generates its complications and considerations. Every hour that appropriate antibiotic treatment is delayed adds to a patient's mortality rate. Delaying appropriate antibiotic treatment by up to 45 hours is an independent predicting factor for mortality in patients with *S. aureus* infections. This is particularly compelling when culture-based microorganism identification and the susceptibility of the identified microorganism to specific antibiotics often requires between 24 to 72 hours.

Rapid microorganism identification would improve patient outcomes. Mortality can be reduced for patients, and even more so with ICU patients. Length-of-stay reductions could also be realized; studies show that length of hospital stays could be reduced by 2 days per patient or 7 days for an ICU patient with another study showing an overall reduction by 6.2 days per patient. Another study found significant cost savings per patient for pharmacy, laboratory, and bed-related costs when rapid infection-causing microorganism identification was implemented.

Some rapid diagnostic technologies include advanced MALDI TOF, single organism PCR interrogation, and the PCR platform, Biofire. Unfortunately, most of these technologies require preceding culture methods, in which case, as noted above, uncultivable organisms are missed. Second, some of these systems have sensitivity and reproducibility issues such as a relatively high error rate in the most advanced MALDI TOF systems. Furthermore, these systems can suffer from sample volume throughput issues whereby single samples or even single colony isolates are processed one at a time. Finally, these technologies usually do not achieve adequate processing turn-around times.

One approach to identify bacteria has been to clone full-length 16S rRNA genes after polymerase chain reaction (PCR) with primers that would amplify genes from a wide range of organisms. Cloned 16S rRNA genes were sequenced by the Sanger method, which requires two or three reads to cover the entire gene. Accuracy is important because sequencing errors can lead to misclassification. The cost and effort required for the Sanger method limits the extent of sampling, and studies often produced about 100 sequences per sample. This method identifies the dominant microorganisms in a sample, but analysis of less abundant microorganisms is limited.

Accordingly: methods and kits are desired that can (1) reliably identify one or more microorganisms in a time-efficient manner, and/or (2) rapidly sequence multiple regions within microorganism genes (e.g., hypervariable regions of the genes) to reliably identify one or more microorganisms that may be present.

SUMMARY OF THE INVENTION

Various embodiments of the present disclosure relate to methods and kits that can be used to characterize or identify one or more microorganisms. In general, various embodiments of the disclosure provide methods and kits that can be used to characterize and/or identify one or more microorganisms in a relatively short amount of time. The exemplary methods and kits can be used to characterize one or more types of microorganisms, such as bacteria, fungi, protozoa, and viruses and/or one or more species of microorganisms within one or more types of microorganisms. Exemplary methods and systems can evaluate a plurality of microorganisms at the same time, in parallel, to further reduce the amount of time associated with identification or characterization of multiple microorganisms. Further, exemplary methods and kits can be used to characterize or identify one or more microorganisms without requiring a culture step. Because the microorganisms can be characterized or identified in a short amount of time, exemplary methods and kits described herein are suitable for clinical applications, where rapid identification of the microorganism(s) is desired. Further, results from use of exemplary systems and kits can provide care givers with suggested treatments and/or sensitivity and/or therapy resistance information relating to various treatments for the characterized or identified microorganism(s) in a manner that is easy to read and interpret. As used herein "characterized" or "identified" microorganisms refers to a genus or a species of the characterized or identified microorganism(s) or the microorganism itself.

In accordance with exemplary embodiments of the disclosure, a method of characterizing one or more microorganisms includes the steps of (a) preparing an amplicon library with a polymerase chain reaction (PCR) of nucleic acids; (b) sequencing a characteristic gene sequence in the amplicon library to obtain a gene sequence; and (c) characterizing the one or more microorganisms based on the gene sequence using a computer-based genomic analysis of the gene sequence. In accordance with various aspects of these embodiments, the method further includes a step of extracting nucleic acids from a biological sample of a subject. In accordance with additional aspects, the method includes a step of purifying the amplicon library from the PCR reaction. As noted above, the microorganisms can include one or more of bacteria, fungi, protozoa, and viruses. In the case of bacteria, a characteristic gene can be 16S ribosomal RNA (16S rRNA). Exemplary techniques for sequencing a characteristic gene include using an ion semiconductor sequencing platform or a platform based on stepwise addition of reversible terminator nucleotides. In accordance with various aspects of these embodiments, the amplicon library is an ion amplicon library. Various methods can be used to identify one or more microorganisms and/or to characterize one or more microorganisms or DNA fragments thereof based on, for example, a nearest known microorganism or DNA fragment thereof.

Exemplary methods of the present disclosure may further comprise the step of generating a report with microorganisms characterized or identified and treatment (e.g., antibiotic, antifungal, antiprotozoal, and/or antiviral) resistance and susceptibility information for each identified genus and/or species and/or microorganism. The method may also further comprise treating the subject with a treatment identified in the report.

In certain aspects, the PCR reaction uses a forward primer that comprises a target sequence. In the case of bacteria characterization, the target sequence may include a sequence from the 16S rRNA gene such as a hypervariable region selected from the group consisting of V1, V2, V4, and V5.

In certain implementations, the biological sample is a urine sample, a blood sample, a bronchioalveolar lavage, a nasal swab, cerebrospinal fluid, synovial fluid, brain tissue, cardiac tissue, bone, skin, a lymph node tissue or a dental tissue. In some embodiments, the dental tissue is a tooth, a soft tissue, a joint sample, or a dental sample.

In another implementation, the computer-based genomic analysis comprises application of a procedural algorithm to sequencing data. The procedural algorithm may exclude sequences that are present less than five times or constitute less than 1% of the sequencing data.

In accordance with additional exemplary embodiments of the disclosure, a kit for characterizing at least one microorganism includes (a) at least one forward primer comprising an adapter sequence and a priming sequence, for a target sequence, wherein the target sequence comprises a sequence from a characteristic gene sequence; and (b) at least one reverse primer. If one or more suspected microorganisms include bacteria, the target sequence can be from the 16S rRNA gene and a hypervariable region selected from the group consisting of V1, V2, V4, and V5. In certain aspects, the reverse primer comprises a sequence selected from the group consisting of SEQ ID NO: 33 and SEQ ID NO: 34.

In some implementations, the kit comprises a first forward primer and a second forward primer, each of which can include a barcode, a barcode adapter, and a target sequence. By way of example, a target sequence of the first forward primer can include a sequence beginning in V1 and extending towards V2 and the target sequence of the second forward primer can include a sequence beginning in V5 and extending towards V4.

Various additional embodiments of the present disclosure relate to electronic systems and methods that can be used to characterize or identify one or more microorganisms. For example, a method of characterizing one or more microorganisms includes the step of selecting, by a computer, a digital file comprising one or more digital DNA sequences, wherein each of the one or more digital DNA sequences corresponds to a microorganism to be characterized. The computer segments each of the one or more digital DNA sequences into one or more first portions, performs a set of alignments by comparing the one or more first portions to information stored in a first database, determines sequence portions from among the one or more first portions that have an alignment match to the information stored in the first database, performs a set of alignments by comparing the one or more first portions or one or more second portions to information stored in a second database, determines sequence portions from among the one or more first portions or the one or more second portions that have an alignment match to the information stored in the second database, and characterizes one or more microorganisms or DNA fragments thereof based on the alignment match to the information stored in one or more of the first database and the second database.

In accordance with various aspects of these embodiments, the method can be used to characterize multiple microorganisms simultaneously or in parallel, such that multiple microorganisms can be identified in a relatively short amount of time—e.g., preferably in less than forty-eight or less than twenty-four hours.

In accordance with further exemplary embodiments of the disclosure, an article of manufacture including a non-transitory computer readable medium having instructions stored thereon that, in response to execution by a computing device, cause the computing device to perform operations comprising the steps described in the above paragraph.

In accordance with additional exemplary embodiments of the disclosure, a system includes a computer to perform one or more steps, such as the method steps noted above.

In accordance with further exemplary embodiments of the disclosure, a method of automatically characterizing one or more microorganisms can be performed using one or more databases. Exemplary methods include the steps of detecting a sequence run that generates a digital DNA sequence of one or more microorganisms; selecting, by a computer, a digital file comprising one or more digital DNA sequences, wherein each of the one or more digital DNA sequences corresponds to a microorganism to be characterized; segmenting, by the computer, each of the one or more digital DNA sequences into one or more portions; performing, by the computer, a set of alignments by comparing the one or more portions to information stored in one or more databases; determining, by the computer, sequence portions from among the one or more portions that have an alignment match to the information stored in the one or more databases; and characterizing one or more microorganism(s) or DNA fragments thereof based on the alignment match. In accordance with various aspects of these embodiments, the method can be used to characterize multiple microorganisms simultaneously, such that multiple microorganisms can be identified in a relatively short amount of time—e.g., preferably in less than forty-eight or less than twenty-four hours.

In accordance with yet additional exemplary embodiments of the disclosure, an article of manufacture including a non-transitory computer readable medium having instructions stored thereon that, in response to execution by a computing device, cause the computing device to perform operations comprising the steps described in the above paragraph.

In accordance with yet additional exemplary embodiments, a system for automatic computerized generation of microorganism characterization information includes a computer configured to perform the steps of the preceding paragraph.

BRIEF DESCRIPTION OF THE DRAWINGS

A more complete understanding of exemplary embodiments of the present disclosure can be derived by referring to the detailed description and claims when considered in connection with the following illustrative FIGURES.

FIGS. 16-17 illustrate examples of information output in an exemplary report generated in accordance with exemplary embodiments of the disclosure.

Figure 1:
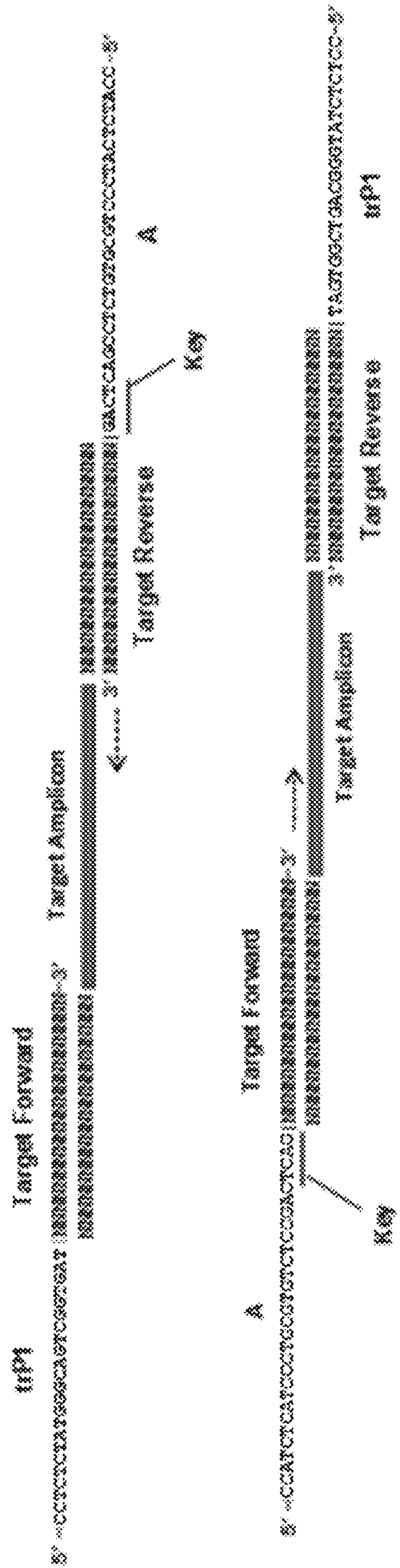
FIG. 1 illustrates bidirectional sequencing using the fusion method. Two primer pairs (SEQ ID NO:67, A and SEQ ID NO:68, trP1) per target region generate two libraries to enable bidirectional sequencing of the target region.

It will be appreciated that elements in the FIGURES are illustrated for simplicity and clarity and have not necessarily been drawn to scale. For example, the dimensions of some of the elements in the FIGURES may be exaggerated relative to other elements to help to improve the understanding of illustrated embodiments of the present disclosure.

DETAILED DESCRIPTION

The description of embodiments provided below is merely exemplary and is intended for purposes of illustration only; the following description is not intended to limit the scope of the disclosure or the claims. Moreover, recitation of multiple embodiments having stated features is not intended to exclude other embodiments having additional features or other embodiments incorporating different combinations of the stated features.

The following disclosure provides methods and kits for characterizing one or more microorganisms. Various examples disclosed herein provide methods and kits for characterizing one or more microorganisms or DNA fragments thereof, such as for example, pathogenic microorganisms in an efficient and timely manner, such that the systems and methods are suitable for use in clinical settings. Exemplary methods and kits can also provide treatment and/or treatment sensitivity information related to the one or more identified microorganism, such that a care provider can use such information. In addition, exemplary methods and kits do not require culturing samples.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

As used herein, the term "biological sample" may include but is not limited to urine, fluid or tissue samples such as blood (e.g., whole blood, blood serum, etc.), bronchioalveolar lavage, nasal swabs, cerebrospinal fluid, synovial fluid, brain and other neurological tissues, cardiac tissue, bone, skin, lymph nodes, dental tissue, and the like from a subject. The dental tissue may be a tooth, a soft tissue, or dental pulp.

Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U" denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage. Nucleotides may also be identified as indicated as shown below in Table 1.

TABLE 1

List of Nucleotide Abbreviations

| Symbol | Meaning | Origin of designation |
|---|---|---|
| A | A | adenine |
| G | G | guanine |
| C | C | cytosine |
| T | T | thymine |
| U | U | uracil |
| R | G or A | purine |
| Y | T/U or C | pyrimidine |
| M | A or C | amino |
| K | G or T/U | keto |
| S | G or C | strong interactions 3H-bonds |
| W | A or T/U | weak interactions 2H-bonds |
| B | G or C or T/U | not a |
| D | A or G or T/U | not c |
| H | A or C or T/U | not g |
| V | A or G or C | not t, not u |
| N | A or G or C or T/U, unknown, or other | any |

Various embodiments of the present disclosure provide metagenomic testing methods that use direct DNA sequencing and computational analysis to enable the detection, characterization or identification, and in the case of novel or divergent organisms the identification of the nearest characterized microorganism, microorganism species, and/or microorganism genus of multiple organisms at the same time. This stands in stark contrast to the myriad of current indirect testing technologies, including serology, T-cell stimulation assays, FISH, and ELISA. Furthermore, exemplary methods can provide a relative measure of the microorganism contribution and diversity within a given sample. In these certain respects, the method may be called Pan-Microbial Metagenomics as it aims to identify the genetic composition and diversity across multiple microorganisms in a sample, simultaneously.

Various exemplary methods can characterize, identify, and/or survey the organisms of an unknown or polymicrobial infection. By using direct DNA sequencing and computational analysis, these methods allow for the characterization or identification of the nearest relative to any detected bacteria in a given clinical sample. Furthermore, the methods may also provide a relative measure of the various microbial contribution and diversity within a given sample in addition to presenting literature based treatment suggestions. Adoption of the disclosed methods in clinical use will have far reaching implications not only by providing superior, unbiased, sequence based diagnosis, but also in reducing patient mortality, morbidity, length of stay, and associated hospital and healthcare costs. In accordance with some examples, ion semiconductor sequencing platforms or similar techniques are utilized to carry out the method because they enable an important aspect of this diagnostic method: speed. In certain aspects, the disclosed diagnostic method enables a turnaround time for results from a patient sample of about 12 hours, about 24 hours, about 48 hours, or about 72 hours. This disclosed method may be performed as a Laboratory Developed Test (LDT) in a Clinical Laboratory Improvement Amendments (CLIA) regulated diagnostics laboratory.

In some implementations, the disclosure provides a system consisting of seven main steps resulting in a CLIA compliant diagnostic billable procedure. These steps include:

1. Point of Care Sampling—Infected tissues and/or fluid samples may be submitted for analysis. Proper collection techniques are used to minimize contamination of the sample by non-targeted bacterial populations. Blood draw sites are cleaned thoroughly with disinfectants to remove bacterial and/or other microbial DNA and cells, while tissue samples are collected using aseptic techniques. The disclosed system is supported with industry standard collection kits if required by the collection facility.
2. Rapid Courier Service—Rapid sample transport to the laboratory is desired to obtain an accurate snapshot of the microbial communities. Extended transport or storage times may result in drifts of the bacterial community that could lead to misleading or distorted results.
3. DNA Extraction—Total DNA content is purified appropriately from a wide range of tissue, fluid, bone and sample types that are adequate for subsequent processing.
4. Molecular Tagging and Amplification—Microbial type specific DNA fragments are selectively amplified for distinct genomic regions and tagged with patient specific molecular markers. These enriched samples of DNA are pooled together in, for example, equimolar amounts to allow even sequencing results across patients and between the genomic regions of interest.
5. Next-Generation DNA Sequencing—Millions of DNA reads are produced through the use of semiconductor sequencing. The sequencing procedure is monitored by a variety of methods to ensure optimal performance and sequencing coverage for each sample. The sequences are sorted based on the molecular tags allowing for consistent and easy identification of the sample source.
6. Bioinformatics Analysis—Software that automatically interfaces with the sequencing software and analyzes the results with the selected sequences, chemistry, and methods can be used with the disclosed methods and system. Such software may utilize industry standard formats and methods of analysis, thus providing reliable and result-based methods.
7. Results Reporting—The software may output the results into a variety of formats and automatically backup intermediary work files documenting the analysis process. Computational metrics may be presented to the analysis technician for review and final report building. In addition to bacterial findings, the disclosed system may provide literature based treatment recommendations with the associated references.

In accordance with various embodiments of the disclosure, a method of characterizing one or more microorganisms includes the steps of preparing an amplicon library with a polymerase chain reaction (PCR) of nucleic acids; sequencing a characteristic gene sequence in the amplicon library to obtain a gene sequence; and characterizing the one or more microorganisms based on the gene sequence using a computer-based genomic analysis of the gene sequence.

In certain aspects, the present disclosure is directed to a test that combines three main components together to provide a unique diagnostic capability that is currently unavailable in the market and that specifically seeks to exploit the exceptional sensitivity of the molecular based assays with a broad spectrum of detection and identification. The three main components are Sample and Library Preparation, DNA Sequencing, and Computer-Based Genomic Analysis.

Accordingly, in one aspect the method of the present disclosure comprises: Sample and Library Preparation, DNA Sequencing, and Computer-Based Genomic Analysis. In one embodiment, the Sample and Library Preparation consists of five steps:

1. DNA Extraction
2. Amplification and Barcoding
3. DNA Purification
4. IonSphere Particle Labeling
5. IonSphere Particle Enrichment However, each of the five steps is not required to practice all embodiments of the disclosure.

DNA extraction may be accomplished by any method available in the art. Nucleic acids can be extracted from a biological sample by a variety of techniques such as those described by Maniatis et al., Molecular Cloning: A Laboratory Manual, Cold Spring Harbor, N.Y., pp. 280-281, (1982), the contents of which is incorporated by reference herein in its entirety. In one embodiment, DNA is extracted from the biological sample with the QIAamp® DNA Mini Kit.

Sample and Library Preparation may also involve the running of a polymerase chain reaction (PCR). PCR is a technique in molecular biology to amplify a single or few copies of a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations.

Most PCR applications employ a heat-stable DNA polymerase, such as Taq polymerase, an enzyme originally isolated from the bacterium *Thermus aquaticus*. This DNA polymerase enzymatically assembles a new DNA strand from DNA building blocks, the nucleotides, by using single-stranded DNA as a template and DNA oligonucleotides (also called DNA primers), which are used for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions. In one embodiment, the present disclosure contemplates a method comprising amplifying a plurality of a complex mixture ("library") of DNA molecules by PCR.

PCR is used to amplify a specific region of a DNA strand (the DNA target) Most PCR methods typically amplify DNA fragments of up to ~10 kilo base pairs (kb), although some techniques allow for amplification of fragments up to 40 kb in size. A basic PCR set up usually involves several components and reagents. These components may include, but are not limited to: i) DNA template that contains the DNA region (target) to be amplified; ii) two primers that are complementary to the 3' ends of each of the sense and anti-sense strand of the DNA target; iii) Taq polymerase or another DNA polymerase with a temperature optimum at around 70° C.; iv) deoxynucleoside triphosphates (dNTPs; also very commonly and erroneously called deoxynucleotide triphosphates), the building blocks from which the DNA polymerases synthesizes a new DNA strand; v) buffer solution, providing a suitable chemical environment for optimum activity and stability of the DNA polymerase; vi) divalent cations, magnesium or manganese ions; generally $Mg^{2+}$ is used, but $Mn^{2+}$ can be utilized for PCR-mediated DNA mutagenesis, as higher $Mn^{2+}$ concentration may increase the error rate during DNA synthesis; and vii) monovalent cation potassium ions.

The PCR is commonly carried out in a reaction volume of 10-200 μl in small reaction tubes (0.2-0.5 ml volumes) in a thermal cycler. The thermal cycler heats and cools the reaction tubes to achieve the temperatures at each step of the reaction. Many modern thermal cyclers make use of the Peltier effect which permits both heating and cooling of the block holding the PCR tubes simply by reversing the electric current. Thin-walled reaction tubes permit favorable thermal conductivity to allow for rapid thermal equilibration. Most thermal cyclers have heated lids to prevent condensation at the top of the reaction tube, but a layer of oil or a ball of wax may also be effective.

Figure 2:
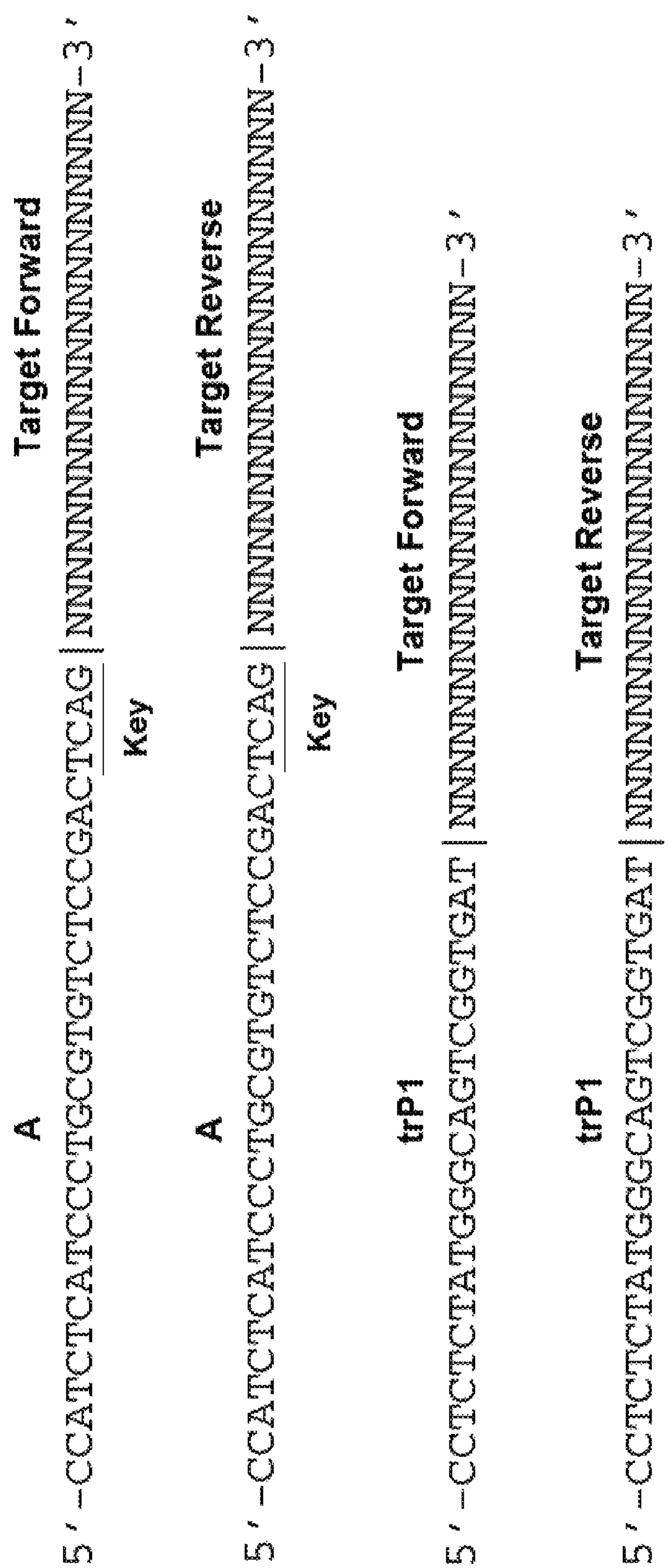
FIG. 2 illustrates fusion PCR primers (SEQ ID NO:67, A and SEQ ID NO:68, trP1) for bidirectional sequencing.
Figure 3:
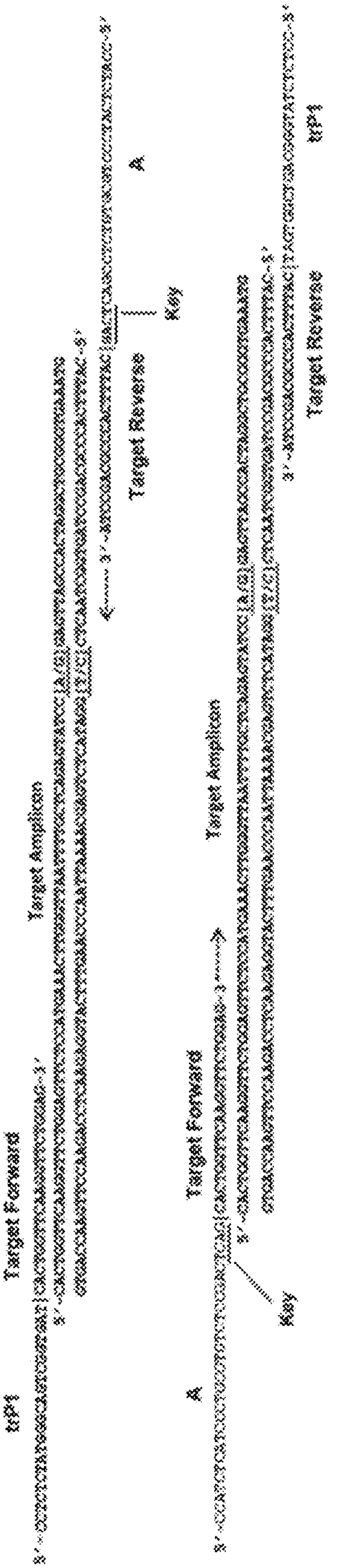
FIG. 3 illustrates example primers (SEQ ID NO:69, trP1 and SEQ ID NO:70, A) and amplicon design (Target Forward, SEQ ID NO:73, Target Reverse, SEQ ID NO:74).

In some embodiments, the method of the present disclosure comprises preparing an ion amplicon library. This may be accomplished with the fusion PCR method using fusion primers to attach the Ion A and truncated P1 (trP1) Adapters to the amplicons as they are generated in PCR (see FIG. 1). The fusion primers contain the A and trP1 sequences at their 5'-ends adjacent to the target-specific portions of the primers (see FIG. 2). The target region is the portion of the genome that will be sequenced in the samples of interest. For example the target region could be an exon, a portion of an exon, or a non-coding region of the genome. Primers are designed so that any sequence variants of interest are located between the primers and so those variants are not masked by the template-specific part of the primer sequences (see FIG. 3). The length of the target region is also carefully considered. In one example, bidirectional sequencing is used. In another example, sequencing proceeds in a single direction.

For bidirectional sequencing, the fusion PCR method for preparing an amplicon library generally uses four fusion primers: two pairs of forward and reverse primers per target region. If sequencing proceeds in a single direction, only one pair of forward and reverse primers per target may be used. The amplicons are designed so that their length, including the fusion primers with adapter sequences, is shorter than the median library size for the target read length of the library (see Table 2).

TABLE 2

| Design of Amplicon Length | |
|---|---|
| Target Read Length | Median Library Size |
| 200 bases (200 base-read library) | ~330 bp |
| 100 bases (100 base-read library) | ~200 bp |

One fusion primer pair has the A adapter region followed by the proximal end of the target sequence, and the other has the trP1 adapter region followed by the distal end of the target sequence. The other fusion primer pair has the adapter sequences A and trP1 swapped. The target-specific portion of each primer should include 15-20 nucleotides of the target region.

In some embodiments, the fusion primer contains a "barcode." The term "barcode" as used herein, refers to any unique, non-naturally occurring, nucleic acid sequence that may be used to identify the originating genome of a nucleic acid fragment. Such barcodes may be sequences including but not limited to: CTAAGGTAAC (SEQ ID NO: 1), TAAGGAGAAC (SEQ ID NO: 2), AAGAGGATTC (SEQ ID NO: 3), TACCAAGATC (SEQ ID NO: 4), CAGAAGGAAC (SEQ ID NO: 5), CTGCAAGTTC (SEQ ID NO: 6), TTCGTGATTC (SEQ ID NO: 7), TTCCGATAAC (SEQ ID NO: 8), TGAGCGGAAC (SEQ ID NO: 9), CTGACCGAAC (SEQ ID NO: 10), TCCTCGAATC (SEQ ID NO: 11), TAGGTGGTTC (SEQ ID NO: 12), TCTAACGGAC (SEQ ID NO: 13), TTGGAGTGTC (SEQ ID NO: 14), TCTAGAGGTC (SEQ ID NO: 15), or TCTGGATGAC (SEQ ID NO: 16). Barcodes may, optionally, be followed by a barcode adapter, for example, GAT (SEQ ID NO: 17). While exemplary barcodes are listed, any barcode of an appropriate length containing an arbitrary DNA sequence may be used with the method of the present disclosure. An appropriate length for the barcode may be about 5 nucleotides, about 6 nucleotides, about 7 nucleotides, about 8 nucleotides, about 9 nucleotides, about 10 nucleotides, about 15 nucleotides or about 20 nucleotides.

In accordance with various aspects of the present disclosure, the target sequence is a segment from the 16S rRNA gene of a microorganism. In some implementations, the target sequence may comprise one or more hypervariable regions from the 16S rRNA gene selected from V1, V2, V3, V4, V5, V6, V7, V8, and V9. For example, the target sequence comprises a sequence from any one of V1, V2, V4, and V5. In another implementation, the target sequence may comprise a sequence beginning in V1 and extending towards V2, a sequence beginning in V2 and extending towards V1, a sequence beginning in V4 and extending towards V5, or a sequence beginning in V5 and extending towards V4. The target sequence may be anywhere from about 5 nucleotides in length to about 40 nucleotides in length, from about 10 nucleotides in length to about 30 nucleotides in length, from about 15 nucleotides in length to about 25 nucleotides in length, etc. In some implementations, the target sequence is about 5 nucleotides in length, about 10 nucleotides in length, about 15 nucleotides in length, about 20 nucleotides in length, about 25 nucleotides in length, about 30 nucleotides in length, about 35 nucleotides in length, or about 40 nucleotides in length. Non-limiting examples of 16S rRNA target sequences that may be used in the fusion primers are listed in Table 3.

Table 3

| 16S rRNA Target Sequences for Fusion Primers | | |
|---|---|---|
| Primer Name | Sequence (5'-3') | SEQ ID NO: |
| V1/2 | AGAGTTTGATCCTGGCTCAG | SEQ ID NO: 18 |
| V5/4 | CCGTCAATTYYTTTRAGTTT | SEQ ID NO: 19 |
| U1492R | GGTTACCTTGTTACGACTT | SEQ ID NO: 20 |
| 928F | TAAAACTYAAAKGAATTGACGGG | SEQ ID NO: 21 |
| 336R | ACTGCTGCSYCCCGTAGGAGTCT | SEQ ID NO: 22 |
| 1100F | YAACGAGCGCAACCC | SEQ ID NO: 23 |
| 1100R | GGGTTGCGCTCGTTG | SEQ ID NO: 24 |
| 337F | GACTCCTACGGGAGGCWGCAG | SEQ ID NO: 25 |
| 907R | CCGTCAATTCCTTTRAGTTT | SEQ ID NO: 26 |
| 785F | GGATTAGATACCCTGGTA | SEQ ID NO: 27 |
| 805R | GACTACCAGGGTATCTAATC | SEQ ID NO: 28 |
| 533F | GTGCCAGCMGCCGCGGTAA | SEQ ID NO: 29 |
| 518R | GTATTACCGCGGCTGCTGG | SEQ ID NO: 30 |

In another aspect of the present disclosure, the target sequence is a segment of an antibiotic resistance gene. Non-limiting examples of such antibiotic resistance genes include $bla_{tem}$, $bla_{shv}$, $bla_{rob}$, $bla_{oxa}$, blaZ, aadB, aacC1, aacC2, aacC3, aac6'-IIa, aacA4, aad(6'), vanA, vanB, vanC, msrA, sarA, aac(6') aph(2"), vat, vga, ermA, ermB, ermC, mecA, int, sul, mecA, aac2ia, aac2ib, aac2ic, aac2id, aac2i, aac3ia, aac3iia, aac3iib, aac3iii, aac3iv, aac3ix, aac3vi, aac3viii, aac3vii, aac3x, aac6i, aac6ia, aac6ib, aac6ic, aac6ie, aac6if, aac6ig, aac6iia, aac6iib, aad9, aad9ib, aadd, acra, acrb, adea, adeb, adec, amra, amrb, ant2ia, ant2ib, ant3ia, ant4iia, ant6ia, aph33ia, aph33ib, aph3ia, aph3ib, aph3ic, aph3iiia, aph3iva, aph3va, aph3vb, aph3via, aph3viia, aph4ib, aph6ia, aph6ib, aph6ic, aph6id, arna, baca, bcra, bcrc, bl1_acc, bl1_ampc, bl1_asba, bl1_ceps, bl1_cmy2, bl1_ec, bl1_fox, bl1_mox, bl1_och, bl1_pao, bl1_pse, bl1_sm, bl2a_1, bl2a_exo, bl2a_iii2, bl2a_iii, bl2a_kcc, bl2a_nps, bl2a_okp, bl2a_pc, bl2be_ctxm, bl2be_oxyl, bl2be_per, bl2be_shv2, bl2b_rob, bl2b_tem1, bl2b_tem2, bl2b_tem, bl2b_tle, bl2b_ula, bl2c_bro, b12c_pse1, b12c_pse3, bl2d_lcr1, bl2d_moxa, bl2d_oxa10, bl2d_oxa1, bl2d_oxa2, bl2d_oxa5, bl2d_oxa9, bl2d_r39, bl2e_cbla, bl2e_cepa, bl2e_cfxa, bl2e_fpm, bl2e_y56, bl2f_nmca, bl2f_sme1, bl2_ges, bl2_kpc, bl2_len, bl2_veb, bl3_ccra, bl3_cit, bl3_cpha, bl3_gim, bl3_imp, bl3_l, bl3_shw, bl3_sim, bl3_vim, ble, blt, bmr, cara, cata10, cata11, cata12, cata13, cata14, cata15, cata16, cata1, cata2, cata3, cata4, cata5, cata6, cata7, cata8, cata9, catb1, catb2, catb3, catb4, catb5, ceoa, ceob, cml_e1, cml_e2, cml_e3, cml_e4, cml_e5, cml_e6, cml_e7, cml_e8, dfra10, dfra12, dfra13, dfra14, dfra15, dfra16, dfra17, dfra19, dfra1, dfra20, dfra21, dfra22, dfra23, dfra24, dfra25, dfra25, dfra25, dfra26, dfra5, dfra7, dfrb1, dfrb2, dfrb3, dfrb6, emea, emrd, emre, erea, ereb, erma, ermb, ermc, ermd, erme, ermf, ermg, ermh, ermn, ermo, ermq, ermr, erms, ermt, ermu, ermv, ermw, ermx, ermy, fosa, fosb, fosc, fosx, fusb, fush, ksga, lmra, lmrb, lnua, lnub, lsa, maca, macb, mdte, mdtf, mdtg, mdth, mdtk, mdtl, mdtm, mdtn, mdto, mdtp, meca, mecrl, mefa, mepa, mexa, mexb, mexc, mexd, mexe, mexf, mexh, mexi, mexw, mexx, mexy, mfpa, mpha, mphb, mphc, msra, norm, oleb, opcm, opra, oprd, oprj, oprm, oprn, otra, otrb, pbpla, pbp1b, pbp2b, pbp2, pbp2x, pmra, qac, qaca, qacb, qnra, qnrb, qnrs, rosa, rosb, smea, smeb, smec, smed, smee, smef, srmb, sta, str, sul1, sul2, sul3, tcma, tcr3, tet30, tet31, tet32, tet33, tet34, tet36, tet37, tet38, tet39, tet40, teta, tetb, tetc, tetd, tete, tetg, teth, tetj, tetk, tetl, tetm, teto, tetpa, tetpb, tet, tetq, tets, tett, tetu, tetv, tetw, text, tety, tetz, tlrc, tmrb, tolc, tsnr, vana, vanb, vanc, vand, vane, yang, vanha, vanhb, vanhd, vanra, vanrb, vanrc, vanrd, vanre, vanrg, vansa, vansb, vansc, vansd, vanse, vansg, vant, vante, vantg, vanug, vanwb, vanwg, vanxa, vanxb, vanxd, vanxyc, vanxye, vanxyg, vanya, vanyb, vanyd, vanyg, vanz, vata, vatb, vatc, vatd, vate, vgaa, vgab, vgba, vgbb, vph, ykkc, and ykkd (see the Antibiotic Resistance Genes Database (ARDB) available online).

When barcodes are incorporated into PCR primers for bidirectional sequencing, the primers may comprise the following sequences:

```
Forward Primer #1:
                                          (SEQ ID NO: 31)
5'-CCATCTCATCCCTGCGTGTCTCCGACTCAG-3';
followed by a barcode, a barcode adapter, and a
stretch of about 20 nucleotides from the target
sequence

Reverse Primer #1:
                                          (SEQ ID NO: 31)
5'-CCATCTCATCCCTGCGTGTCTCCGACTCAG-3';
followed by a barcode, a barcode adapter, and a
stretch of about 20 nucleotides from the target
sequence

Forward Primer #2:
                                          (SEQ ID NO: 32)
5'-CCTCTCTATGGGCAGTCGGTGAT-3';
followed by a stretch of about 20 nucleotides
from the target sequence

Reverse Primer #2:
                                          (SEQ ID NO: 32)
5'-CCTCTCTATGGGCAGTCGGTGAT-3'.
followed by a stretch of about 20 nucleotides
from the target sequence
```

In some aspects of the present disclosure, sequencing proceeds in one direction and the reverse primers do not include a barcode sequence or a barcode adapter.

The forward and reverse primers may comprise SEQ ID NO: 31 or SEQ ID NO: 32 and a stretch of about 5 nucleotides, about 10 nucleotides, about 15 nucleotides, about 20 nucleotides, about 25 nucleotides, or about 30 nucleotides from the target sequence.

In certain embodiments, the reverse primer comprises a sequence selected from CCTCTCTATGGGCAGTCGGT-GATCTGCTGCCTYCCGTA (SEQ ID NO: 33) and CCTCTCTATGGGCAGTCGGTGATAYTGGGYD-TAAAGNG (SEQ ID NO: 34).

In certain embodiments, the method of the present disclosure comprises sequencing 16S ribosomal RNA (16S rRNA) or other sequence with an ion semiconductor sequencing platform. The term "ion semiconductor sequencing platform" refers to any device and/or method that detects the production of hydrogen ions during a chemical condensation reaction. The device and/or method quantitates the production of hydrogen ions by changes in the pH of a mixture and/or solution. For example, nucleic acids may be sequenced by measuring pH fluctuations in a mixture during amplification of a nucleic acid sequence.

There are several probes or primers that may be used in accordance with the present disclosure. These probes/primers can take on a variety of configurations and may have a variety of structural components described in more detail below. The first step probe may be an allele specific probe or locus specific probe. "Allele specific" probe or primer refers to a probe or primer that hybridizes to a target sequence and discriminates between alleles or hybridizes to a target sequence and is modified in an allele specific manner. "Locus specific" probe or primer refers to a probe or primer that hybridizes to a target sequence in a locus specific manner, but does not necessarily discriminate between alleles. A locus specific primer also may be modified, i.e., extended as described below, such that it includes information about a particular allele, but the locus specific primer does not discriminate between alleles.

In many embodiments, the probes or primers comprise one or more universal priming site(s) and/or adapters, both of which are described below.

A size of the primer and probe nucleic acid may vary with each portion of the probe and the total length of the probe in general varying from 5 to 500 nucleotides in length. Each portion can be between 10 and 100, between 15 and 50, or 10 to 35, depending on the use and amplification technique. Thus, for example, the universal priming site(s) of the probes can each be about 15-20 nucleotides in length, or 18 nucleotides. The adapter sequences of the probes can be from 15-25 nucleotides in length, or about 20 nucleotides. The target specific portion of the probe can be from 15-50 nucleotides in length. In addition, the primer may include an additional amplification priming site.

In accordance with some examples of the disclosure, the allele or locus specific probe or probes comprise a target domain substantially complementary to a first domain of the target sequence. In general, probes of the present disclosure are designed to be complementary to a target sequence (either the target sequence of the sample or to other probe sequences, as is described herein), such that hybridization of the target and the probes of the present disclosure occurs. This complementarity need not be perfect; there may be any number of base pair mismatches that will interfere with hybridization between the target sequence and the single stranded nucleic acids of the present disclosure. However, if the number of mutations is so great that no hybridization can occur under even the least stringent of hybridization conditions, the sequence is not a complementary target sequence. Thus, "substantially complementary" as used herein means that the probes are sufficiently complementary to the target sequences to hybridize under the selected reaction conditions.

In one embodiment the target specific portion includes a combinatorial mixture of each nucleotide at each position. In addition the primer includes a universal priming sequence and an allele specific position. The universal priming sequence can be specific for the particular nucleotide at the allele specific position. That is, the locus-specific allele selectivity portions of the primer can be replaced with a universal targeting domain that includes a region where each position is represented by a combinatorial mixture of nucleotides. One of the positions in the universal region (not necessarily the 3' position) is paired with the genomic region to be analyzed.

In another example, one of the probes further comprises an adapter sequence, (sometimes referred to in the art as "zip codes" or "bar codes"). Adapters facilitate immobilization of probes to allow the use of "universal arrays." That is, arrays (either solid phase or liquid phase arrays) are generated that contain capture probes that are not target specific, but rather specific to individual (preferably) artificial adapter sequences.

Thus, an "adapter sequence" is a nucleic acid that is generally not native to the target sequence, i.e. is exogenous, but is added or attached to the target sequence. It should be noted that in this context, the "target sequence" can include the primary sample target sequence, or can be a derivative target such as a reactant or product of the reactions outlined herein; thus for example, the target sequence can be a PCR product, a first ligation probe or a ligated probe in an OLA reaction, etc. The terms "barcodes," "adapters," "addresses," "tags," and "zip codes" have all been used to describe artificial sequences that are added to amplicons to allow separation of nucleic acid fragment pools. One exemplary form of adapters is hybridization adapters, which can be chosen so as to allow hybridization to the complementary capture probes on a surface of an array. Adapters serve as unique identifiers of the probe and thus of the target sequence. In general, sets of adapters and the corresponding capture probes on arrays are developed to minimize cross-hybridization with both each other and other components of the reaction mixtures, including the target sequences and sequences on the larger nucleic acid sequences outside of the target sequences (e.g. to sequences within genomic DNA). Other forms of adapters are mass tags that can be separated using mass spectroscopy, electrophoretic tags that can be separated based on electrophoretic mobility, etc. Some adapter sequences are outlined in U.S. Ser. No. 09/940,185, filed Aug. 27, 2001, hereby incorporated by reference in its entirety to the extent the contents thereof do not conflict with the present disclosure. Exemplary adapters are those that meet the following criteria. They are not found in a genome, preferably a human or microbial genome, and they do not have undesirable structures, such as hairpin loops.

As will be appreciated by those in the art, the attachment, or joining, of the adapter sequence to the target sequence can be done in a variety of ways. In one embodiment, the adapter sequences are added to the primers of the reaction (extension primers, amplification primers, readout probes, genotyping primers, Rolling Circle primers, etc.) during the chemical synthesis of the primers. The adapter then gets added to the reaction product during the reaction; for example, the primer gets extended using a polymerase to form the new target sequence that now contains an adapter sequence. Alternatively, the adapter sequences can be added enzymatically. Furthermore, the adapter can be attached to the target after synthesis; this post-synthesis attachment can be either covalent or non-covalent. In another embodiment the adapter is added to the target sequence or associated with a particular allele during an enzymatic step. That is, to achieve the level of specificity necessary for highly multiplexed reactions, the product of the specificity or allele specific reaction preferably also includes at least one adapter sequence.

One or more of the specificity primers can include a first portion comprising the adapter sequence and a second portion comprising the priming sequence. Extending the amplification primer results in target sequences that comprise the adapter sequences. The adapter sequences are designed to be substantially complementary to capture probes.

In addition, the adapter can be attached either on the 3' or 5' ends, or in an internal position, depending on the configuration of the system.

In accordance with one example, the use of adapter sequences allows the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In an exemplary embodiment, an array of different and usually artificial capture probes are made; that is, the capture probes do not have to be complementarity to known target sequences. The adapter sequences can then be incorporated in the target probes.

As can be appreciated, the length of the adapter sequences will vary, depending on the desired "strength" of binding and the number of different adapters desired. In accordance with various examples, an adapter sequences range from about 6 to about 500 basepairs in length, or 8 to about 100 basepairs, or about 10 to about 25 basepairs.

In one example, the adapter sequence uniquely identifies the target analyte to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target analyte.

In one embodiment, the adapter includes both an identifier region and a region that is complementary to capture probes on a universal array as described above. In this embodiment, the amplicon hybridizes to capture probes on a universal array. Detection of the adapter can be accomplished following hybridization with a probe that is complementary to the adapter sequence. The probe can be labeled as described herein.

In general, unique adapter sequences are used for each unique target analyte. That is, the elucidation or detection of a particular adapter sequence allows the identification of the target analyte to which the target probe containing that adapter sequence bound. However, in some cases, it is possible to "reuse" adapter sequences and have more than one target analyte share an adapter sequence.

The adapters can contain different sequences or properties that are indicative of a particular target molecule. That is, each adapter can uniquely identify a target sequence. As described above, the adapters can be amplified to form amplicons. The adapter is detected as an indication of the presence of the target analyte, i.e. the particular target nucleic acid. The use of adapters in combination with amplification following a specific binding event allows for highly multiplexed reactions to be performed.

Also, the probes are constructed so as to contain the desired priming site or sites for the subsequent amplification scheme. For example, the priming sites can be universal priming sites. By "universal priming site" or "universal priming sequences" herein is meant a sequence of the probe that will bind a primer for amplification.

By way of example, when amplification methods requiring two primers such as PCR are used, each probe can comprise an upstream universal priming site (UUP) and a downstream universal priming site (DUP). Again, "upstream" and "downstream" are not meant to convey a particular 5'-3' orientation, and will depend on the orientation of the system. Only a single UUP sequence and a single DUP sequence can be used in a probe set, although different assays or different multiplexing analysis may utilize a plurality of universal priming sequences. In some embodiments, probe sets may comprise different universal priming sequences. In addition, the universal priming sites are preferably located at the 5' and 3' termini of the target probe (or the ligated probe), as only sequences flanked by priming sequences will be amplified.

In addition, universal priming sequences are generally chosen to be as unique as possible given the particular assays and host genomes to ensure specificity of the assay. However, as will be appreciated, sets of priming sequences/primers may be used.

When two priming sequences are used, the orientation of the two priming sites can be generally different. That is, one PCR primer will directly hybridize to the first priming site, while the other PCR primer will hybridize to the complement of the second priming site. Stated differently, the first priming site is in sense orientation, and the second priming site is in antisense orientation.

In general, highly multiplexed reactions can be performed, with all of the universal priming sites being the same for all reactions. Alternatively, "sets" of universal priming sites and corresponding probes can be used, either simultaneously or sequentially. The universal priming sites are used to amplify the modified probes to form a plurality of amplicons that are then detected in a variety of ways, as outlined herein.

Accordingly, various examples of the present disclosure provide first target probe sets. By "probe set" herein is meant a plurality of target probes that are used in a particular multiplexed assay. First target probe sets can each comprise at least a first universal priming site.

The target probe may also comprise a label sequence, i.e. a sequence that can be used to bind label probes and is substantially complementary to a label probe. Such system is sometimes referred to in the art as "sandwich-type" assays. That is, by incorporating a label sequence into the target probe, which is then amplified and present in the amplicons, a label probe comprising primary (or secondary) detection labels can be added to the mixture, either before addition to the array or after. This allows the use of high concentrations of label probes for efficient hybridization. It is possible to use the same label sequence and label probe for all target probes on an array; alternatively, different target probes can have a different label sequence. Similarly, the use of different label sequences can facilitate quality control; for example, one label sequence (and one color) can be used for one strand of the target, and a different label sequence (with a different color) for the other; and in this case only if both colors are present at the same basic level is a positive called.

Thus, the present disclosure provides target probes that comprise any, all or any combination of universal priming sequences, bioactive agents (e.g. target specific portion(s)), adapter sequence(s), optionally an additional amplification priming sequence and optionally label sequences. These target probes can then added to the target sequences to form hybridization complexes. When nucleic acids are the target, the hybridization complexes can contain portions that are double stranded (the target-specific sequences of the target probes hybridized to a portion of the target sequence) and portions that are single stranded (the ends of the target probes comprising the universal priming sequences and the adapter sequences, and any unhybridized portion of the target sequence).

In some embodiments, the purified DNA from the sample is analyzed by Sequencing by Synthesis (SBS) techniques. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in some of the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). In some methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels. Thus, in a doublet sequencing reagent having a mixture of A/C both the A and C can be labeled with the same fluorophore. Furthermore, when doublet delivery methods are used all of the different nucleotide monomers can have the same label or different labels can be used, for example, to distinguish one mixture of different nucleotide monomers from a second mixture of nucleotide monomers. For example, using the [First delivery nucleotide monomers]+[Second delivery nucleotide monomers] nomenclature set forth above and taking an example of A/C+(1/T), the A and C monomers can have the same first label and the G and T monomers can have the same second label, wherein the first label is different from the second label. Alternatively, the first label can be the same as the second label and incorporation events of the first delivery can be distinguished from incorporation events of the second delivery based on the temporal separation of cycles in an SBS protocol. Accordingly, a low resolution sequence representation obtained from such mixtures will be degenerate for two pairs of nucleotides (T/G, which is complementary to A and C, respectively; and C/A which is complementary to G/T, respectively).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another example type of SBS, cycle sequencing is accomplished by stepwise addition of reversible terminator nucleotides containing, for example, a cleavable or photobleachable dye label as described, for example, in U.S. Pat. Nos. 7,427,671, 7,414,163 and 7,057,026, the disclosures of which are incorporated herein by reference. This approach is being commercialized by Solexa (now Illumina Inc.), and is also described in WO 91/06678 and WO 07/123,744 (filed in the United States patent and trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In other embodiments, Ion Semiconductor Sequencing is utilized to analyze the purified DNA from the sample. Ion Semiconductor Sequencing is a method of DNA sequencing based on the detection of hydrogen ions that are released during DNA amplification. This is a method of "sequencing by synthesis," during which a complementary strand is built is based on the sequence of a template strand.

For example, a microwell containing a template DNA strand to be sequenced can be flooded with a single species of deoxyribonucleotide (dNTP). If the introduced dNTP is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple dNTP molecules will be incorporated in a single cycle. This leads to a corresponding number of released hydrogens and a proportionally higher electronic signal.

This technology differs from other sequencing technologies in that no modified nucleotides or optics are used. Ion semiconductor sequencing may also be referred to as ion torrent sequencing, pH-mediated sequencing, silicon sequencing, or semiconductor sequencing. Ion semiconductor sequencing was developed by Ion Torrent Systems Inc. and may be performed using a bench top machine. It is believed that hydrogen ion release occurs during nucleic acid amplification because of the formation of a covalent bond and the release of pyrophosphate and a charged hydrogen ion. Ion semiconductor sequencing exploits these facts by determining if a hydrogen ion is released upon providing a single species of dNTP to the reaction.

For example, microwells on a semiconductor chip that each contain one single-stranded template DNA molecule to be sequenced and one DNA polymerase can be sequentially flooded with unmodified A, C, G or T dNTP. The hydrogen ion that is released in the reaction changes the pH of the solution, which is detected by a hypersensitive ion sensor. The unattached dNTP molecules are washed out before the next cycle when a different dNTP species is introduced.

Beneath the layer of microwells is an ion sensitive layer, below which is a hypersensitive ISFET ion sensor. All layers are contained within a CMOS semiconductor chip, similar to that used in the electronics industry. Each released hydrogen ion triggers the ISFET ion sensor. The series of electrical pulses transmitted from the chip to a computer is translated into a DNA sequence, with no intermediate signal conversion required. Each chip contains an array of microwells with corresponding ISFET detectors. Because nucleotide incorporation events are measured directly by electronics, the use of labeled nucleotides and optical measurements are avoided.

An example of a Ion Semiconductor Sequencing technique suitable for use in the methods of the provided disclosure is Ion Torrent sequencing (U.S. Patent Application Numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety to the extent such contents do not conflict with the present disclosure. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton ($H^+$), which signal detected and recorded in a sequencing instrument. The signal strength is proportional to the number of nucleotides incorporated. User guides describe in detail the Ion Torrent protocol(s) that are suitable for use in methods of the disclosure, such as Life Technologies' literature entitled "Ion Sequencing Kit for User Guide v. 2.0" for use with their sequencing platform the Personal Genome Machine™ (PCG), the contents of which are incorporated herein by reference, to the extent such contents do not conflict with the present disclosure.

In accordance with various examples, Ion Semiconductor Sequencing is used to maximize detection of specific microorganisms by sequencing, for example, 16S rRNA hypervariable regions on the Ion Torrent PGM platform (Life Technologies, Carlsbad, California). A primary PCR step is carried out using chimeric primers containing a sequence specific portion for amplifying the exons 16S rRNA hypervariable regions interest along with adapter sequences for sequencing analysis. Suitable sequence specific primers can be designed using any suitable method. The primary consideration is the Tm of the sequence specific portion. For example, primers with target specific Tm values ranging from about 52° C. to about 68° C. may generate successful amplification products with chimeric oligonucleotides. Another consideration for primer design is the size of the amplicon.

In some embodiments, as a part of the sample preparation process, "barcodes" may be associated with each sample. In this process, short oligos are added to primers, where each different sample uses a different oligo in addition to a primer.

The term "library", as used herein refers to a library of genome-derived sequences. The library may also have sequences allowing amplification of the "library" by the polymerase chain reaction or other in vitro amplification methods well known to those skilled in the art. The library may also have sequences that are compatible with next-generation high throughput sequencers such as an ion semiconductor sequencing platform.

In certain embodiments, the primers and barcodes are ligated to each sample as part of the library generation process. Thus during the amplification process associated with generating the ion amplicon library, the primer and the short oligo are also amplified. As the association of the barcode is done as part of the library preparation process, it is possible to use more than one library, and thus more than one sample. Synthetic DNA barcodes may be included as part of the primer, where a different synthetic DNA barcode may be used for each library. In some embodiments, different libraries may be mixed as they are introduced to a flow cell, and the identity of each sample may be determined as part of the sequencing process. Sample separation methods can be used in conjunction with sample identifiers. For example a chip could have 4 separate channels and use 4 different barcodes to allow the simultaneous running of 16 different samples.

In some embodiments, the method of the present disclosure comprises classifying the species or genus of the microorganism with a computer-based genomic analysis of the sequence data from the ion semiconductor sequencing platform. The method may further comprise generating a report with the species of microorganisms identified and antibiotic resistance information for each species. Exemplary systems and methods for characterizing, identifying, and/or classifying the microorganisms are discussed below.

In some aspects of the present disclosure, the computer-based genomic analysis makes use of a procedural algorithm. By way of particular example, an Ion Sequencing data can be imported into CLC Workbench and the sequences sorted. Sequences that are less than 100 bp in length can be removed. The entire data set (e.g., >100 bp) is then BLASTed to a local 16S library of named bacteria or other type of microorganism. In the case of bacteria, the local 16S library can be compiled from data available from the National Center for Biotechnology Information (NCBI). The resulting data can be sorted by BLAST hit length. The distribution of the sequence reads from the sequencer is analyzed to determine an appropriate cut-off to obtain a significant number of reads. Less than 20 reads is can be deemed not acceptable. Generally, hundreds if not thousands of high quality long reads are included. The returned species greater than the cut-off can be tabulated for the number of times they occur as a BLAST result. Typically, sequences can be present 5 or more times and can constitute at least 1% of the sample to be reported. Any sequence that does not meet both of these requirements may not be reported. Depending on the cut-off used, a confidence percentage is applied to the resulting species, genus, or microorganism calls. This data may be presented graphically. In one example, a maximum of six of the top species with a complete listing in tabular format is reported. Treatment (e.g., antibacterial, antifungal, antiviral, and/or antiprotozoal) susceptibilities for each genus/species/microorganism characterized or identified may also be reported. The references for all of the treatment susceptibilities may be listed in the report.

Classification of bacteria has been greatly revised by analysis of nucleic acid sequences. The section below contains a classification of bacteria that are human pathogens that may be identified in accordance with the present disclosure.

Gram-Positive Eubacteria
Actinobacteria
Actinobacteria are High G+C Gram-Positive Eubacteria.
- order: Actinomycetales
  - suborder: Actinomycineae
    - family: Actinomyecetaceae
      - *Actinomyces israelii* (*Streptothrix israeli* Kruse 1896) Lachner-Sandoval 1898 (actinomycosis)
      - *Actinomyces naeslundi* Thompson & Lovestedt 1951 (actinomycosis)
      - *Actinomyces meyeri* (*Actinobacterium meyeri* Prévot 1938) E. P. Cato et al. 1984 (actinomycosis)
      - *Actinomyces odontolyticus* Batty 1958 (actinomycosis)
      - *Actinomyces viscosus* (*Odontomyces viscosus* Howell et al. 1965) Georg et al. 1969 (actinomycosis)
  - suborder: Propionibacterineae
    - family: Propionibacteriaceae
      - *Propionibacterium acnes* (*Bacillus acnes* Gilchrist 1900) Douglas & Gunter 1946 (actinomycosis)
  - suborder; Micrococcineae
    - family: Cellulomonadaceae
      - *Tropheryma whipplei* (*Tropheryma whippelii* 1991) La Scola et al. 2001 (Whipple disease)
  - suborder: Streptosporangineae
    - family: Thermomonosporaceae
      - *Actinomadura madurae* (*Streptothrix madurae* Vincent 1894) Lechevalier and Lechevalier 1968 (actinomycetoma)
      - *Actinomadura pelletieri* (*Micrococcus pelletieri* Laveran 1906) Lechevalier and Lechevalier 1968 (actinomycetoma)
    - Nocardiopsaceae
      - *Nocardiopsis dassonvillei* (*Streptothrix dassonvillei* Brocq-Rousseau 1904) Meyer 1976 (actinomycetoma)
  - suborder: Streptomycineae
    - family: Streptomycetaceae
      - *Streptomyces somaliensis* (*Indiella somaliensis* Brumpt 1906) Waksman and Henrici 1948 (actinomycetoma)
  - suborder: Corynebacterineae
    - family: Nocardiaceae
      - *Nocardia asteroides* (*Cladothrix asteroides* Eppinger 1891) Blanchard 1896 (nocardiosis, actinomycetoma)
      - *Nocardia brasiliensis* (*Discomyces brasiliensis* Lindenberg 1909) Pinoy 1913 (nocardiosis, actinomycetoma)
      - *Nocardia otitidiscaviarum* Snijders 1924 (nocardiosis, actinomycetoma)
      - *Nocardia transvalensis* Pijper and Pullinger 1927 (nocardiosis)
      - *Rhodococcus equi* (*Corynebacterium equi* Magnusson 1923) Goodfellow & Alderson 1977
    - family: Mycobacteriaceae
      - *Mycobacterium leprae* Hansen, 1874 (leprosy)
      - *Mycobacterium tuberculosis* complex
        - *Mycobacterium tuberculosis* Zopf 1883 (tuberculosis)
        - *Mycobacterium africanum* Castets et al. 1969 (tuberculosis)
        - *Mycobacterium bovis* Karlson & Lessel 1970 (tuberculosis)

*Mycobacterium avium* complex (MAC)
*Mycobacterium avium* Chester 1901
*Mycobacterium intracellulare* (*Nocardia intracellularis* Cuttino and McCabe 1949) Runyon 1965
*Mycobacterium scrofulaceum* Prissick and Masson 1956
*Mycobacterium fortuitum* complex (MFC)
*Mycobacterium fortuitum* da Costa Cruz 1938
*Mycobacterium chelonae* Bergey et al. 1923
*Mycobacterium kansasii* Hauduroy 1955
*Mycobacterium ulcerans* MacCallum et al. 1950 (Buruli ulcer)
*Mycobacterium abscessus* Moore and Frerichs 1953
*Mycobacterium haemophilum* Sompolinsky et al. 1978
*Mycobacterium marinum* Aronson 1926
*Mycobacterium simiae* Karassova et al. 1965
*Mycobacterium xenopi* Schwabacher 1959
family: Corynebacteriaceae
*Corynebacterium diphtheriae* (*Bacillus diphtheriae* Kruse 1886) Lehmann and Neumann 1896 (diphtheria)
*Corynebacterium minutissimum* Sarkany et al. 1962 (erythrasma)
*Corynebacterium jeikeium* Jackman et al. 1988
order: Bifidobacteriales
family: Bifidobacteriaceae
*Gardnerella vaginalis* (*Haemophilus vaginalis* Gardner and Dukes 1955) Greenwood and Pickett 1980 (bacterial vaginitis)

Firmicutes

Firmicutes are usually described as low G+C gram-positive Eubacteria, but they also include Eubacteria that lack a cell wall (e.g., *Mycoplasma*)

Class: Bacilli
order: Lactobacillales
family: Streptococcaceae
*Streptococcus pyogenes* Rosenbach 1884 (Lancefield Group A; β-hemolytic) (scarlet fever, erysipelas, rheumatic fever, pharyngitis, cellulitis)
*Streptococcus agalactiae* Lehmann and Neumann 1896 (Lancefield Group B; β-hemolytic) (sepsis of the newborn)
*Streptococcus dysgalactiae* group
*S. dysgalactiae* Diernhofer 1932
*S. equi* Sand and Jensen 1888 (includes *S. equi zooepidemicus*)
*Streptococcus equinus* Andrewes and Horder 1906 (aka *S. bovis*; γ-hemolytic)
*Streptococcus canis* Devriese et al. 1986
*Streptococcus pneumoniae* (*Micrococcus pneumoniae* Klein 1884) Chester 1901 (α-hemolytic); pneumococcal infection)
*Streptococcus viridans* group (α-hemolytic or nonhemolytic)
*S. mitis* Andrewes and Horder 1906
*S. mutans* Clarke 1924
*S. oralis* Bridge and Sneath 1982
*S. sanguinis* White and Niven 1946
*S. sobrinus* Coykendall 1974
*Streptococcus milleri* group (Lancefield Group F)
*S. anginosus* Andrewes and Horder 1906
*S. constellatus* (*Diplococcus constellatus* Prevot 1924) Holdeman & Moore 1974
*S. intermedius* Prevot 1925
family: Enterococcaceae
*Enterococcus faecalis* (*Streptococcus faecalis* Andrewes and Horder 1906) Schleifer & Kilpper-Balz 1984 (γ-hemolytic)
*Enterococcus faecium* (*Streptococcus faecium* Orla-Jensen 1919) Schleifer & Kilpper-Bälz 1984 (γ-hemolytic; vancomycin-resistant *enterococcus*)
order: Bacillales
family: Staphylococcaceae
*Staphylococcus aureus* Rosenbach 1884 (cellulitis, Staphylococcal scalded skin syndrome, toxic shock syndrome, food poisoning)
*Staphylococcus epidermidis* (*Albococcus epidermidis* Winslow & Winslow 1908) Evans 1916
*Staphylococcus saprophyticus* Fairbrother 1940 (urinary tract infection)
family: Bacillaceae
*Bacillus anthracis* Cohn 1872 (anthrax)
*Bacillus cereus* Frankland & Frankland 1887 (food poisoning)
family: Listeriaceae
*Listeria monocytogenes* (*Bacterium monocytogenes* Murray et al. 1926) Pirie 1940 (Listeriosis)

Class: Clostridia
order: Clostridiales
family: Clostridiaceae
*Clostridium botulinum* (*Bacillus botulinus* van Ermengem 1896) Bergey et al. 1923 (botulism)
*Clostridium difficile* (*Bacillus difficilis* Hall & O'Toole 1935) Prevot 1938 (pseudomembranous colitis)
*Clostridium perfringens* (*Bacillus perfringens* Veillon & Zuber 1898) Hauduroy et al. 1937 (gas gangrene, clostridial necrotizing enteritis)
*Clostridium tetani* (*Bacillus tetani* Flügge 1886) Bergey et al. 1923 (tetanus)
family: Peptostreptococcaceae
*Peptostreptococcus* sp.

Class: Mollicutes

This group of eubacteria is characterized by the absence of a cell wall (aphragmabacteria). They were previously classified as Tenericutes, a sister group to Firmicutes, before being reassigned as a class within Firmicutes.

order: Mycoplasmatales
family: Mycoplasmataceae
*Mycoplasma genitalium* Tully et al., 1983
*Mycoplasma pneumoniae* Somerson et al., 1963 (mycoplasmal pneumonia, primary atypical pneumonia)
*Mycoplasma arthriditis*
*Mycoplasma fermentans*
*Ureaplasma urealyticum* Shepard et al., 1974 (*Ureaplasma* infection, urethritis)
order: Anaeroplasmatales (or Erysipelotrichales)
family: Erysipelotrichaceae
*Erysipelothrix rhusiopathiae* (*Bacterium rhusiopathiae* Migula 1900) Buchanan 1918 (erysipeloid)
order: Acholeplasmatales
family: Acholeplasmataceae
*Acholeplasma axanthum*
*Acholeplasma brassicae*
*Acholeplasma cavigenitalium*
*Acholeplasma entomophilum*
*Acholeplasma equifetale*
*Acholeplasma florum*
*Acholeplasma granularum*

*Acholeplasma hippikon*
*Acholeplasma laidlawii*
*Acholeplasma modicum*
*Acholeplasma morum*
*Acholeplasma multilocale*
*Acholeplasma oculi*
*Acholeplasma palmae*
*Acholeplasma parvum*
*Acholeplasma pleciae*
*Acholeplasma seiffertii*
*Acholeplasma vituli*
Bacteroidetes
Class: Bacteroidetes
order: Bacteroidales
family: Bacteroidaceae
*Bacteroides fragilis* (*Bacillus fragilis* Veillon and Zuber 1898) Castellani and Chalmers 1919
family: Porphyromonadaceae
*Tannerella forsythia* (*Bacteroides forsythus* Tanner et al. 1986) Sakamoto et al. 2002
*Porphyromonas gingivalis* (*Bacteroides gingivalis* Coykendall et al. 1980) Shah and Collins 1988
family: Prevotellaceae
*Prevotella intermedia* (*Bacteroides melaninogenicus intermedius* Holdeman and Moore 1970) Shah and Collins 1990
Class: Flavobacteria
order: Flavobacteriaceae
family: Flavobacteriales
*Capnocytophaga canimorsus* Brenner et al. 1990
Chlamydiae
order: Chlamydiales
family: Chlamydiaceae
*Chlamydia trachomatis* (*Rickettsia trachomas* Busacca 1935) Rake 1957 (lymphogranuloma venereum, trachoma)
*Chlamydophila psittaci* (*Rickettsia psittaci* Lillie 1930) Everett et al. 1999 (psittacosis)
*Chlamydophila pneumoniae* (*Chlamydia pneumoniae* Grayston et al. 1989) Everett et al. 1999
Fusobacteria
order: Fusobacteriales
family: Fusobacteriaceae
*Fusobacterium necrophorum* (*Bacillus necrophorus* Flugge 1886) Moore and Holdeman 1969 (Lemierre's syndrome)
*Fusobacterium nucleatum* (*Bacillus fusiformis* Veillon and Zuber 1898) Knorr 1922
*Fusobacterium nucleatum nucleatum* Knorr 1922
*Fusobacterium nucleatum polymorphum* (*Fusobacterium polymorphum* Knorr 1922) Dzink et al. 1990
*Streptobacillus moniliformis* (*Streptothrix muris ratti* Schottmuller 1914) Levaditi et al. 1925 (*Actinobacillus muris* Wilson and Miles 1955; rat bite fever)
Proteobacteria
Class: Alpha Proteobacteria
order: Rickettsiales
family: Rickettsiaceae
*Rickettsia*—spotted fever group
*Rickettsia rickettsii* (*Dermacentroxenus rickettsii* Wolbach 1919) Brumpt 1922 (Rocky Mountain spotted fever)
*Rickettsia conorii* Brumpt 1932 (Boutonneuse fever)
*Rickettsia akari* Huebner et al. 1946 (rickettsial pox)
*Rickettsia*—typhus group
*Rickettsia typhi* (*Dermacentroxenus typhi* Wolbach and Todd 1920) Philip 1943 (murine typhus)
*Rickettsia prowazekii* da Rocha-Lima 1916 (epidemic typhus)
*Orientia tsutsugamushi* (*Theileria tsutsugamushi* Hayashi 1920) Tamura et al. 1995 (scrub typhus)
family: Anaplasmataceae (or Ehrlichiaceae) (Ehrlichiosis and Anaplasmosis)
*Anaplasma phagocytophilum* (*Rickettsia phagocytophila ovis* Foggie 1949) Dumler et al. 2001 (human granulocytic ehrlichiosis)
*Ehrlichia chaffeensis* Anderson et al. 1992 (human monocytic ehrlichiosis)
order: Rhizobiales
family: Brucellae
*Brucella abortus* (*Bacterium abortus* Schmidt 1901) Meyer and Shaw 1920 (Brucellosis)
family: Bartonellae
*Bartonella bacilliformis* (*Bartonia bacilliformis* Strong et al. 1913) Strong et al. 1915 (Carrion's disease)
*Bartonella henselae* (*Rochalimaea henselae* Regnery et al. 1992) Brenner et al. 1993 (cat scratch fever; bacillary angiomatosis)
*Bartonella quintana* (*Rickettsia quintana* Schmincke 1917) Brenner et al. 1993 (trench fever; bacillary angiomatosis)
Class: Beta Proteobacteria
order: Neisseriales
family: Neisseriaceae
*Neisseria meningitidis* (*Micrococcus meningitidis cerebrospinalis* Albrecht & Ghon 1901) Murray 1929 (meningococcal disease, Waterhouse-Friderichsen syndrome)
*Neisseria gonorrhoeae* (*Merismopedia gonorrhoeae* Zopf 1885) Trevisan 1885 (gonorrhea)
*Eikenella corrodens* (*Bacteroides corrodens* Eiken 1958) Jackson and Goodman 1972
*Kingella kingae* (*Moraxella kingii* Henriksen and Bovre 1968) Henriksen and Bovre 1976
order: Burkholderiales
family: Burkholderiaceae
*Burkholderia pseudomallei* group
*B. pseudomallei* (*Bacillus pseudomallei* Whitmore 1913) Yabuuchi et al. 1993 (aka *Pseudomonas pseudomallei* Haynes 1957; melioidosis)
*B. mallei* (*Bacillus mallei* Zopf 1885) Yabuuchi et al. 1993 (aka *Pseudomonas mallei* Redfearn et al. 1966; glanders)
*Burkholderia cepacia* complex
*B. cepacia* (*Pseudomonas cepacia* Burkholder 1950) Yabuuchi et al. 1993
*B. vietnamiensis* Gillis et al. 1995
*B. multivorans* Vandamme et al. 1997
*B. stabilis* Vandamme et al. 2000
*B. ambifaria* Coenye et al. 2001
*B. anthina* Vandamme et al. 2002
*B. cenocepacia* Vandamme et al. 2003
*B. dolosa* Vermis et al. 2004
*B. pyrrocinia* (*Pseudomonas pyrrocinia* Imanaka et al. 1965) Vandamme et al. 1997
family: Alcaligenaceae Bordetella pertussis (*Hemophilus pertussis* Bergey et al. 1923) Moreno-Löpez 1952 (pertussis or whooping cough)

*Bordetella parapertussis* (*Bacillus parapertussis* Eldering and Kendrick 1938) Moreno-López 1952 (*parapertussis*)

Family: Ralstoniaceae

*Ralstonia basilensis*

*Ralstonia campinensis*

*Ralstonia eutropha*

*Ralstonia gilardii*

*Ralstonia insidiosa*

*Ralstonia mannitolilytica*

*Ralstonia metallidurans*

*Ralstonia paucula*

*Ralstonia pickettii*

*Ralstonia respiraculi*

*Ralstonia solanacearum*

*Ralstonia syzygii*

*Ralstonia taiwanensis* order: Nitrosomonadales family: Spirillaceae

*Spirillum minus* (Rat-bite fever)

Class: Gamma Proteobacteria order: Enterobacteriales family: Enterobacteriaceae

*Enterobacter cloacae* (*Bacillus cloacae* Jordan 1890) Hormaeche and Edwards 1960

*Escherichia coli* (*Bacillus coli* Migula 1895) Castellani and Chalmers 1919

*Klebsiella granulomatis* (*Calymmatobacterium granulomatis* Arago & Vianna 1913) Carter et al. 1999 (granuloma inguinale or donovanosis)

*Klebsiella oxytoca* (*Bacillus oxytocus perniciosus* Flügge 1886) Lautrop 1956

*Klebsiella pneumoniae* (*Hyalococcus pneumoniae* Schroeter 1886) Trevisan 1887 (rhinoscleroma, *Klebsiella pneumonia*)

*Plesiomonas shigelloides* (*Pseudomonas shigelloides* Bader 1954) Habs and Schubert 1962 (aka *Aeromonas shigelloides* Ewing et al. 1961)

*Proteus mirabilis* Hauser 1885

*Proteus vulgaris* Hauser 1885

*Salmonella enterica* (*Bacillus cholerae-suis* Smith 1894) Kauffmann & Edwards 1952 (typhoid fever, paratyphoid fever, *Salmonellosis*)

*Serratia marcescens* Bizio 1823 (*Serratia* infection)

*Shigella dysenteriae* (*Bacillus dysentericus* Shiga 1897) Castellani & Chalmers 1919 (Shigellosis, bacillary dysentery)

*Shigella flexneri* Castellani & Chalmers 1919 (Shigellosis, bacillary dysentery)

*Shigella sonnei* (*Bacterium sonnei* Levine 1920) Weldin 1927 (Shigellosis, bacillary dysentery)

*Yersinia enterocolitica* (*Bacterium enterocoliticum* Schleifstein & Coleman 1939) Frederiksen 1964

*Yersinia pestis* (*Bacterium pestis* Lehmann & Neumann, 1896) van Loghem 1944 (aka *Pasteurella pestis* Bergey et al. 1923; plague/bubonic plague)

*Yersinia pseudotuberculosis* (*Bacillus pseudotuberkulosis* Pfeiffer 1889) Smith & Thal 1965 order: Cardiobacteriales family: Cardiobacteriaceae

*Cardiobacterium hominis* Slotnick and Dougherty 1964 order: Legionellales family: Legionellaceae

*Legionella pneumophila* Brenner et al. 1979 (Legionellosis)

*Legionella longbeachae* McKinney et al. 1982 (Legionellosis)

family: Coxiellaceae

*Coxiella burnetii* (*Rickettsia burneti* Derrick 1939) Philip 1948 (Q fever)

order: Pasteurellales family: Pasteurellaceae

*Haemophilus influenzae* (*Bacterium influenzae* Lehmann & Neumann 1896) Winslow et al. 1917 (*Haemophilus* meningitis, Brazilian purpuric fever)

*Haemophilus ducreyi* (*Bacillus ukeris cancrosi* Kruse 1896) Bergey et al. 1923 (chancroid)

*Pasteurella multocida* (*Bacterium multocidum* Lehmann and Neumann 1899) Rosenbusch and Merchant 1939 (Pasteurellosis)

*Actinobacillus ureae* (*Pasteurella ureae* Jones 1962) Mutters et al. 1986 (Actinobacillosis)

*Actinobacillus hominis* Friis-Mller 1985 (Actinobacillosis)

*Aggregatibacter actinomycetemcomitans* (*Bacterium actinomycetemcomitans* Klinger 1912) Norskov-Lauritsen and Kilian 2006 (aka *Actinobacillus actinomycetemcomitans* Topley and Wilson 1929)

order: Pseudomonadales family: Pseudomonadaceae

*Pseudomonas aeruginosa* (*Bacterium aeruginosum* Schröter 1872) Migula 1900 (*Pseudomonas* infection)

family: Moraxellaceae

*Moraxella catarrhalis* (*Mikrokkokus catarrhalis* Frosch and Kolle 1896) Henriksen and Bovre 1968 (aka *Branhamella catarrhalis* Catlin 1970)

*Acinetobacter baumannii* Bouvet and Grimont 1986 order: Thiotrichales family: Francisellaceae

*Francisella tularensis* (*Bacterium tularense* McCoy and Chapin 1912) Dorofe'ev 1947 (tularemia)

order: Vibrionales family: Vibrionaceae

*Vibrio cholerae* Pacini 1854 (cholera)

*Vibrio vulnificus* (*Beneckea vulnifica* Reichelt et al. 1979) Farmer 1980

*Vibrio parahaemolyticus* (*Pasteurella parahaemolytica* Fujino et al. 1951) Sakazaki et al. 1963 (aka *Beneckea parahaemolytica* Baumann et al. 1971)

order: Xanthomonadales family: Xanthomonadaceae

*Stenotrophomonas maltophilia* (*Pseudomonas maltophilia* Hugh and Ryschenkow 1961) Palleroni & Bradbury 1993

Class: Epsilon Proteobacteria order: Campylobacterales family: Campylobacteraceae

*Campylobacter jejuni* (*Vibrio jejuni* Jones et al. 1931) Veron & Chatelain 1973 (Campylobacteriosis)

*Campylobacter coli* (*Vibrio coli* Doyle 1948) Veron and Chatelain 1973

*Campylobacter lari* (*Campylobacter laridis* Benjamin et al. 1983) Benjamin et al. 1984

*Campylobacter fetus* (*Vibrio fetus* Smith and Taylor 1919) Sebald and Veron 1963 family: Helicobacteraceae

*Helicobacter pylori* (*Campylobacter pyloridis* Marshall et al. 1985) Goodwin et al. 1989 (peptic ulcer)

*Helicobacter cinaedi* (*Campylobacter cinaedi* Totten et al. 1988) Vandamme et al. 1991

*Helicobacter fennelliae* (*Campylobacter fennelliae* Totten et al. 1988) Vandamme et al. 1991

Spirochaetes order: Spirochaetales family: Spirochaetaceae

*Treponema pallidum* (*Spirochaeta pallida* Schaudinn and Hoffmann 1905) Schaudinn 1905

*Treponema pallidum pallidum* (syphilis)

*Treponema pallidum endemicum* (bejel)

*Treponema pallidum pertenue* (yaws)

*Treponema carateum* (pinta)

*Treponema denticola* (*Spirochaete denticola* Flugge 1886) Chan et al. 1993

*Borrelia recurrentis* (*Spirochaete recurrentis* Lebert 1874) Bergey et al. 1925 (relapsing fever)

*Borrelia burgdorferi* Johnson et al. 1984 (Lyme disease, erythema chronicum migrans, neuroborreliosis)

family: Leptospiraceae

*Leptospira interrogans* (*Spirochaeta interrogans* Stimson 1907) Wenyon 1926 (leptospirosis)

In certain aspects, the disclosed system and methods are used to analyze a dental sample and any of the following organism genera may be detected: *Bacteroides, Tannerella, Prevotella, Peptostreptococcus, Streptococcus, Staphylococcus, Porphyromonas, Fusobacterium, Clostridium, Treponema, Atopobium, Cryptobacterium, Eubacterium, Mogibacterium, Filifactor, Dialister, Centipeda, Selenomonas, Granulicatella*, and *Kingella* and/or other bacteria, viruses, fungi, and/or protozoa. A "dental sample" may comprise a tooth, a soft tissue, and/or dental pulp.

In other aspects, the disclosed system and methods are used to analyze a joint sample and any of the following organism genera may be detected: *Staphylococcus, Streptococcus, Kingella, Aeromonas, Mycobacterium, Actinomyces, Fusobacterium, Salmonella, Haemophilus, Borrelia, Neisseria, Escherichia, Brucella, Pseudomonas, Mycoplasma, Salmonella, Propionibacterium, Acinetobacter, Treponema*, and *Erysipelothrix* and/or other bacteria, viruses, fungi, and/or protozoa. A "joint sample" may comprise tissue and/or fluid (e.g., synovial fluid) removed from a joint.

In yet other aspects, the disclosed system and methods are used to analyze a blood, sample and any of the following organism genera may be detected: *Capnocytophaga, Rickettsia, Staphylococcus, Streptococcus, Neisseria, Mycobacterium, Klebsiella, Haemophilus, Fusobacterium, Chlamydia, Enterococcus, Escherichia, Enterobacter, Proteus, Legionella, Pseudomonas, Clostridium, Listeria, Serratia*, and *Salmonella* and/or other bacteria, viruses, fungi, and/or protozoa. A "blood sample" may comprise blood, serum, and/or plasma.

Certain microorganisms are "nonculturable" pathogens. As used herein, the term "nonculturable" refers to microorganisms that are alive but do not produce visible colonies on classical liquid or solid media (e.g., Luria Broth, thioglycollate broth, blood culture, etc.) within 96 hours after inoculation at about 30° C. under aerobic or anaerobic conditions. Examples of such nonculturable microorganisms are *Bartonella henselae*, the causative agent of bacillary angiomatosis; *Tropheryma whipplei*, the etiologic agent in Whipple's disease; and *Bartonella quintana* and *Coxiella burnetii*, which are both associated with endocarditis. Exemplary methods of the present disclosure may be used to identify such nonculturable pathogens in a biological sample.

Exemplary methods of the present disclosure may also be used to identify a "pathogenic community of microorganisms." As used herein, a "pathogenic community of microorganisms" is a group of microorganisms where the individuals are not pathogenic but together they constitute an invasive, pathogenic population. The study of population-level virulence traits among communal bacteria represents an emerging discipline in the field of bacterial pathogenesis. It has become clear that bacteria exhibit many of the hallmarks of multicellular organisms when they are growing as biofilms and communicating among each other using quorum-sensing systems. Each of these population-level behaviors provides for multiple expressions of virulence that individual free-swimming bacteria do not possess. Population-level virulence traits are often associated with chronic or persistent infections, whereas individual bacterial virulence traits are generally associated with acute infections.

In certain aspects, the present disclosure provides a method and kit that qualifies as a high complexity test under CLIA guidelines and may be validated as a Laboratory Developed Test (LDT). As an LDT, the diagnostic system and methods may be required to meet several compliance guidelines regarding accuracy, validity, and performance parameters.

In certain aspects, the following control checks are in place for the disclosed system and methods:

Run-to-Run Controls

Sample Quality—The quality and quantity of received samples are scrutinized for visible signs of contamination or other concerns that would preclude processing. Hemolyzed blood samples, clearly contaminated tissues or fluids, and inappropriately shipped or stored samples are rejected from analysis.

DNA Extraction—DNA is extracted from the submitted samples and the total recovered DNA content is analyzed for concentration and purity. If a minimum of about 5 ng/μL total DNA concentration is not obtained analysis may not be performed as the quantity or quality of the provided sample may not be sufficient. Furthermore, the 260λ/280λ and 260λ/230λ ratios are observed to assess for contaminating proteins or other potential inhibitors.

Molecular Tagging and Amplification—DNA amplification reactions are performed in parallel with negative amplification controls for each patient sample and with a master positive control of a known microbial sample from the ATCC bioresource bank. The positive control species is rotated for each run ensuring continual efficacy across multiple species. The positive control samples from each tagging and amplification run are carried forward with the accompanying patient samples and analyzed to ensure amplification through reporting generates the properly identified bacterium. Lastly, the resulting DNA is purified and again analyzed for purity and concentration prior to entering into the sequencing protocols.

Next Generation DNA Sequencing—The sequencing reactions are preferably monitored and filtered by several overlapping control procedures at both the analysis and sequencing level. In certain implementations, first, the DNA fragments are linked to Ion Sphere Particles (ISPs) using a controlled concentration to yield the highest resulting monoclonal ISP/DNA population. The efficiency of labeling the ISPs may be assayed using fluorescent probes whereby the ratios of leading and trailing sequences are measured and the ratios compared. In some aspects, initial labeling must surpass about 10% prior to ISP enrichment. Enrichment consistently raises the ISP labeled monoclonal ISP level to greater than about 80%, thus ensuring sufficient DNA reads for proper analysis. In addition to controlling for the proper template and ISP assembly the sequencing reaction itself must be controlled. The semiconductor chip is automatically tested by the system hardware to ensure this consumable is working properly. Next, the sequencing reaction chemistry is assayed for performance by the addition of control ISPs into the generated DNA library. Problems with sequencing efficiency, noise, chemistry, or contamination may be determined by observing the results from the control ISPs. Finally, the chip loading and performance is analyzed by the end of the run to identify any problems resulting from any of the preceding preparation steps. The resulting quality and number of sequence reads should preferably surpass expected parameters to be acceptable for analysis depending on the semiconductor chip size selected for the test run.

Bioinformatics Analysis—In certain implementations, the bioinformatics analysis is entirely computer executed with minimal human input or guidance, thus minimizing operator induced errors during the complex mathematical analysis of the resulting DNA sequence information. Resulting sequence reads that do not meet specific quality requirements are preferably removed prior to analysis. Subsequent DNA sequences may be identified independently using internationally curated databases and the closes matches are selected. Depending on the resulting strength of the identification the best match for each sequence is recorded and collated. The top result matches can meet additional quality metrics prior to being accepted as legitimate results. Furthermore, non-target DNA sequences such as human contaminants can be screened out. Finally, the most significant and highest probability results can be presented for report building. Using these methods the genus can be correctly identified greater than about 60%, about 65%, about 70%, about 75%, about 80%, about 85%, about 90%, or about 95% of the time, while the specific species may be correctly identified greater than about 20%, about 25%, about 30%, about 35%, about 40%, about 45%, about 50%, about 55% about 60%, about 65%, about 70%, about 75%, about 80%, about 85%, about 90%, or about 95% of the time. Treatment recommendations may be presented based on literature searches across the identified genus and/or species. Samples that fail to meet these requirements can be rejected from analysis as, for example, a "No Significant Sequences Detected" result.

Result Report Building—Lastly, both a sequencing technician and the Laboratory Director may review the resulting data prior to result reporting. Reports can be scrutinized for evidence of contamination, carryover, or failure of control parameters. Once these criteria are met, the reports may be released to physicians or healthcare providers as, for example, a password protected PDF document.

System Validity

In addition to run-to-run performance controls listed above the disclosed system and methods have undergone significant validation for identification of naturally occurring and synthetic bacterial populations in a variety of sample types. For each pooled patient DNA library a known microorganism slated for identification can be included and the assay can be partially perpetually validated with the appropriate identification of the included positive control species. The source material for these cells or DNA may be provided from the American Type Culture Collection (ATCC) bioresource catalogue of well-studied and characterized standards. The selected control species include and rotate through known pathogens such as *Borrelia burgdorferi, Mycoplasma arthriditis, Escherichia coli, Bartonella henselae, Coxiella brunetii*, and *Bartonella bacilliformis*. Additionally, the performance metrics for the assay are selected to provide the most accurate picture of organism ratios in a given sample. Simply, known combinations of organisms have been generated, and the best quality cutoffs to best replicate actual DNA contribution from mixed populations have been determined. In addition to single or combinatorial validation, a large number of real world samples from a variety of sources have been processed. These include blood samples, tissue biopsies, synovial fluid, serum, cerebrospinal fluid, abscess material, and even dental infections. As expected the detected microbial populations reflect and are in congruence with previously published microbial populations appropriate for the sample type; however, as also expected the identified ratios and specific bacterial contributors vary from sample to sample with unique and identifying characteristics. Furthermore, dental abscesses have been identified having the main contributors from both the *Streptococcus* and *Staphylococcus* genera consistent with published expected results.

In some implementations, reports are distributed the day after a successful sequencing run and may include the following information.

Page 1

1. Patient, physician, and other pertinent test information is presented at the top of the report for convenience in line with standard laboratory reports.
2. A bar graph displaying, for example, up to 6 of the top significant microbial species or microbials identified by the sequence analysis. This bar graph takes into account the strength of the identified result. DNA sequences of which a high probability match are found can be indicated as "Close Match" and can be represented as a solid bar, while DNA sequences that are divergent but are the closest match to the organism can be indicated as a "Potential Novel" and can be represented, for example, as a hatched bar on the graph. The relative percent contribution is indicated underneath the bar graph for easy reference.
3. A table of, for example, up to 6 of the top significant identified species including Genus specific treatments (e.g., antibiotics, antifungals, antivirals, or antiprotozoals) and any noted treatment resistance for organisms in that Genus. It is important to note that these are not drug sensitivities derived from sequence information, but literature derived suggestions as to what therapies show efficacy in vivo or in vitro. Furthermore, treatments for the Genus may also show up in the noted resistance column, as the results are not mutually exclusive.
4. A following Notes section can include performance characteristics of this assay both general and specific to the submitted sample.

Page 2+

5. The first section on Page 2 can include a complete listing of the all of the significant identified microbes including total sequence counts and percentages in addition to "Close Match" and "Potential Novel" counts and percentages. These may exceed the total of 6 organisms presented in the bar graph on Page 1.
6. Finally detailed treatment susceptibility with references can be listed for each identified Genus and can be ordered in the order of contribution to the sample. This allows for easy reference to confirm or obtain detailed information about previous literature studying the susceptibility of various bacterial Genera. This section may extend for several pages of detailed reference information.

In certain aspects, the present disclosure provides kits for the identifying a plurality of microorganisms in a biological sample. Exemplary kits includes a) at least one forward primer comprising an adapter sequence and a priming sequence, for a target sequence, wherein the target sequence comprises a sequence from a characteristic gene sequence; and b) at least one reverse primer.

The kits may be used with an ion semiconductor sequencing platform. The kits may comprise any of the primers disclosed herein, for example but limited to, a forward primer comprising a barcode, a barcode adapter, and a target sequence comprising a sequence from the 16S rRNA gene. The kit may also comprise nucleotides, buffers and/or a DNA polymerase.

Figure 12:
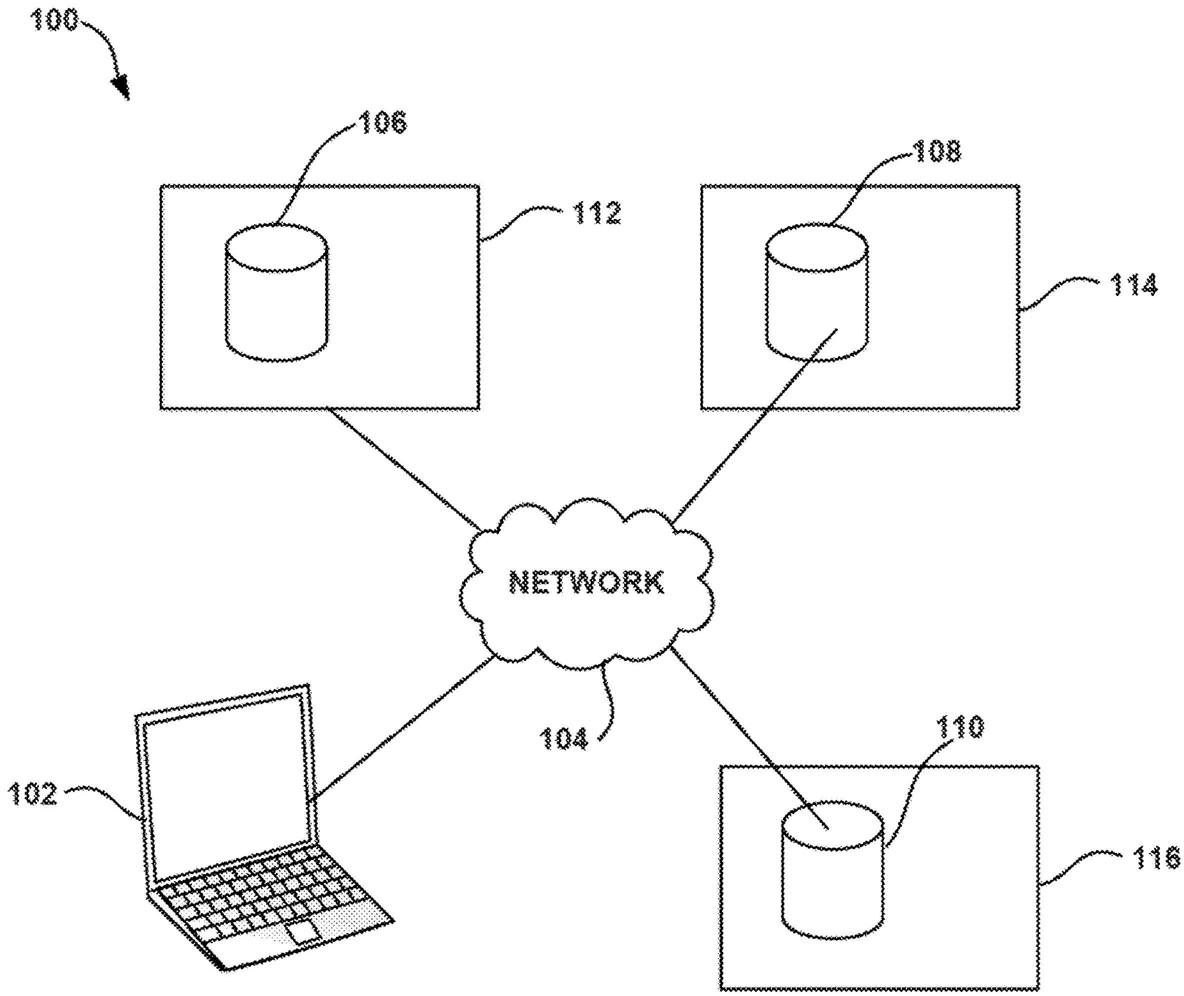
FIG. 12 illustrates a system in accordance with various embodiments of the disclosure.

Further exemplary embodiments of the disclosure provide systems and methods for characterizing one or more microorganisms that may be utilized on a traditional or mobile computerized interfaces or network capable of providing the disclosed processing, querying, and displaying functionalities. Various examples of the disclosed systems and methods may be carried out through the use of one or more computers, processors, servers, databases, and the like. Various examples disclosed herein provide highly efficient computerized systems and methods for characterizing one or more microorganisms or DNA fragments thereof, such as for example, pathogenic microorganisms in an efficient and timely manner, such that the systems and methods are suitable for use in clinical settings. Exemplary systems and methods can also provide treatment and/or treatment sensitivity information related to the one or more identified microorganism, such that a care provider can use such information. FIG. 12 illustrates a system 100 in accordance with exemplary embodiments of the disclosure. As illustrated, system 100 includes a computer 102, which can be connected to a network 104. System 100 can also include one or more databases 106-110, which may form part of one or more servers, such as servers 112-116. Although illustrated as part of separate servers, databases 106-110 can form part of the same server or part of a computer, such as computer 102 or another computer.

Computer 102 can include any suitable devices that performs the computer functions noted below. For example, computer 102 can be or include a desktop computer, notebook computer, workstation, network computer, personal data assistant, minicomputer, mainframe computer, server, supercomputer, mobile device, a wearable computer, a sequencing (e.g., DNA sequencing) device, or other device having suitable computing capabilities.

Network 104 can be or include a local area network (LAN), a wide area network, a personal area network, a campus area network, a metropolitan area network, a global area network, or the like. Network 104 can be coupled to one or more computers 102, servers 112-116, other networks, and/or other devices using an Ethernet connection, other wired connections, a WiFi interface, other wireless interfaces, or other suitable connection.

Servers 112-116 can include any suitable computing device, including devices described above in connection with computer 102. Similarly, databases 106-110 can include any suitable database, such as those described in more detail below.

Figure 13:
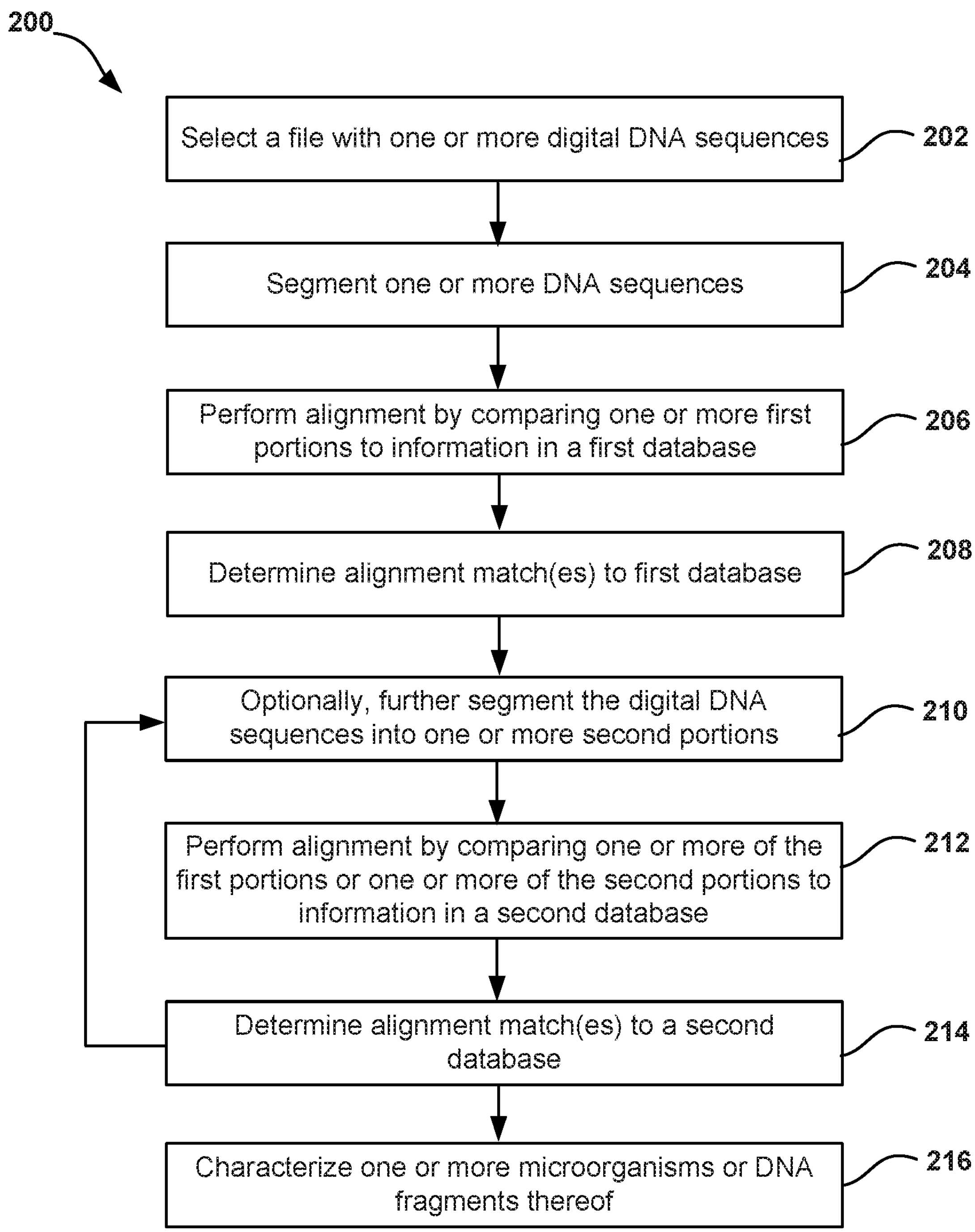
FIG. 13 illustrates a method in accordance with exemplary embodiments of the disclosure.

FIG. 13 illustrates a method 200 of characterizing one or more microorganisms in accordance with various examples of the disclosure. Method 200 includes the steps of selecting, by a computer, a digital file comprising one or more digital DNA sequences, wherein each of the one or more digital DNA sequences corresponds to a microorganism to be characterized (step 202); segmenting, by the computer, each of the one or more digital DNA sequences into one or more first portions (step 204); performing, by the computer, a set of alignments by comparing the one or more first portions to information stored in a first database (step 206); determining, by the computer, sequence portions from among the one or more first portions that have an alignment match to the information stored in the first database (step 208); optionally further segmenting, by the computer, each of the one or more digital DNA sequences into one or more second portions (step 210); performing, by the computer, a set of alignments by comparing the one or more first portions or the one or more second portions to information stored in a second database (step 212); determining, by the computer, sequence portions from among the one or more first portions or the one or more second portions that have an alignment match to the information stored in the second database (step 214); and characterizing one or more microorganisms or DNA fragments thereof based on the alignment match to the information stored in one or more of the first database and the second database (step 216). Each of the steps can be performed using, for example, computer 102 of system 100.

Figure 14:
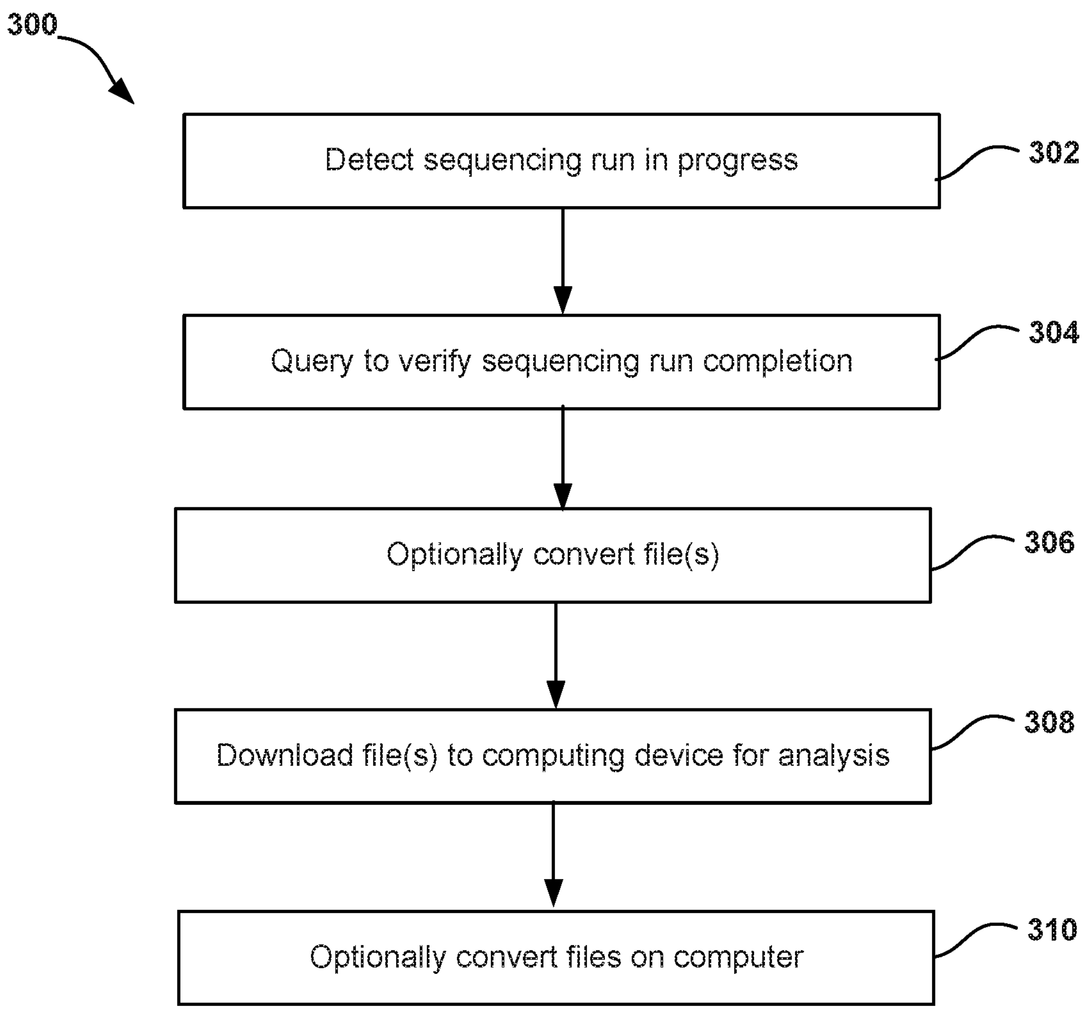
FIG. 14 illustrates a method for automatic sequencing run acquisition in accordance with further exemplary embodiments of the disclosure.

In accordance with some examples of these embodiments, method 200 may also include a step of automatically detecting a sequence run prior to step 202. FIG. 14 illustrates an exemplary sequence run and detection process 300 suitable for use with method 200 and for method 400, described below. In a situation in which a genetic sequencing run is in progress, an in-progress run may be detected—e.g., by a computer (step 302). In response to the detection, the computer may query, for example, a server (e.g., on of servers 112-116) or other computing device on which the sequencing process is occurring to verify completion of the sequencing run (step 304). While it is contemplated that any appropriate file format may be used, in some implementations, the processed sequence file may optionally be converted from one format to another (step 306). For example, an original file may be in a BAM format which can then be converted to a FASTQ file format for further processing and/or data manipulation. Alternatively, the processed sequence file may be in an SFF, FASTQ, or any other appropriate format that is convertible to a FASTQ file format. The file(s) can then be downloaded or otherwise transferred to a computing device for further analysis (step 308), such as for use with method 200. Alternatively, method 200 can employ a sequence file that is, e.g., in FASTQ or other appropriate format from a previously completed sequencing run. Regardless of whether a file is manually selected by a user or automatically detected by the computing device in accordance with FIG. 3, an implementation of the method may then convert the FASTQ or other file format into one or more easily usable FASTA formatted or other appropriately formatted files, illustrated as step 310 in FIG. 3. During step 310, during the file conversion, the sequencing device type and/or the microorganism type can be detected. This allows the method (e.g., method 200 or 400) to automatically process the sequences based on an incoming data (e.g., for a sequencer type) and/or microorganism type.

Referring again to FIG. 13, during step 202, a digital file comprising one or more digital DNA sequences is selected.

The digital file can include a plurality of DNA sequences from the one or more files (e.g., FASTA files) that can comprise a predetermined number of base pairs (bp) or otherwise have a predetermined length. In some implementations, 100 bp may be a preferred number of base pairs at which to set this selection threshold, however, any other number of base pairs that allows for adequate processing and elimination of sequence portions that are unlikely to lead to meaningful analysis may also be selected. For example, greater than or equal to 50 bp, 100 bp, or 150 bp may be used.

During step 204, the selected DNA sequence file(s) are segmented into one or more first portions, which may be of equal size or length. While any number of (e.g., equal) portions may be used, in some implementations, it may be desirable to match the number of portions to the number of processing cores to be used by a system for processing. For example, when using an analysis computer that has 32 cores, it may be desirable to use 30 of those cores for processing while keeping the remaining two cores in reserve for data management and other processing functions. By way of particular example, it may then be preferable to divide the (e.g., FASTA) sequence file into 30 equal portions, such that one portion of the file may be processed by each desired processing core.

Once the division of one or more digital DNA sequences into one or more first portions is complete, a set of alignments is performed by comparing the one or more first portions to information stored in a first database (step 206). The alignments can be performed using a variety of techniques, including Basic Local Alignment Search Tool (BLAST), OTU, G-BLASTN, mpiBLAST, BLASTX, PAUDA, USEARCH, LAST, BLAT, or other suitable technique.

The first database (e.g., one of databases 106-110) can include a database that includes nucleic acid information (e.g., DNA and/or RNA information) corresponding to one or more types of microorganism—e.g., bacteria, viruses, protozoa, or fungi. By way of examples, the first database can include a bacterial nucleic acid database, such as an 16S Microbial DNA Database.

By way of particular examples, step 206 can include performing a set of alignments using BLAST by comparing each of the sequence file portions to a say a DNA database of 16S rRNA Microbial sequences (Bacteria and Archaea) (hereinafter referred to as "16S") database, such as the National Center for Biotechnology Information (NCBI) 16S database.

The alignments may in some implementations occur substantially simultaneously. It may also be preferable to perform the alignments during step 206 using a relatively small comparison window (e.g., 10 bp or 11 bp) as the first database may be relatively small and thus, the processing time does not become prohibitive even with relatively small comparison windows. Although not illustrated, method 200 can include collating the aggregate results and eliminating any duplicates present. This may be done, for example, when the alignments are complete at step 206.

During step 208, a computer determines sequence portions from among the one or more first portions that have an alignment match to the information stored in the first database. The step of determining may be based on a predetermined criteria or tolerance for a match.

During step 210, each of the one or more digital DNA sequences from step 202 are optionally further segmented into one or more second portions. Step 210 can be performed in substantially the same way as step 204. During this optional step, the sequence files can be divided into a second plurality of sequence portions, which may be of equal size and/or the number of portions may be determined by a preferred number of processing cores to be used. In accordance with some exemplary embodiments, the second portions differ or are exclusive of the first portions.

During step 212, a set of alignments by comparing the one or more first portions or the one or more second portions (if optional step 210 is performed) to information stored in a second database is performed. Step 212 is similar to step 206, except either first portions or second portions are compared to a second database.

The second database may be relatively large relative to the first database. As such, to reduce processing time, it may be desirable to use a comparison window that is relatively large (e.g., 65 bp, 100 bp, or the like), especially for a first run of step 212. The second database can be or include, for example, a comprehensive nucleic acids database, such as a comprehensive DNA database, a comprehensive RNA database, a eukaryotic DNA database, an NT database, a fungi DNA database, a protozoa DNA database, a comprehensive bacterial nucleic acids database, or a viral nucleic acids database.

As shown in FIG. 13, steps 210-214 can be repeated—e.g., in an iterative manner, wherein a comparison window for determining a match decreases as the number (n) of runs increases. For example, the initial comparison window size can start at 65 bp, and decrease to 40 bp, 25 bp, 10 bp with subsequent runs.

The alignment results from step 212 can be collated and any duplicates removed. The results can then be checked to determine if all of the sequence file portions were aligned through the running of the alignments.

Step 214 can be performed in a manner similar to or the same as step 208. If the alignments performed on the second portions are done using a large comparison window, the results of these alignments may not produce a match between the sequence of the file portion and the second database, due to the low level of stringency. If there are any of the sequence file portions for which the alignment did not identify a match within the second database, a size of a comparison window can be adjusted (e.g., automatically) to increase the stringency—i.e., decrease a size of a comparison window—of a subsequent alignment. The previously unidentified sequence portions are then passed iteratively back into the file segmentation stage 210 where they may then be segmented into any desired number of (e.g., equally) sized sequence portions and alignments are then run for each of the portions. These steps may be iteratively repeated and the stringency increased (comparison window size decreased) each time step 212 is performed and fails to produce a resulting match in step 214. By starting with a lower stringency (e.g., large comparison window) and increasing the stringency (e.g., decreasing the comparison window)—e.g., in a manner that is directly proportional to the number of times which a portion of the sequence has passed through an alignment and failed to find a match, significant processing time may be saved. For example, beginning with a low stringency having a comparison window of 65 bp and then iteratively increasing the stringency by decreasing the comparison window to, for example, 40 bp, 25 bp, and finally 10 bp rather than simply running all of the second database alignments with a comparison window of 10 bp from the start may reduce processing time by many hours or even days. The method may also utilize a maximum stringency (minimum comparison window size) setting in which any leftover sequence portions that have not resulted in a second database match after having been aligned at the highest designated stringency level are discarded to prevent unnecessary processing from continuing.

Table 1 below illustrates the effect of window size on speed and rate at which sequences are characterized in addition to the ratio of contaminating human sequences vs the target microbial sequences.

TABLE 1

| Comparison Window Size | % Recovery | Time (min) | Human | NonHuman | Seq/Min | %/Min | Human/ Non-Human |
|---|---|---|---|---|---|---|---|
| 200 | 13.4% | 2.7 | 11500 | 57 | 4344.7 | 5.1% | 201.8 |
| 150 | 35.7% | 4.4 | 30538 | 148 | 7022.0 | 8.2% | 206.3 |
| 100 | 63.5% | 4.7 | 54231 | 311 | 11679.2 | 13.6% | 174.4 |
| 90 | 71.9% | 4.7 | 61433 | 376 | 13039.9 | 15.2% | 163.4 |
| 80 | 79.4% | 5.3 | 67848 | 422 | 12832.7 | 14.9% | 160.8 |
| 75 | 85.2% | 4.7 | 72811 | 466 | 15524.8 | 18.1% | 156.2 |
| 70 | 88.6% | 4.8 | 75222 | 920 | 15896.0 | 18.5% | 81.8 |
| 65 | 90.5% | 4.9 | 76724 | 1026 | 15932.4 | 18.5% | 74.8 |
| 64 | 90.8% | 5.0 | 76991 | 1041 | 15606.4 | 18.2% | 74.0 |
| 63 | 91.4% | 5.4 | 77481 | 1064 | 14681.3 | 17.1% | 72.8 |
| 62 | 91.9% | 5.0 | 77917 | 1096 | 15834.3 | 18.4% | 71.1 |
| 60 | 92.6% | 5.8 | 78472 | 1146 | 13822.6 | 16.1% | 68.5 |
| 50 | 96.0% | 5.8 | 81078 | 1460 | 14304.7 | 16.6% | 55.5 |
| 40 | 98.6% | 8.8 | 82945 | 1849 | 9592.1 | 11.2% | 44.9 |
| 25 | 99.9% | 48.7 | 83349 | 2508 | 1763.7 | 2.1% | 33.2 |

At step 216, one or more microorganisms are characterized. The characterization can include identifying the one or more microorganisms or finding a close match of an unknown microorganism to a known or unknown microorganism in a database.

Exemplary methods can also include a comparison of results from the two alignments determination steps 208 and 214. For example, once collation and removal of duplicate results has been accomplished for both the first database alignments results and the second database (optionally iteratively performed) aligned results, the results of the two databases alignments can be compared. In some implementations of the method, the first database alignment results may first be examined to determine if there are any complete, or 100%, matches. If so, these are assumed to be correctly identified microorganisms due to their high degree of matching and can be placed into a first list. The first database results can then re-analyzed to find matches having a slightly lesser degree of completeness, but for which there is still a reasonably high probability that the microorganism has been correctly identified and these results are also added to the first list. For example, the matches can be 100%, 98%, 97%, 95%, or 90%. For the remaining first database results that fall below the predetermined threshold of reliability for the results to become a member of the first list, a comparison can made with the corresponding second database results for each particular sequence portion to determine whether the second database result (e.g., a match during step 214) or the first database result (from step 208) provides a closer match. In some implementation, this may be accomplished by comparing one or more variables, such as for example, one or more of a percentage identity and sequence E-value, to determine which of the two database alignments result in the closest match. Once it is determined which is the closer match, the results can further analyzed to characterize and/or identify any of the closest matches that do not fall above a predetermined threshold (e.g., 100%, 98%, 97%, 95%, or 90%) of certainty and these results may be categorized as results that do not correspond with the characterized microorganism(s).

A quality of the results of comparisons of matches from steps 208 and 214 can be checked by limiting the analysis to sequence portions that have a predetermined length. For example, either a minimum threshold for sequence length could be set such as, for example, a minimum sequence length of 100 bp, or the results may be limited such that only those above which fall into a certain percentage of the longest sequences, for example, the top 100%, 50%, 30%, 20%, 15%, or 10% of all run sequence lengths may be selected on which to base the remaining analysis. By way of one example, the top 8.6% of sequence lengths can be used. The results can then be tabulated to determine how many matches correspond to each characterized or identified microorganism and any region information can also be tabulated to determine the number of matches for each region analyzed.

The system can then query a database of treatment information that may contain information such as the treatment (e.g., antibiotic, antiviral, antifungal, antiprotozoal) treatment and sensitivity and/or therapy resistance of the treatment(s) corresponding to each identified microorganism and the retrieved information may then be used to generate a final report. As shown in FIGS. 16-17, the output of the final report may display information such as, but not limited to: patient information, medical professional information, sample type, collection date, graphical or numerical data relating to one or more characterized or identified microorganisms, a percentage or other numerical indicator of contribution amount of each identified microorganism, a quantitative indicator for a match (e.g., an E-value or % Identity), a description of identified and/or unidentified (novel) microorganisms, and/or treatment sensitivity and/or therapy resistance information.

It may be advantageous to implement the disclosed system and methods in a language or other format that is compatible with a sequencing platform, such as an ions semiconductor sequencing platform—e.g., an IonTorent Server or an Illumina sequencer, as this may provide added efficiencies to the overall implementation.

Figure 15:
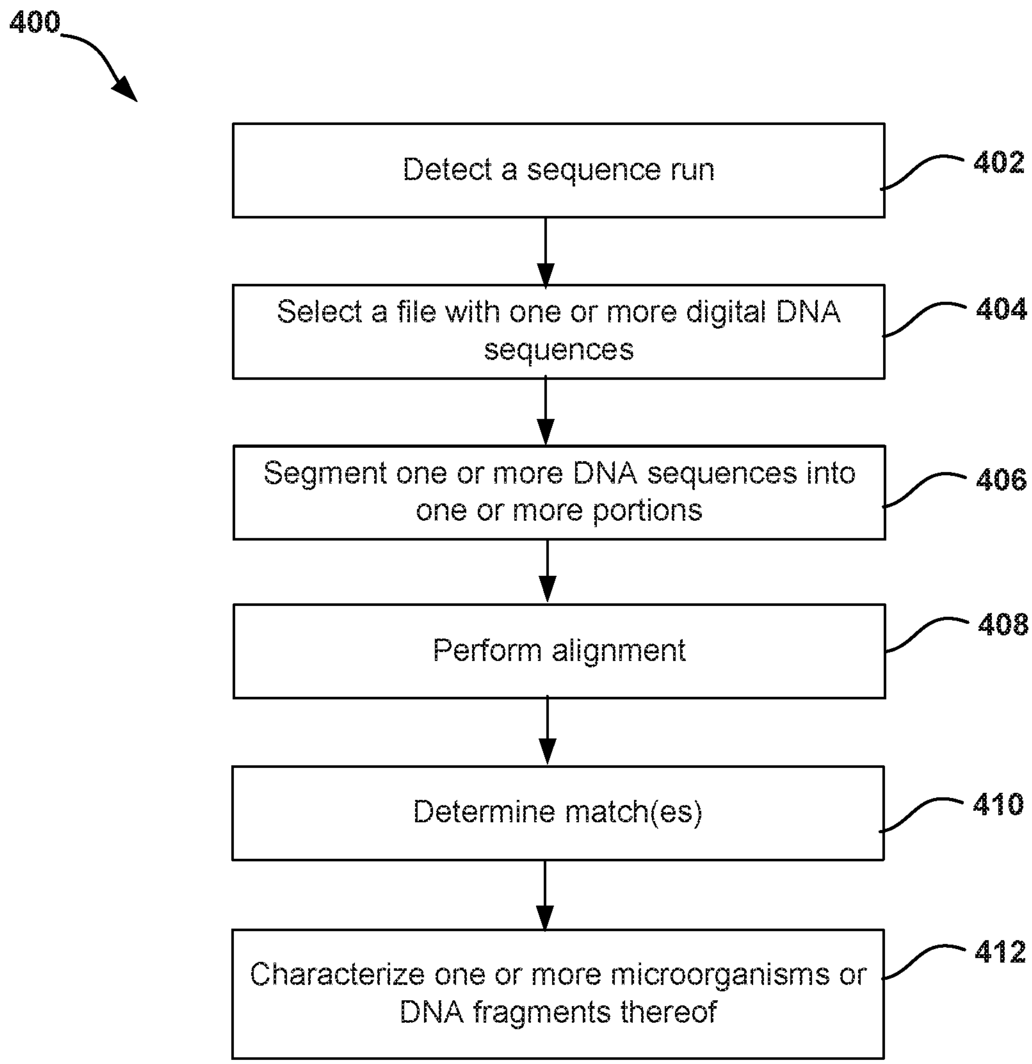
FIG. 15 illustrates another method in accordance with further exemplary embodiments of the disclosure.

Turning now to FIG. 15, a method 400 of automatically characterizing one or more microorganisms is illustrated. Method 400 is similar to method 200, except method 400 includes a step of detecting a sequence run that generates a digital DNA sequence of one or more microorganism (step 402) and does not necessarily, but can, include a performing a set of alignments by comparing the one or more sequence portions to information stored in a second database.

In the illustrated example, method 400 includes the steps of detecting a sequence run that generates a digital DNA sequence of one or more microorganisms (step 402); selecting, by a computer, a digital file comprising one or more digital DNA sequences, wherein each of the one or more digital DNA sequences corresponds to a microorganism to be characterized (step 404); segmenting, by the computer, each of the one or more digital DNA sequences into one or more portions (step 406); performing, by the computer, a set of alignments by comparing the one or more portions to information stored in one or more databases (step 408); determining, by the computer, sequence portions from among the one or more portions that have an alignment match to the information stored in the one or more databases (step 410); and characterizing one or more microorganisms or DNA fragments thereof based on the alignment match (step 412).

Step 402 includes automatically detecting a sequence run that generates a digital DNA sequence of one or more microorganisms. This can be done as described above in connection with process 300. Steps 404-412 can be the same or similar to steps 202-208 and 216 of method 200.

Method 400 can also include steps of optionally further segmenting, by the computer, each of the one or more digital DNA sequences into one or more second portions (wherein the portions noted above become first portions); performing, by the computer, a set of alignments by comparing the one or more first portions or the one or more second portions to information stored in a database (e.g., a second database); and determining, by the computer, sequence portions from among the one or more first portions or the one or more second portions that have an alignment match to the information stored in a database (e.g., the second database). Similar to method 200, these steps can be iteratively repeated with a comparison window decreasing in size with each run. Additional steps noted above in connection with method 200 can also be includes in method 400.

In accordance with various embodiments of the disclosure, method 200 or method 400 can be performed on a computer on a local network. By performing the processing functions of the disclosed systems or methods locally within the system, an Internet connection is not needed to sustain the processing. This offers additional security and reduces networking requirements. Implementations of the disclosed system and method are intended to integrate with existing and future Next Generation Sequencing software platforms such as, for example, Illumina® software applications such as Illumina MiSeq® and Illumina HiSeq®; LifeTechnologies Proton®; LifeTechnologies Personal Genome Machine, and PacBioRS II NGS sequencing systems.

Exemplary methods of the present disclosure described above may be implemented as one or more software processes executable by one or more processors and/or one or more firmware applications. The processes and/or firmware are configured to operate on one or more general purpose microprocessors or controllers, a field programmable gate array (FPGA), an application specific integrated circuit (ASIC), or other hardware capable of performing the actions describe above. In an exemplary embodiment of the present disclosure, software processes are executed by a CPU in order to perform the actions of the present disclosure. Additionally, the present disclosure is not described with reference to any particular programming language. It will be appreciated that a variety of programming languages may be used to implement the teachings of the disclosure as described herein.

Any of the methods herein may be employed with any form of memory device including all forms of sequential, pseudo-random, and random access storage devices. Storage devices as known within the current art include all forms of random access memory, magnetic and optical tape, magnetic and optical disks, along with various other forms of solid-state mass storage devices. The current disclosure applies to all forms and manners of memory devices including, but not limited to, storage devices utilizing magnetic, optical, and chemical techniques, or any combination thereof.

This disclosure is further illustrated by the following additional examples that should not be construed as limiting. It can be appreciated that many changes can be made to the specific embodiments which are disclosed and still obtain a like or similar result without departing from the spirit and scope of the disclosure.

EXAMPLES

Example 1. General DNA Extraction Procedures

Tissues, fluids, other biopsy material, environmental, or industrial material that is suspected of containing bacterial cells can be extracted using one of three main methods:

Bone or Tough Tissue Preparation

1) ~200 mg of bone or tissue is placed in a sterile 50 mL conical tube and 5 mL of molecular grade water is added to the sample.
2) The tissue is sonicated in 5-10 second bursts for a minimum of 5 minutes using a sterile sonicator probe at 10-14 watts.
3) 200 μL of supernatant and any remaining bone/tissue fragments are transferred to a sterile 2 mL screw cap tube and 50-100 μL of 1 mm uneven stainless steel beads, 200 μL of Qiagen Buffer AL, and 20 μL of Proteinase K is added to the sample.
4) The tube is then processed using a percussion based bead homogenizer for 5 minutes at medium speed.
5) 600 μL of the resulting supernatant is run through an inert filter column to remove beads.
6) 200 μL of 100% Ethanol is added to the sample.
7) From here the remaining steps are carried out as described in the Qiagen QIAamp DNA Blood Mini Kit protocol.
8) Final DNA is eluted in 30 μL.
9) Concentration of the extracted DNA is determined by NanoDrop analysis (Thermo Scientific, Wilmington, Delaware) of 4 μL.

Soft Tissue Preparation 1) 200 mg of soft tissue and 200 μL of molecular grade water is transferred to a sterile 2 mL screw cap tube and 50-100 μL of 1 mm glass beads, 200 μL of Qiagen Buffer AL, and 20 μL of Proteinase K is added to the sample.
2) The tube is then processed using a percussion based bead homogenizer for 5 minutes at medium speed.
3) ~600 μL of the resulting supernatant is run through an inert filter column to remove beads.
4) 200 μL of 100% Ethanol is added to the sample.
5) From here the remaining steps are carried out as described in the Qiagen QIAamp DNA Blood Mini Kit protocol.
6) Final DNA is eluted in 30 μL.
7) Concentration of the extracted DNA is determined by NanoDrop analysis (Thermo Scientific, Wilmington, Delaware) of 4 μL.

Fluid Preparation 1) 200 μL of blood or fluid is transferred to a sterile 2 mL screw cap tube and 50-100 μL of 1 mm glass beads, 200 μL of Qiagen Buffer AL, and 20 μL of Proteinase K is added to the sample.
2) The tube is then processed using a percussion based bead homogenizer for 5 minutes at medium speed.
3) ~400 μL of the resulting supernatant is run through an inert filter column to remove beads.
4) 200 μL of 100% Ethanol is added to the sample.
5) From here the remaining steps are carried out as described in the Qiagen QIAamp DNA Blood Mini Kit protocol.
6) Final DNA is eluted in 30 μL.
7) Concentration of the extracted DNA is determined by NanoDrop analysis (Thermo Scientific, Wilmington, Delaware) of 4 μL.

Example 2. DNA Purification from Tissues with the QIAamp® DNA Mini Kit

DNA can be purified from tissues using the QIAamp® DNA Mini Kit (QIAGEN, Germantown, Maryland).

Important Points Before Starting:

All centrifugation steps can be carried out at room temperature (~15-25° C.).

Use carrier DNA if the sample contains <10,000 genome equivalents.

Avoid repeated freezing and thawing of stored samples, since this leads to reduced DNA size.

Transcriptionally active tissues, such as liver and kidney, contain high levels of RNA which will copurify with genomic DNA. RNA may inhibit some downstream enzymatic reactions, but will not inhibit PCR. If RNA-free genomic DNA is required, include an RNase A digest.

Things to do Before Starting:

Equilibrate the sample to room temperature (~15-25° C.).

Heat 2 water baths or heating blocks: one to 56° C. for use in step 3, and one to 70° C. for use in step 5.

Equilibrate Buffer AE or distilled water to room temperature for elution in step 11.

Ensure that Buffers AW1 and AW2 have been prepared.

If a precipitate has formed in Buffer ATL or Buffer AL, dissolve by incubating at 56° C.

Exemplary Procedure

1. Excise the tissue sample or remove it from storage. Determine the amount of tissue. Do not use more than 25 mg (10 mg spleen). Weighing tissue is the most accurate way to determine the amount. If DNA is prepared from spleen tissue, no more than 10 mg should be used. The yield of DNA will depend on both the amount and the type of tissue processed. 1 mg of tissue will yield approximately 0.2-1.2 μg of DNA.
2. Cut up (step 2a), grind (step 2b), or mechanically disrupt (step 2c) the tissue sample. The QIAamp procedure requires no mechanical disruption of the tissue sample, but lysis time will be reduced if the sample is ground in liquid nitrogen (step 2b) or mechanically homogenized (step 2c) in advance.

2a. Cut up to 25 mg of tissue (up to 10 mg spleen) into small pieces. Place in a 1.5 ml microcentrifuge tube, and add 180 μl of Buffer ATL. Proceed with step 3. It is important to cut the tissue into small pieces to decrease lysis time. 2 ml microcentrifuge tubes may be better suited for lysis.

2b. Place up to 25 mg of tissue (10 mg spleen) in liquid nitrogen, and grind thoroughly with a mortar and pestle. Decant tissue powder and liquid nitrogen into 1.5 ml microcentrifuge tube. Allow the liquid nitrogen to evaporate, but do not allow the tissue to thaw, and add 180 μl of Buffer ATL. Proceed with step 3.

2c. Add up to 25 mg of tissue (10 mg spleen) to a 1.5 ml microcentrifuge tube containing no more than 80 μl PBS. Homogenize the sample using the TissueRuptor or equivalent rotor-stator homogenizer. Add 100 μl Buffer ATL, and proceed with step 3. Some tissues require undiluted Buffer ATL for complete lysis. In this case, grinding in liquid nitrogen is recommended. Samples cannot be homogenized directly in Buffer ATL, which contains detergent.

3. Add 20 μl proteinase K, mix by vortexing, and incubate at 56° C. until the tissue is completely lysed. Vortex occasionally during incubation to disperse the sample, or place in a shaking water bath or on a rocking platform. Note: Proteinase K can be used. QIAGEN Protease has reduced activity in the presence of Buffer ATL. Lysis time varies depending on the type of tissue processed. Lysis is usually complete in 1-3 h. Lysis overnight is possible and does not influence the preparation. In order to ensure efficient lysis, a shaking water bath or a rocking platform can be used. If not available, vortexing 2-3 times per hour during incubation is recommended.
4. Briefly centrifuge the 1.5 ml microcentrifuge tube to remove drops from the inside of the lid.
5. If RNA-free genomic DNA is desired, follow step 5a. Otherwise, follow step 5b. Transcriptionally active tissues, such as liver and kidney, contain high levels of RNA which will copurify with genomic DNA. RNA may inhibit some downstream enzymatic reactions, but will not inhibit PCR.

5a. First add 4 μl RNase A (100 mg/ml), mix by pulse-vortexing for 15 s, and incubate for 2 min at room temperature. Briefly centrifuge the 1.5 ml microcentrifuge tube to remove drops from inside the lid before adding 200 μl Buffer AL to the sample. Mix again by pulse-vortexing for 15 s, and incubate at 70° C. for 10 min. Briefly centrifuge the 1.5 ml microcentrifuge tube to remove drops from inside the lid. It is desirable that the sample and Buffer AL are mixed thoroughly to yield a homogeneous solution. A white precipitate may form on addition of Buffer AL. In most cases the precipitate will dissolve during incubation at 70° C. The precipitate does not interfere with the QIAamp procedure or with any subsequent application.

5b. Add 200 μl Buffer AL to the sample, mix by pulse-vortexing for 15 s, and incubate at 70° C. for 10 min. Briefly centrifuge the 1.5 ml microcentrifuge tube to remove drops from inside the lid. It is desirable that the sample and Buffer AL are mixed thoroughly to yield a homogeneous solution. A white precipitate may form on addition of Buffer AL, which in most cases will dissolve during incubation at 70° C. The precipitate does not interfere with the QIAamp procedure or with any subsequent application.

6. Add 200 μl ethanol (96-100%) to the sample, and mix by pulse-vortexing for 15 s. After mixing, briefly centrifuge the 1.5 ml microcentrifuge tube to remove drops from inside the lid. It is essential that the sample, Buffer AL, and the ethanol are mixed thoroughly to yield a homogeneous solution. A white precipitate may form on addition of ethanol. It is desirable to apply all of the precipitate to the QIAamp Mini spin column. This precipitate does not interfere with the QIAamp procedure or with any subsequent application. Use alcohols other than ethanol may result in reduced yields.

7. Carefully apply the mixture from step 6 (including the precipitate) to the QIAamp Mini spin column (in a 2 ml collection tube) without wetting the rim. Close the cap, and centrifuge at 6000×g (8000 rpm) for 1 min. Place the QIAamp Mini spin column in a clean 2 ml collection tube, and discard the tube containing the filtrate. Close each spin column to avoid aerosol formation during centrifugation. It is desirable to apply all of the precipitate to the QIAamp Mini spin column. Centrifugation is performed at 6000×g (8000 rpm) in order to reduce noise. Centrifugation at full speed will not affect the yield or purity of the DNA. If the solution has not completely passed through the membrane, centrifuge again at a higher speed until all the solution has passed through.
8. Carefully open the QIAamp Mini spin column and add 500 μl Buffer AW1 without wetting the rim. Close the cap, and centrifuge at 6000×g (8000 rpm) for 1 min. Place the QIAamp Mini spin column in a clean 2 ml collection tube, and discard the collection tube containing the filtrate.
9. Carefully open the QIAamp Mini spin column and add 500 μl Buffer AW2 without wetting the rim. Close the cap and centrifuge at full speed (20,000×g; 14,000 rpm) for 3 min.
10. Recommended: Place the QIAamp Mini spin column in a new 2 ml collection tube and discard the old collection tube with the filtrate. Centrifuge at full speed for 1 min. This step helps to eliminate the chance of possible Buffer AW2 carryover.
11. Place the QIAamp Mini spin column in a clean 1.5 ml microcentrifuge tube, and discard the collection tube containing the filtrate. Carefully open the QIAamp Mini spin column and add 200 μl Buffer AE or distilled water. Incubate at room temperature for 1 min, and then centrifuge at 6000×g (8000 rpm) for 1 min.
12. Repeat step 11. A 5 min incubation of the QIAamp Mini spin column loaded with Buffer AE or water, before centrifugation, generally increases DNA yield. A third elution step with a further 200 μl Buffer AE will increase yields by up to 15%. Volumes of more than 200 μl should not be eluted into a 1.5 ml microcentrifuge tube because the spin column will come into contact with the eluate, leading to possible aerosol formation during centrifugation. Elution with volumes of less than 200 μl increases the final DNA concentration in the eluate significantly, but slightly reduces the overall DNA yield. Eluting with 4×100 μl instead of 2×200 μl does not increase elution efficiency. For long-term storage of DNA, eluting in Buffer AE and placing at ~20° C. is recommended, since DNA stored in water is subject to acid hydrolysis. Yields of DNA can depend both on the amount and the type of tissue processed. 25 mg of tissue can yield approximately 10-30 μg of DNA in 400 μl of water (25-75 ng/μl), with an $A_{260}/A_{280}$ ratio of 1.7-1.9.

Example 3. DNA Purification from Blood with the QIAamp® DNA Mini Kit

DNA can be purified from blood using the QIAamp® DNA Mini Kit (QIAGEN, Germantown, Maryland).

This protocol can be for purification of total (genomic, mitochondrial, and viral) DNA from whole blood, plasma, serum, buffy coat, lymphocytes, and body fluids using a microcentrifuge.

Important Points Before Starting:

All centrifugation steps are carried out at room temperature (~15-25° C.).

Use carrier DNA if the sample contains <10,000 genome equivalents.

200 μl of whole blood yields 3-12 μg of DNA. Preparation of buffy coat is recommended if a higher yield is desired.

Things to do Before Starting:

Equilibrate samples to room temperature.

Heat a water bath or heating block to 56° C. for use in step 4.

Equilibrate Buffer AE or distilled water to room temperature for elution in step 11.

Ensure that Buffer AW1, Buffer AW2, and QIAGEN Protease have been prepared.

If a precipitate has formed in Buffer AL, dissolve by incubating at 56° C.

Exemplary Procedure

1. Pipet 20 μl QIAGEN Protease (or proteinase K) into the bottom of a 1.5 ml microcentrifuge tube.
2. Add 200 μl sample to the microcentrifuge tube. Use up to 200 μl whole blood, plasma, serum, buffy coat, or body fluids, or up to 5×106 lymphocytes in 200 μl PBS. If the sample volume is less than 200 μl, add the appropriate volume of PBS. QIAamp Mini spin columns copurify RNA and DNA when both are present in the sample. RNA may inhibit some downstream enzymatic reactions, but not PCR. If RNA-free genomic DNA is desired, 4 μl of an RNase A stock solution (100 mg/ml) should be added to the sample before addition of Buffer AL. Note: It is possible to add QIAGEN Protease (or proteinase K) to samples that have already been dispensed into microcentrifuge tubes. In this case, it is desirable to ensure proper mixing after adding the enzyme.
3. Add 200 μl Buffer AL to the sample. Mix by pulse-vortexing for 15 s. In order to ensure efficient lysis, it is desirable that the sample and Buffer AL are mixed thoroughly to yield a homogeneous solution. If the sample volume is larger than 200 μl, increase the amount of QIAGEN Protease (or proteinase K) and Buffer AL proportionally; for example, a 400 μl sample will use 40 μl QIAGEN Protease (or proteinase K) and 400 μl Buffer AL. If sample volumes larger than 400 μl are desired, use of QIAamp DNA Blood Midi or Maxi Kits is recommended; these can process up to 2 ml or up to 10 ml of sample, respectively. Note: Do not add QIAGEN Protease or proteinase K directly to Buffer AL.
4. Incubate at ~56° C. for ~10 min. DNA yield reaches a maximum after lysis for ~10 min at ~56° C. Longer incubation times have may no effect on yield or quality of the purified DNA.
5. Briefly centrifuge the 1.5 ml microcentrifuge tube to remove drops from the inside of the lid.
6. Add 200 μl ethanol (96-100%) to the sample, and mix again by pulse-vortexing for 15 s. After mixing, briefly centrifuge the 1.5 ml microcentrifuge tube to remove drops from the inside of the lid. If the sample volume is greater than 200 μl, increase the amount of ethanol proportionally; for example, a 400 μl sample can use 400 μl of ethanol.

7. Carefully apply the mixture from step 6 to the QIAamp Mini spin column (in a 2 ml collection tube) without wetting the rim. Close the cap, and centrifuge at 6000×g (8000 rpm) for 1 min. Place the QIAamp Mini spin column in a clean 2 ml collection tube, and discard the tube containing the filtrate. Close each spin column in order to avoid aerosol formation during centrifugation. Centrifugation is performed at 6000×g (8000 rpm) in order to reduce noise. Centrifugation at full speed will not affect the yield or purity of the DNA. If the lysate has not completely passed through the column after centrifugation, centrifuge again at higher speed until the QIAamp Mini spin column is empty. Note: When preparing DNA from buffy coat or lymphocytes, centrifugation at full speed is recommended to avoid clogging.
8. Carefully open the QIAamp Mini spin column and add 500 μl Buffer AW1 without wetting the rim. Close the cap and centrifuge at 6000×g (8000 rpm) for 1 min. Place the QIAamp Mini spin column in a clean 2 ml collection tube, and discard the collection tube containing the filtrate. It is not necessary to increase the volume of Buffer AW1 if the original sample volume is larger than 200 μl.
9. Carefully open the QIAamp Mini spin column and add 500 μl Buffer AW2 without wetting the rim. Close the cap and centrifuge at full speed (20,000×g; 14,000 rpm) for 3 min.
10. Recommended: Place the QIAamp Mini spin column in a new 2 ml collection tube and discard the old collection tube with the filtrate. Centrifuge at full speed for 1 min. This step helps to eliminate the chance of possible Buffer AW2 carryover.
11. Place the QIAamp Mini spin column in a clean 1.5 ml microcentrifuge tube, and discard the collection tube containing the filtrate. Carefully open the QIAamp Mini spin column and add 200 μl Buffer AE or distilled water. Incubate at room temperature (15-25° C.) for 1 min, and then centrifuge at 6000×g (8000 rpm) for 1 min. Incubating the QIAamp Mini spin column loaded with Buffer AE or water for 5 min at room temperature before centrifugation generally increases DNA yield. A second elution step with a further 200 μl Buffer AE will increase yields by up to 15%. Volumes of more than 200 μl should not be eluted into a 1.5 ml microcentrifuge tube because the spin column will come into contact with the eluate, leading to possible aerosol formation during centrifugation. Elution with volumes of less than 200 μl increases the final DNA concentration in the eluate significantly, but slightly reduces the overall DNA yield. For samples containing less than 1 μg of DNA, elution in 50 μl Buffer AE or water is recommended. Eluting with 2×100 μl instead of 1×200 μl does not increase elution efficiency. For long-term storage of DNA, eluting in Buffer AE and storing at ~20° C. is recommended, since DNA stored in water is subject to acid hydrolysis. A 200 μl sample of whole human blood (approximately 5×106 leukocytes/ml) typically yields 6 μg of DNA in 200 μl water (30 ng/μl) with an A260/A280 ratio of 1.7-1.9.

Example 4. Amplification and Barcoding of Extracted DNA

PCR amplification reactions are set up for two 16S regions per sample. Each sample is designated by its own DNA barcode. The following reactions are generated for each sample including one positive and one negative amplification control:

| Region | V1/2 | Region | V5/4 |
|---|---|---|---|
| 3.48 μL | dH2O | 3.48 μL | dH2O |
| 5.00 μL | ENA | 5.00 μL | ENA |
| 0.26 μL | A_BarcodeX_V1/2_F | 0.26 μL | A_BarcodeX_V5/4_F |
| 0.26 μL | P1_V1/2_R | 0.26 μL | P1_V5/4_R |
| 1.00 μL | Template DNA | 1.00 μL | Template DNA |

Note that in the above PCR reaction mixtures that ENA are 2'-O,4'-C-ethylene bridged nucleic acids; A_BarcodeX_V1/2_F and A_BarcodeX_V5/4_F are forward primers; and P1_V1/2_R and P1_V5/4_R are reverse primers. The V1/2 primers are selected from Table 4, and the V5/4 primers are selected from Table 5.

TABLE 4

| Examples of V1/2 Primers. Barcodes are underlined, and the 16S Variable Region Homology is in bold. |
|---|
| Forward Primer (Primer A-Barcode 1-V1/2) (SEQ ID NO: 35)<br>CCATCTCATCCCTGCGTGTCTCCGACTCAGCTAAGGTAACGAT**AGAGTTTGATCCTGGCTCAG** |
| Forward Primer (Primer A-Barcode 2-V1/2) (SEQ ID NO: 36)<br>CCATCTCATCCCTGCGTGTCTCCGACTCAGTAAGGAGAACGAT**AGAGTTTGATCCTGGCTCAG** |
| Forward Primer (Primer A-Barcode 3-V1/2) (SEQ ID NO: 37)<br>CCATCTCATCCCTGCGTGTCTCCGACTCAGAAGAGGATTCGAT**AGAGTTTGATCCTGGCTCAG** |
| Forward Primer (Primer A-Barcode 4-V1/2) (SEQ ID NO: 38)<br>CCATCTCATCCCTGCGTGTCTCCGACTCAGTACCAAGATCGAT**AGAGTTTGATCCTGGCTCAG** |
| Forward Primer (Primer A-Barcode 5-V1/2) (SEQ ID NO: 39)<br>CCATCTCATCCCTGCGTGTCTCCGACTCAGCAGAAGGAACGAT**AGAGTTTGATCCTGGCTCAG** |
| Forward Primer (Primer A-Barcode 6-V1/2) (SEQ ID NO: 40)<br>CCATCTCATCCCTGCGTGTCTCCGACTCAGCTGCAAGTTCGAT**AGAGTTTGATCCTGGCTCAG** |
| Forward Primer (Primer A-Barcode 7-V1/2) (SEQ ID NO: 41)<br>CCATCTCATCCCTGCGTGTCTCCGACTCAGTTCGTGATTCGAT**AGAGTTTGATCCTGGCTCAG** |

TABLE 4-continued

Examples of V1/2 Primers. Barcodes are underlined, and the 16S Variable Region Homology is in bold.

Forward Primer (Primer A-Barcode 8-V1/2) (SEQ ID NO: 42)
CCATCTCATCCCTGCGTGTCTCCGACTCAGTTCCGATAACGATAGAGTTTGATCCTGGCTCAG

Forward Primer (Primer A-Barcode 9-V1/2) (SEQ ID NO: 43)
CCATCTCATCCCTGCGTGTCTCCGACTCAGTGAGCGGAACGATAGAGTTTGATCCTGGCTCAG

Forward Primer (Primer A-Barcode 10-V1/2) (SEQ ID NO: 44)
CCATCTCATCCCTGCGTGTCTCCGACTCAGCTGACCGAACGATAGAGTTTGATCCTGGCTCAG

Forward Primer (Primer A-Barcode 11-V1/2) (SEQ ID NO: 45)
CCATCTCATCCCTGCGTGTCTCCGACTCAGTCCTCGAATCGATAGAGTTTGATCCTGGCTCAG

Forward Primer (Primer A-Barcode 12-V1/2) (SEQ ID NO: 46)
CCATCTCATCCCTGCGTGTCTCCGACTCAGTAGGTGGTTCGATAGAGTTTGATCCTGGCTCAG

Forward Primer (Primer A-Barcode 13-V1/2) (SEQ ID NO: 47)
CCATCTCATCCCTGCGTGTCTCCGACTCAGTCTAACGGACGATAGAGTTTGATCCTGGCTCAG

Forward Primer (Primer A-Barcode 14-V1/2) (SEQ ID NO: 48)
CCATCTCATCCCTGCGTGTCTCCGACTCAGTTGGAGTGTCGATAGAGTTTGATCCTGGCTCAG

Forward Primer (Primer A-Barcode 15-V1/2) (SEQ ID NO: 49)
CCATCTCATCCCTGCGTGTCTCCGACTCAGTCTAGAGGTCGATAGAGTTTGATCCTGGCTCAG

Forward Primer (Primer A-Barcode 16-V1/2) (SEQ ID NO: 50)
CCATCTCATCCCTGCGTGTCTCCGACTCAGTCTGGATGACGATAGAGTTTGATCCTGGCTCAG

Reverse Primer (Primer P1-V1/2) (SEQ ID NO: 33)
CCTCTCTATGGGCAGTCGGTGATCTGCTGCCTYCCGTA

TABLE 5

Examples of V5/4 Primers. Barcodes are underlined, and the 16S Variable Region Homology is in bold.

Forward Primer (Primer A-Barcode 1-V5/4) (SEQ ID NO: 51)
CCATCTCATCCCTGCGTGTCTCCGACTCAGCTAAGGTAACGATCCGTCAATTYYTTTRAGTTT

Forward Primer (Primer A-Barcode 2-V5/4) (SEQ ID NO: 52)
CCATCTCATCCCTGCGTGTCTCCGACTCAGTAAGGAGAACGATCCGTCAATTYYTTTRAGTTT

Forward Primer (Primer A-Barcode 3-V5/4) (SEQ ID NO: 53)
CCATCTCATCCCTGCGTGTCTCCGACTCAGAAGAGGATTCGATCCGTCAATTYYTTTRAGTTT

Forward Primer (Primer A-Barcode 4-V5/4) (SEQ ID NO: 54)
CCATCTCATCCCTGCGTGTCTCCGACTCAGTACCAAGATCGATCCGTCAATTYYTTTRAGTTT

Forward Primer (Primer A-Barcode 5-V5/4) (SEQ ID NO: 55)
CCATCTCATCCCTGCGTGTCTCCGACTCAGCAGAAGGAACGATCCGTCAATTYYTTTRAGTTT

Forward Primer (Primer A-Barcode 6-V5/4) (SEQ ID NO: 56)
CCATCTCATCCCTGCGTGTCTCCGACTCAGCTGCAAGTTCGATCCGTCAATTYYTTTRAGTTT

Forward Primer (Primer A-Barcode 7-V5/4) (SEQ ID NO: 57)
CCATCTCATCCCTGCGTGTCTCCGACTCAGTTCGTGATTCGATCCGTCAATTYYTTTRAGTTT

Forward Primer (Primer A-Barcode 8-V5/4) (SEQ ID NO: 58)
CCATCTCATCCCTGCGTGTCTCCGACTCAGTTCCGATAACGATCCGTCAATTYYTTTRAGTTT

Forward Primer (Primer A-Barcode 9-V5/4) (SEQ ID NO: 59)
CCATCTCATCCCTGCGTGTCTCCGACTCAGTGAGCGGAACGATCCGTCAATTYYTTTRAGTTT

Forward Primer (Primer A-Barcode 10-V5/4) (SEQ ID NO: 60)
CCATCTCATCCCTGCGTGTCTCCGACTCAGCTGACCGAACGATCCGTCAATTYYTTTRAGTTT

Forward Primer (Primer A-Barcode 11-V5/4) (SEQ ID NO: 61)
CCATCTCATCCCTGCGTGTCTCCGACTCAGTCCTCGAATCGATCCGTCAATTYYTTTRAGTTT

Forward Primer (Primer A-Barcode 12-V5/4) (SEQ ID NO: 62)
CCATCTCATCCCTGCGTGTCTCCGACTCAGTAGGTGGTTCGATCCGTCAATTYYTTTRAGTTT

Forward Primer (Primer A-Barcode 13-V5/4) (SEQ ID NO: 63)
CCATCTCATCCCTGCGTGTCTCCGACTCAGTCTAACGGACGATCCGTCAATTYYTTTRAGTTT

TABLE 5-continued

| Examples of V5/4 Primers. Barcodes are underlined, and the 16S Variable Region Homology is in bold. |
|---|
| Forward Primer (Primer A-Barcode 14-V5/4) (SEQ ID NO: 64)<br>CCATCTCATCCCTGCGTGTCTCCGACTCAG<u>TTGGAGTGTC</u>GAT**CCGTCAATTYYTTTRAGTTT** |
| Forward Primer (Primer A-Barcode 15-V5/4) (SEQ ID NO: 65)<br>CCATCTCATCCCTGCGTGTCTCCGACTCAG<u>TCTAGAGGTC</u>GAT**CCGTCAATTYYTTTRAGTTT** |
| Forward Primer (Primer A-Barcode 16-V5/4) (SEQ ID NO: 66)<br>CCATCTCATCCCTGCGTGTCTCCGACTCAG<u>TCTGGATGAC</u>GAT**CCGTCAATTYYTTTRAGTTT** |
| Reverse Primer (Primer P1-V5/4) (SEQ ID NO: 34)<br>CCTCTCTATGGGCAGTCGGTGAT**AYTGGGYDTAAAGNG** |

The PCR is then run with the Thermocycler set to the following conditions:

The PCR is then run with the Thermocycler set to the following conditions:

| Step# | Temp. | Time | Notes |
|---|---|---|---|
| 1) | 96° C. | | 1 minute |
| 2) | 96° C. | | 20 seconds |
| 3) | 42° C. | | 30 seconds |
| 4) | 72° C. | | 30 seconds |
| 5) | — | — | Repeat 2-4 40x |
| 6) | 4° C. | Indefinitely | |

Example 5. Purification of DNA from PCR Reactions

After barcoding and amplification of the extracted DNA, the resulting DNA reactions are purified to remove extraneous DNA sequences that are not the targets for sequencing with standard gel electrophoresis and gel extraction. Gel extraction is performed using the QiaPrep Gel Extraction Mini kit (QIAGEN, Germantown, Maryland).

Example 6. IonSphere Particle Labeling

All purified DNA samples from the PCR reactions are pooled together in equimolar ratios determined by NanoDrop (Thermo Scientific, Wilmington, Delaware) and the known DNA fragment sizes. The pooled library is diluted to precisely 0.08 pM and used as the DNA template for the OneTouch IonSphere Particle Labeling protocol as listed in the Ion OneTouch 200 Template Kit v2 DL (Pub #MAN0007112, Revision: 5.0) in conjunction with the Ion OneTouch 200 Template Kit v2 DL kit.

The OneTouch IonSphere Particle (ISP) Labeling protocol is followed with a few modifications to the "Add Ion OneTouch Reaction Oil" loading step and the "Recover the Template-Positive ISPs" step. The changes are as follows:

Add Ion OneTouch Reaction Oil

Add Ion OneTouch™ Reaction Oil Through the Sample Port:

a. Set a P1000 pipette to 750 μL and attach a new 1000-μL tip to the pipette.
b. Fill the tip with 750 μL of Reaction Oil.
c. Insert the tip firmly into the sample port so that the tip is perpendicular to the Ion OneTouch™ Plus Reaction Filter Assembly and fully inserted into the sample port to form a tight seal.
d. Gently pipet 750 μL of the Reaction Oil through the sample port. Keep the plunger of the pipette depressed to avoid aspirating solution from the Ion PGM™ OneTouch Plus Reaction Filter Assembly.
e. With the plunger still depressed, remove the tip from the sample port, then appropriately discard the tip.
f. Set the P1000 pipette to 750 μL and attach a new 1000-μL tip to the pipette.
g. Fill the tip with 750 μL of Reaction Oil.
h. Insert the tip firmly into the sample port so that the tip is perpendicular to the Ion OneTouch™ Plus Reaction Filter Assembly and fully inserted into the sample port to form a tight seal.
i. Gently pipet 750 μL of the Reaction Oil through the sample port, then keep the plunger of the pipette depressed.
j. With the plunger still depressed, remove the tip from the sample port, then appropriately discard the tip.
k. If desired, gently dab a Kimwipes® disposable wiper around the ports to remove any liquid.

Recover the Template-Positive ISPs

1. At the end of the run, ensure that you centrifuged the samples. (Ensure that you have touched Next on the Centrifuge screen to centrifuge the samples and that the home screen displays after the centrifugation.)
2. Immediately after the centrifuge stops, remove and discard the Recovery Router.
3. Carefully remove both Recovery Tubes from the instrument, and put the two Recovery Tubes in a tube rack. You may see some cloudiness in the tube, which is normal.
4. Label a new 1.5-mL LoBind Tube for the template-positive ISPs.
5. Use a pipette to remove all but ~100 μL of Ion OneTouch™ Recovery Solution from each Ion OneTouch™ Recovery Tube. Do not disturb the pellet of template-positive ISPs.
6. Add 1 mL of Ion OneTouch Wash solution to one Recovery Tube with the ISP pellet and resuspend the pellet by gently pipetting up and down.
7. Transfer the Ion OneTouch Wash solution and resuspended ISPs to the other Recovery Tube and resuspend the pellet by gently pipetting up and down.
8. Transfer the ~1.2 mL suspension to the new labeled tube.

Stopping Point: The template-positive ISPs with Ion OneTouch™ Wash

Solution may be stored at 2° C. to 8° C. for up to 3 days. After storage, proceed to step 10.

Do not store the recovered ISPs in Ion OneTouch™ Recovery Solution.

9. Centrifuge the template-positive ISP suspension for 2.5 minutes at 15,500×g.
10. Remove all but 100 μL of supernatant.
11. Vortex the pellet for 30 seconds to completely resuspend the template-positive ISPs.
12. (Optional) Assess the quality of the unenriched, template-positive ISPs.
13. Enrich the template-positive ISPs.

Example 7. IonSphere Particle Enrichment and DNA Sequencing

IonSphere Particle Enrichment

The IonSphere Particle Enrichment protocol is performed as listed in the Ion OneTouch 200 Template Kit v2 DL (Pub #MAN0007112, Revision: 5.0) in conjunction with the Ion OneTouch 200 Template Kit v2 DL kit (Life Technologies, Carlsbad, California).

DNA Sequencing

The DNA Sequencing protocol is performed as listed in the Ion PGM Sequencing Kit manuals for the appropriate sequencing length kit in conjunction with the Ion PGM Sequencing Kits. The only variation to the protocol is a modification of the total flow cycle numbers whereby the total flow cycle number is increased by 80 flows above the kit specifications.

Example 8. Computer-Based Genomic Analysis

Once sequencing is complete, individually barcoded sequence sets may be downloaded from the Ion Torrent Browser interface. These are imported as FASTQ files into CLC Workbench. Each sequence set is then preferably processed according to the following steps:

1. Sequences of a specific barcode are length selected and only 100 bp length sequences or greater are retained.
2. These sequences are BLASTed against a local 16S database of known, named, and non-redundant Eubacteria.
3. The resulting BLAST results are size sorted.
4. A size cut-off is selected for each BLAST results based on three factors.
   a. Distribution of the reads obtained for that given barcode and the first "cluster" of sequence read lengths is selected with the cut-off as high as possible to include this sequence cluster.
   b. If no cluster of sequences is apparent then approximately 100 of the longest sequences are selected for reporting.
   c. Sequences less than 100 bp are not used for reporting.
5. The following statistical information is reported based on the provided cut-off values:
   a. >100 bp—The species for an individual sequence read is correctly identified greater than 10% of the time.
   b. >150 bp—The species for an individual sequence read is correctly identified greater than 15% of the time.
   c. >175 bp—The species for an individual sequence read is correctly identified greater than 25% of the time.
   d. >250 bp—The species for an individual sequence read is correctly identified greater than 30% of the time.
   e. >300 bp—The species for an individual sequence read is correctly identified greater than 35% of the time.
   f. >355 bp—The species for an individual sequence read is correctly identified greater than 95% of the time.
6. Repeat positive results increased the chances of a correctly called sample. Therefore, sequences are only reported if they comprise >1% of the total identified sequence reads and are represented by >5 sequences in total. In this case a sample comprising 1% of a total sequence read with a cut-off at 100 bp would have much less than a 1% chance (All 5 wrong out of 100,000 chances=0.005%) of incorrectly identifying the species as an aggregate. Often times there are hundreds or thousands of sequences that identify the same species, thus it is a statistical certainty that the species are correctly identified on the highest ends of the reporting ranges.
7. A report is generated that graphically displays the proportion of the top 6 or less species identified. A table is also provided that lists the sequence counts and relative percentages of all significant sequences (>1% contribution and 5 or more sequences). Treatment resistance information is provided for each identified genus including scientific and medical references containing that information.

Example 9. Pan-Bacterial Metagenomics Analysis No. 1

A dental sample from a patient was processed to extract the nucleic acids, prepare an ion amplicon library, purify the ion amplicon library, sequence the 16S rRNA in the library, and identify the species of microorganisms present in the biological sample with a computer-based genomic analysis using the procedures described in Examples 1-8. PCR primers were selected from those listed in Tables 4 and 5.

Sequence Information: 365,254 sequence reads were obtained for the given sample. The longest 252 sequences were analyzed and compared to all available prokaryotic species.

Results Confidence Profile (355): At the provided quality control cut-off it is estimated that >95% of the sequence reads correctly list the genus, while >95% of the sequence reads correctly list the species.

Figure 4:
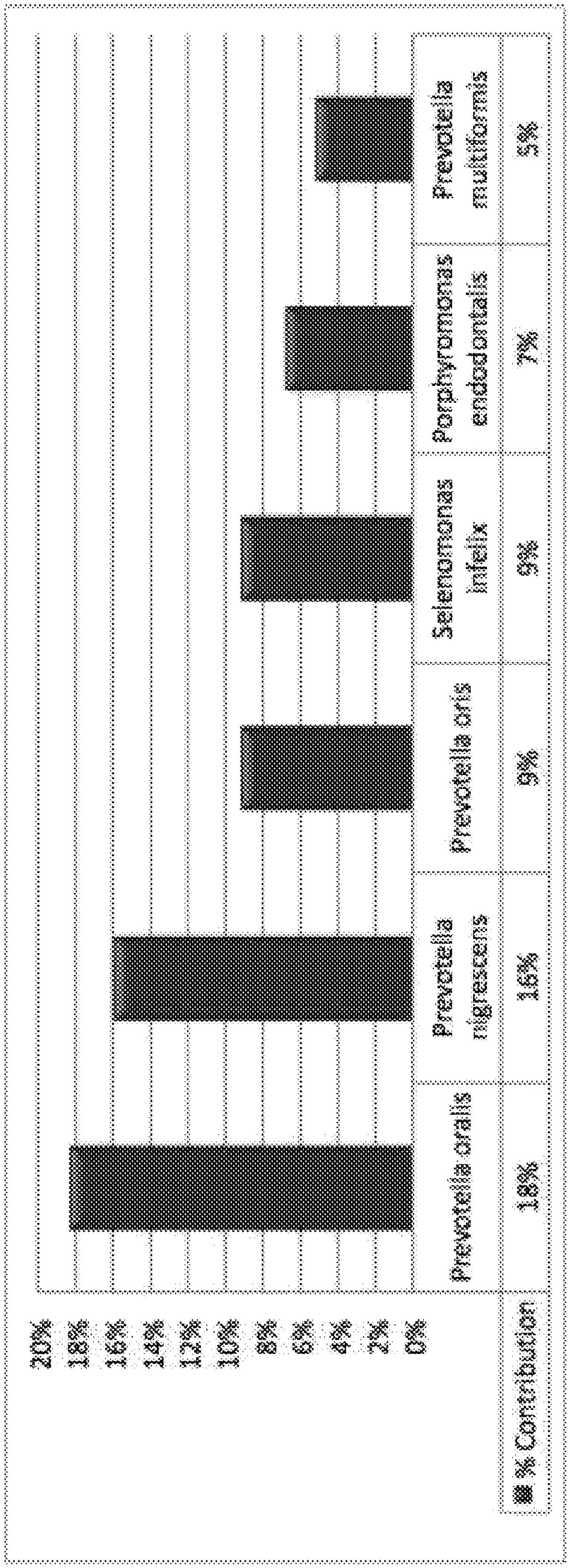
FIG. 4 illustrates results of a computer-based genomics analysis of a patient sample with *Prevotella* spp. as the most abundant microorganisms identified.

The identified species are shown in Table 6 and FIG. 4.

TABLE 6

Species identified by computer-based genomics analysis

| Species | Number of Sequences | % |
|---|---|---|
| *Prevotella oralis* | 46 | 18% |
| *Prevotella nigrescens* | 40 | 16% |
| *Prevotella oris* | 23 | 9% |
| *Selenomonas infelix* | 23 | 9% |
| *Porphyromonas endodontalis* | 17 | 7% |
| *Prevotella multiformis* | 13 | 5% |
| *Fusobacterium nucleatum* | 12 | 5% |
| *Selenomonas sputigena* | 12 | 5% |
| *Prevotella intermedia* | 10 | 4% |
| *Prevotella dentalis* | 8 | 3% |
| *Prevotella oulorum* | 6 | 2% |

The antibiotic susceptibility was determined and reported based on the genera identified with the computer-based genomic analysis. The results are shown in Table 7.

TABLE 7

| Antibiotic susceptibilities | | |
|---|---|---|
| Description | Genus Antibiotics | Noted Resistance |
| *Prevotella oralis* | Metronidazole, amoxycillin/clavulanate, doxycycline, ureidopenicilins, carbapenems, cephalosporins, clindamycin, and chloramphenicol. | Metronidazole, amoxicillin, amoxycillin/clavulanate, ureidopenicilins, carbapenems, cephalosporins, clindamycin, clarithromycin, chloramphenicol, moxifloxacin, and levofloxacin. |
| *Prevotella nigrescens* | Refer to *Prevotella oralis*. | Refer to *Prevotella oralis*. |
| *Prevotella oris* | Refer to *Prevotella oralis*. | Refer to *Prevotella oralis*. |
| *Selenomonas infelix* | Azithromycin. | Erythromycin. |
| *Porphyromonas endodontalis* | Penicillins (ampicillin, amoxicillin, ticarcillin), cephaloridine, cephalothin, cefamandole, cefotaxime, cefoxitin, cefuroxime, imipenem, piperacillin, erythromycin, oleandomycin, spiramycin, clindamycin, tetracycline, metronidazole, azithromycin, and doxycycline. | Unknown |
| *Prevotella multiformis* | Refer to *Prevotella oralis*. | Refer to *Prevotella oralis*. |

*Prevotella* Species:

Antibiotics: Antibiotic susceptibility varies among *Prevotella* species. Antibiotics used to treat *Prevotella* infections include: metronidazole, amoxycillin/clavulanate, doxycycline, ureidopenicilins, carbapenems, cephalosporins, clindamycin, and chloramphenicol. Resistance: Resistance to metronidazole, amoxicillin, amoxycillin/clavulanate, ureidopenicilins, carbapenems, cephalosporins, clindamycin, clarithromycin, chloramphenicol, moxifloxacin, and levofloxacin have been reported.

REFERENCES

Flynn, M. J., Li, G., Slots, J. (1994). *Mitsuokella dentalis* in human periodontitis. Oral Microbiol. Immunol. 9, 248-250.

Mosca A, Miragliotta L, Iodice M A, et al. Antimicrobial profiles of *Prevotella* spp. and *Fusobacterium nucleatum* isolated form periodontal infections in a selected area of southern Italy. Int J of Antimicro Agents December 2007; 30(6):521-4.

Shah, H. N., Collins, D. M. (1990). *Prevotella*, a new genus to include *Bacteroides melaninogenicus* and related species formerly classified in the genus Bacterioides. Int. J. syst. Bacteriol. 40, 205-208.

*Selenomonas* Species:

Antibiotics: Active antibiotics include: Azithromycin.

Resistance: Inactive antibiotics: Erythromycin.

REFERENCES

Comparative in-vitro activity of azithromycin, macrolides (erythromycin, clarithromycin and spiramycin) and streptogramin RP 59500 against oral organisms. Williams, J. D., Maskell, J. P., Shain, H., Chrysos, G., Sefton, A. M., Fraser, H. Y., Hardie, J. M. *J. Antimicrob. Chemother*. (1992).

*Porphyromonas* Species:

Antibiotics: Antibiotic susceptibility varies among *Porphyromonas* species. Antibiotics used to treat *Peptostreptococcus* infections include: Penicillins (ampicillin, amoxicillin, ticarcillin), cephaloridine, cephalothin, cefamandole, cefotaxime, cefoxitin, cefuroxime, imipenem, piperacillin, erythromycin, oleandomycin, spiramycin, clindamycin, tetracycline, metronidazole, azithromycin, and doxycycline.

Resistance: Resistance to antibiotics has not been reported to a significant degree.

REFERENCES

Andres M T, Chung W O, Roberts M C, and Fierro J F. Antimicrobial susceptibilities of *Porphyromonas gingivalis, Prevotella intermedia*, and *Prevotella nigrescens* spp. Isolated in Spain. Antimicrob Agents Chemoth. November 1998; 42(11):3022-3.

Japoni A, Vazin A, Noushadi S, Kiany F, et al. Antibacterial susceptibility patterns of *Porphyromonas gingivalis* isolated from chronic periodontitis patients. November 2011; 16(7):e1031-5.

Kulik E M, Lenkeit K, Chenaux S, and Meyer J. Antimicrobial susceptibility of periodontopathogenic bacteria. J Antimicrob Chemother March 2008; 61(5):1087-91.

Pajukanta R, Asikainen S, Forsblom B, Saarela M, Jousimies-Somer H. β-Lactamase production and in vitro antimicrobial susceptibility of *Porphyromonas gingivalis*. FEMS Immunol Med Microbiol. 1993; 6:241-244.

*Fusobacterium* Species:

Antibiotics: Antibiotic susceptibility varies among *Fusobacterium* species. Treatment of *Fusobacterium* infections depends on the site of infections. Antibiotics used to treat *Fusobacterium* infections include: Metronidazole, piperacillin/tazobactum, ticarcillin/clavulanate, amoxicillin/sulbactum, ampicillin/sulbactum, ertupenem, imipenem, meropenem, clindamycin, and cefoxitin.

Resistance: Some resistance to penicillin noted with widespread resistance to erythromycin and other macrolides.

REFERENCES

Citron, D. M., Poxton, I. R., & Baron, E. J. (2007). *Bacteroides, Porphyromonas, Prevotella, Fusobacterium*, and Other Anaerobic Gram-Negative Rods. In P. R. Murray, E. J. Baron, M. L. Landry, J. H. Jorgensen & M. A. Pfaller (Eds.), Manual of Clinical Microbiology (9th ed., pp. 911-932). Washington, D.C.: ASM Press.

Riordan, T. (2007). Human infection with *Fusobacterium necrophorum* (Necrobacillosis), with a focus on Lemierre's syndrome. Clinical Microbiology Reviews, 20(4), 622-659. doi:10.1128/CMR.00011-07.

Boyanova, L., Kolarov, R., & Mitov, I. (2007). Antimicrobial resistance and the management of anaerobic infections. Expert Review of Anti-Infective Therapy, 5(4), 685-701.

Example 10. Pan-Bacterial Metagenomics Analysis No. 2

A dental sample from a patient was processed to extract the nucleic acids, prepare an ion amplicon library, purify the ion amplicon library, sequence the 16S rRNA in the library, and identify the species of microorganisms present in the biological sample with a computer-based genomic analysis using the procedures described in Examples 1-8. PCR primers were selected from those listed in Tables 4 and 5.

Sequence Information: 177,821 sequence reads were obtained for the given sample. The longest 285 sequences were analyzed and compared to all available prokaryotic species.

Results Confidence Profile (355): At the provided quality control cut-off it is estimated that >95% of the sequence reads correctly list the genus, while >95% of the sequence reads correctly list the species.

Figure 5:
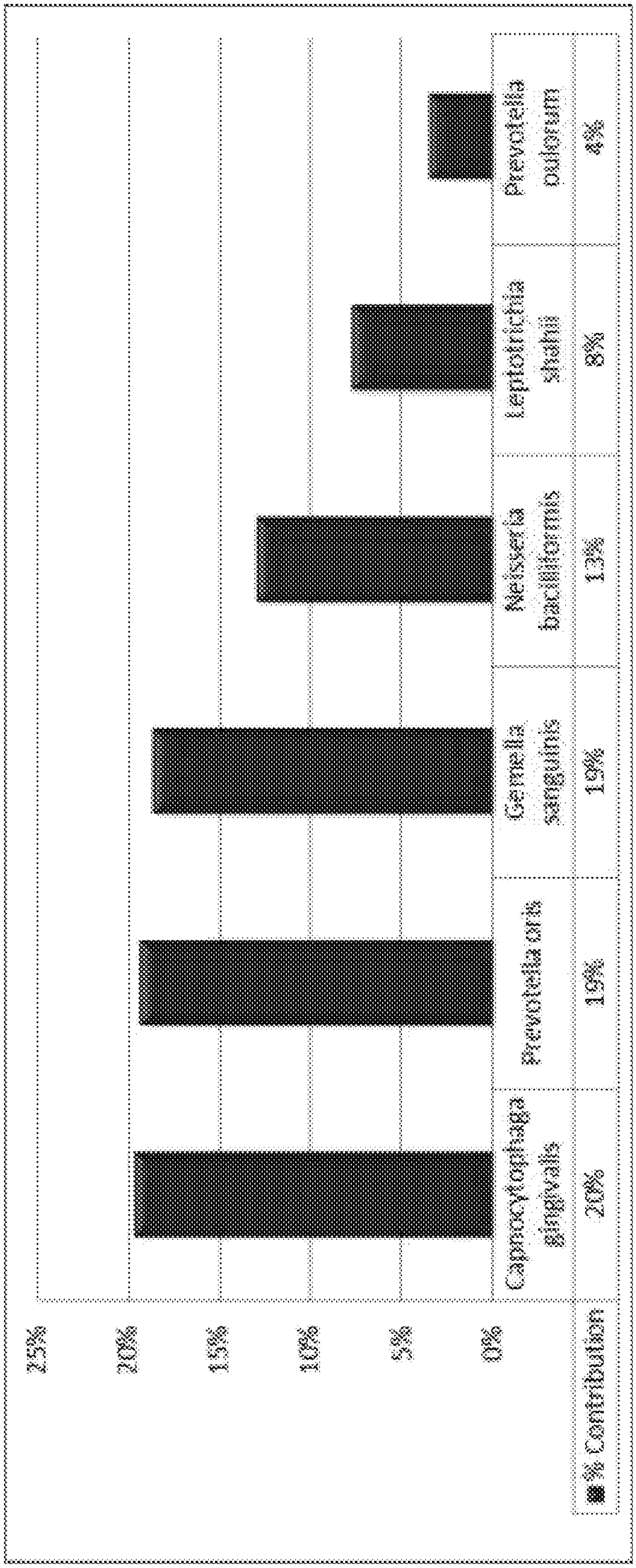
FIG. 5 illustrates results of a computer-based genomics analysis of a patient sample with *Capnocytophaga gingivalis* as the most abundant microorganisms identified.

The identified species are shown in Table 8 and FIG. 5.

TABLE 8

| Species identified by computer-based genomics analysis | | |
|---|---|---|
| Species | Number of Sequences | % |
| *Capnocytophaga gingivalis* | 56 | 20% |
| *Prevotella oris* | 55 | 19% |
| *Gemella sanguinis* | 53 | 19% |
| *Neisseria bacilliformis* | 37 | 13% |
| *Leptotrichia shahii* | 22 | 8% |
| *Prevotella oulorum* | 10 | 4% |
| *Selenomonas infelix* | 8 | 3% |
| *Alysiella filiformis* | 5 | 2% |
| *Streptococcus intermedius* | 5 | 2% |

The antibiotic susceptibility was determined and reported based on the genera identified with the computer-based genomic analysis. The results are shown in Table 9.

TABLE 9

| Antibiotic susceptibilities | | |
|---|---|---|
| Description | Genus Antibiotics | Noted Resistance |
| *Capnocytophaga gingivalis* | Penicillin G, ampicillin, third generation cephalosporins, tetracyclines, clindamycin, and chloromphenicol | Gentamycin and Penicillin G. |
| *Prevotella oris* | Metronidazole, amoxycillin/clavulanate, doxycycline, ureidopenicilins, carbapenems, cephalosporins, clindamycin, and chloramphenicol. | Metronidazole, amoxicillin, amoxycillin/clavulanate, ureidopenicilins, carbapenems, cephalosporins, clindamycin, clarithromycin, chloramphenicol, moxifloxacin, and levofloxacin |
| *Gemella sanguinis* | Penicillin, ampicillin, cephalosporins, tetracyclines, chloramphenicol, lincomycins and tetrasulfathiazole. | Sulfonamides and trimethoprim, and aminoglycosides. |
| *Neisseria bacilliformis* | Cefotaxime and ceftriaxone | Penicillin |
| *Leptotrichia shahii* | Unknown | Unknown |
| *Prevotella oulorum* | Metronidazole, amoxycillin/clavulanate, doxycycline, ureidopenicilins, carbapenems, cephalosporins, clindamycin, and chloramphenicol | Metronidazole, amoxicillin, amoxycillin/clavulanate, ureidopenicilins, carbapenems, cephalosporins, clindamycin, clarithromycin, chloramphenicol, moxifloxacin, and levofloxacin. |

*Capnocytophaga* Species:

Antibiotics: *Capnocytophaga* is susceptible to penicillin G, ampicillin, third generation cephalosporins, tetracyclines, clindamycin, and chloromphenicol.

Resistance: Species has shown resistance to gentamycin and penicillin G in some cases.

REFERENCES

Brenner D J, Hollis D G, Fanning G R, and Weaver R E. 1989. *Capnocytophaga canimorsus* sp. nov. (Formerly CDC Group DF-2), a Cause of Septicemia following Dog Bite, and *C. cynodegmi* sp. nov., a Cause of Localized Wound Infection following Dog Bite. *Journal of Clinical Microbiology* 27 (2): 231-235.

Lion C, Escande F and Burdin J C. 1996. *Capnocytophaga canimorsus* Infections in Human: Review of the Literature and Cases Report. *European Journal of Epidemiology* 12 (5): 521-533.

*Prevotella* Species:

Antibiotics: Antibiotic susceptibility varies among *Prevotella* species. Antibiotics used to treat *Prevotella* infections include: metronidazole, amoxycillin/clavulanate, doxycycline, ureidopenicilins, carbapenems, cephalosporins, clindamycin, and chloramphenicol.

Resistance: Resistance to metronidazole, amoxicillin, amoxycillin/clavulanate, ureidopenicilins, carbapenems, cephalosporins, clindamycin, clarithromycin, chloramphenicol, moxifloxacin, and levofloxacin have been reported.

REFERENCES

Flynn, M. J., Li, G., Slots, J. (1994). *Mitsuokella dentalis* in human periodontitis. Oral Microbiol. Immunol. 9, 248-250.

Mosca A, Miragliotta L, Iodice M A, et al. Antimicrobial profiles of *Prevotella* spp. and *Fusobacterium nucleatum* isolated form periodontal infections in a selected area of southern Italy. Int J of Antimicro Agents December 2007; 30(6):521-4.

Shah, H. N., Collins, D. M. (1990). *Prevotella*, a new genus to include *Bacteroides melaninogenicus* and related species formerly classified in the genus Bacterioides. Int. J. syst. Bacteriol. 40, 205-208.

*Gemella* Species:

Antibiotics: Active antibiotics include: penicillin, ampicillin, cephalosporins, tetracyclines, chloramphenicol, lincomycins and tetrasulfathiazole.

Resistance: Inactive antibiotics include: sulfonamides and trimethoprim, and aminoglycosides.

REFERENCES

Collins, M. D. (2006). The Genus *Gemella*. In M. Dworkin, S. Falkow, E. Rosenberg, K. H. Schleifer & E. Stackebrandt (Eds.), *The Prokaryotes* (3rd ed., pp. 511-518). New York: Springer.

Collins, M. D. (2006). The Genus *Gemella*. In M. Dworkin, S. Falkow, E. Rosenberg, K. H. Schleifer & E. Stackebrandt (Eds.), *The Prokaryotes* (3rd ed., pp. 511-518). New York: Springer.

Buu-Hoi, A., Sapoetra, A., Branger, C., & Acar, J. F. (1982). Antimicrobial susceptibility of *Gemella haemolysans* isolated from patients with subacute endocarditis. *European Journal of Clinical Microbiology,* 1(2), 102-106.

Hamrah, P., Ritterband, D., Seedor, J., & Eiferman, R. A. (2006). Ocular infection secondary to *gemella. Graefe's Archive for Clinical and Experimental Ophthalmology=Albrecht Von Graefes Archiv Fur Klinische Und Experimentelle Ophthalmologic,* 244(7), 891-892.

*Neisseria* Species:

Antibiotics: Active antibiotics for *Neisseria* include third-generation cephalosporin antibiotics such as cefotaxime and ceftriaxone.

Resistance: Some species have been shown to be resistant to the penicillin family of antibiotics.

REFERENCES

Tunkel A R, Hartman B J, Kaplan S L, Kaufman B A, Roos K L, Scheld W M, Whitley R J (November 2004). "Practice guidelines for the management of bacterial meningitis". *Clin Infect Dis* 39 (9): 1267-84. "UK doctors advised gonorrhoea has turned drug resistant BBC News. 10 Oct. 2011.

*Leptotrichia* Species:

Antibiotics: Antibiotic susceptibility for *Leptotrichia* has not been extensively studied.

Resistance: Antibiotic resistance for *Leptotrichia* has not been extensively studied.

REFERENCES

Eribe E R, Paster B J, Caugant D A, Dewhirst F E, Stromberg V K, Lacy G H, Olsen I. Genetic diversity of *Leptotrichia* and description of *Leptotrichia goodfellowii* sp. nov., *Leptotrichia hofstadii* sp. nov., *Leptotrichia shahii* sp. nov. and *Leptotrichia wadei* sp. Nov. Institute of Oral Biology, Dental Faculty, University of Oslo, POB 1052, Blindern, N-0316 Oslo, Norway.

*Prevotella* Species:

Antibiotics: Antibiotic susceptibility varies among *Prevotella* species. Antibiotics used to treat *Prevotella* infections include: metronidazole, amoxycillin/clavulanate, doxycycline, ureidopenicilins, carbapenems, cephalosporins, clindamycin, and chloramphenicol.

Resistance: Resistance to metronidazole, amoxicillin, amoxycillin/clavulanate, ureidopenicilins, carbapenems, cephalosporins, clindamycin, clarithromycin, chloramphenicol, moxifloxacin, and levofloxacin have been reported.

REFERENCES

Flynn, M. J., Li, G., Slots, J. (1994). *Mitsuokella dentalis* in human periodontitis. Oral Microbiol. Immunol. 9, 248-250.

Mosca A, Miragliotta L, Iodice M A, et al. Antimicrobial profiles of *Prevotella* spp. and *Fusobacterium nucleatum* isolated form periodontal infections in a selected area of southern Italy. Int J of Antimicro Agents December 2007; 30(6):521-4.

Shah, H. N., Collins, D. M. (1990). *Prevotella*, a new genus to include *Bacteroides melaninogenicus* and related species formerly classified in the genus Bacterioides. Int. J.

*Selenomonas* Species:

Antibiotics: Active antibiotics include: Azithromycin.

Resistance: Inactive antibiotics: Erythromycin.

REFERENCES

Comparative in-vitro activity of azithromycin, macrolides (erythromycin, clarithromycin and spiramycin) and streptogramin RP 59500 against oral organisms. Williams, J. D., Maskell, J. P., Shain, H., Chrysos, G., Sefton, A. M., Fraser, H. Y., Hardie, J. M. I Antimicrob. Chemother. (1992).

*Alysiella* Species:

Antibiotics: Antibiotic susceptibility for *Alysiella* has not been extensively studied.

Resistance: Antibiotic resistance for *Alysiella* has not been extensively studied.

REFERENCES

Cheng-Hui Xie and Akira Yokota, Transfer of the misnamed [*Alysiella*] sp. IAM 14971 (=ATCC 29468) to the genus *Moraxella* as *Moraxella oblonga* sp. nov., International Journal of Systematic and Evolutionary Microbiology, January 2005 Vol. 55 no. 1 331-334.

*Streptococcus* Species:

Antibiotics: Active antibiotics for *Streptococcus* include: penicillin, amoxicillin, intramuscular benzathine penicillin G, erythromycin, clindamycin, cephalosporins, cephalexin, cefuroxime axetil, and cefdinir.

Resistance: Penicillin has been reported to be ineffective in some cases. B-lactams and macrolides have been reported as an inactive antibiotics.

REFERENCES

Hooton T M. A comparison of azithromycin and penicillin V for the treatment of streptococcal pharyngitis. Am J Med. 1991 September 12; 91(3A):23S-26S.PubMed Cohen R, Reinert P, De La Rocque F, Levy C, Boucherat M, Robert M, Navel M, Brahimi N, Deforche D, Palestro B, Bingen E. Comparison of two dosages of azithromycin for three days versus penicillin V for ten days in acute group A streptococcal tonsillopharyngitis. Pediatr Infect Dis J. 2002 April; 21(4):297-303.

Casey J R, Pichichero M E. Meta-analysis of cephalosporin versus penicillin treatment of group A streptococcal tonsillopharyngitis in children. Pediatrics. 2004 April; 113 (4):866-82.

Scholz H. Streptococcal-A tonsillopharyngitis: a 5-day course of cefuroxime axetil versus a 10-day course of penicillin V. results depending on the children's age. Chemotherapy.

Baltimore R S (February 2010). "Re-evaluation of antibiotic treatment of streptococcal pharyngitis". Curr. Opin. Pediatr. 22 (1): 77-82.

Shulman, S T; Bisno, A L; Clegg, H W; Gerber, M A; Kaplan, E L; Lee, G; Martin, J M; Van Beneden, C (2012 Sep. 9). "Clinical Practice Guideline for the Diagnosis and Management of Group A Streptococcal Pharyngitis: 2012 Update by the Infectious Diseases Society of America.". Clinical infectious diseases: an official publication of the Infectious Diseases Society of America.

Choby B A (March 2009). "Diagnosis and treatment of streptococcal pharyngitis". Am Fam Physician 79 (5): 383-90.

Albrich, W; Monnet, D L; Harbarth, S (2004). "Antibiotic selection pressure and resistance in *Streptococcus pneumoniae* and *Streptococcus pyogenes*". Emerging Infect. Dis. 10 (3): 514-7. PMC 3322805. PMID 15109426.

Example 11. Pan-Bacterial Metagenomics Analysis No. 3

A dental sample from a patient was processed to extract the nucleic acids, prepare an ion amplicon library, purify the ion amplicon library, sequence the 16S rRNA in the library, and identify the species of microorganisms present in the biological sample with a computer-based genomic analysis using the procedures described in Examples 1-8. PCR primers were selected from those listed in Tables 4 and 5.

Sequence Information: 330,413 sequence reads were obtained for the given sample. The longest 268 sequences were analyzed and compared to all available prokaryotic species.

Results Confidence Profile (355): At the provided quality control cut-off it is estimated that >95% of the sequence reads correctly list the genus, while >95% of the sequence reads correctly list the species.

Figure 6:
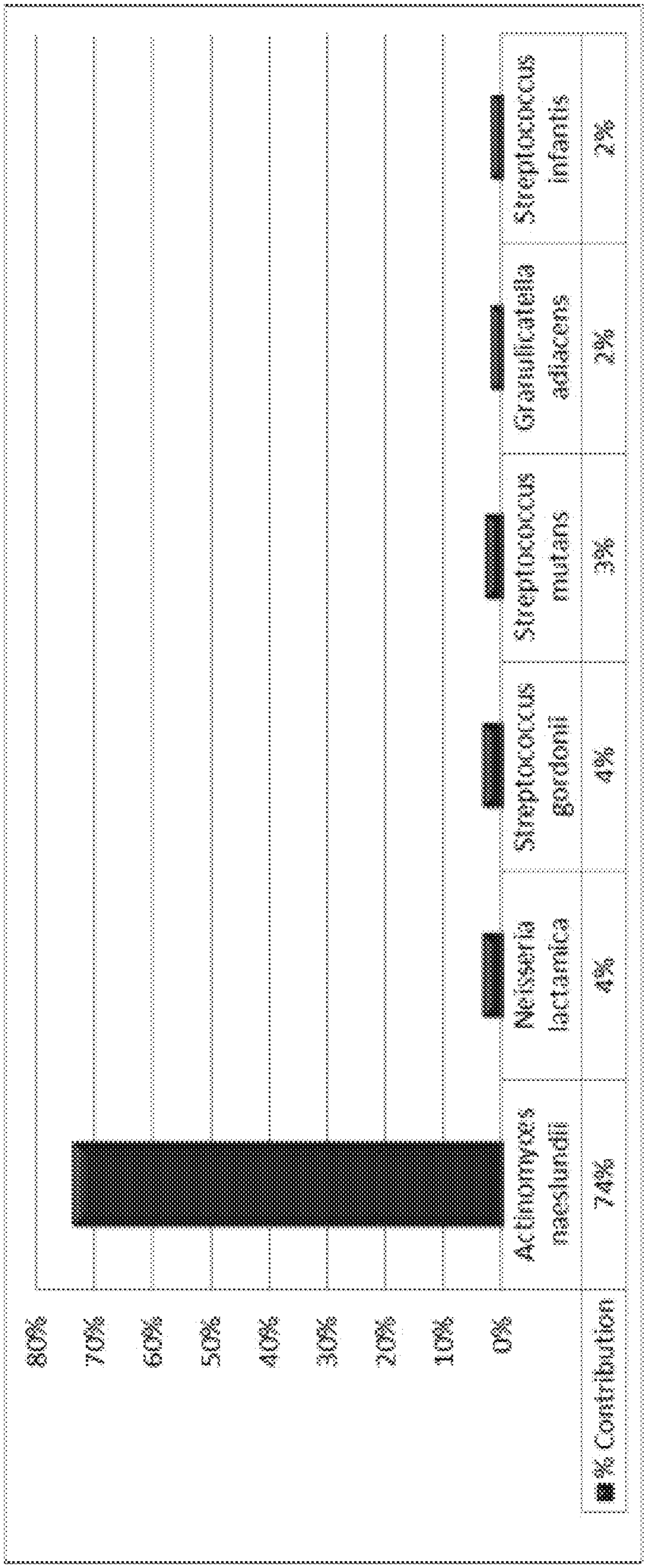
FIG. 6 presents the results of a computer-based genomics analysis of a patient sample with *Actinomyces naeslundii* as the most abundant microorganisms identified.

The identified species are shown in Table 10 and in FIG. 6.

TABLE 10

Species identified by computer-based genomics analysis

| Species | Number of Sequences | % |
|---|---|---|
| *Actinomyces naeslundii* | 198 | 74% |
| *Neisseria lactamica* | 10 | 4% |
| *Streptococcus gordonii* | 10 | 4% |
| *Streptococcus mutans* | 9 | 3% |
| *Granulicatella adiacens* | 6 | 2% |
| *Streptococcus infantis* | 6 | 2% |
| *Streptococcus oralis* | 6 | 2% |

The antibiotic susceptibility was determined and reported based on the genera identified with the computer-based genomic analysis. The results are shown below and in Table 11.

TABLE 11

Antibiotic susceptibilities

| Description | Genus Antibiotics | Noted Resistance |
|---|---|---|
| *Actinomyces naeslundii* | Penicillin, amoxicillin, doxycycline, erythromycin, and clindamycin. Other agents having limited date include: clarithromycin, azithromycin, imipenem, cefotaxime, and ceftiaxone. | Metronidazole, TMP-SMX, ceftazidime, aminoglycosides, oxacillin, and fluoroquinolones. |
| *Neisseria lactamica* | Cefotaxime and ceftriaxone. | Penicillin |
| *Streptococcus gordonii* | Penicillin, amoxicillin, intramuscular benzathine penicillin G, erythromycin, clindamycin, cephalosporins, cephalexin, cefuroxime axetil, and cefdinir. | Penicillin, B-lactams, and macrolides. |
| *Streptococcus mutans* | Refer to *Streptococcus mutans* | Refer to *Streptococcus mutans* |

TABLE 11-continued

| Antibiotic susceptibilities | | |
|---|---|---|
| Description | Genus Antibiotics | Noted Resistance |
| *Granulicatella adiacens* | Penicillin and ceftriaxone, vancomycin, ampicillin, ampicillin-sulbactam, amoxicillin-clavulanate, cefazolin, cefmetazole, or meropenem. | Penicillin, cefotaxime, and azithromycin. Resistance to beta-lactam and macrolide antibiotics has been described. |
| *Streptococcus infantis* | Refer to *Streptococcus mutans* | Refer to *Streptococcus mutans* |

*Actinomyces* Species:

Antibiotics: Active antibiotics for treatment of *Actinomyces* include penicillin, amoxicillin, doxycycline, erythromycin, and clindamycin. Other agents having limited date include: clarithromycin, azithromycin, imipenem, cefotaxime, and ceftriaxone.

Resistance: Antibiotic resistance for *Actinomyces* include metronidazole, TMP-SMX, ceftazidime, aminoglycosides, oxacillin, and fluoroquinolones.

REFERENCES

Smith A J et al: Antimicrobial susceptibility testing of *Actinomyces* species with 12 antimicrobial agents. J Antimicrob Chemother 56:407, 2005.

*Neisseria* Species:

Antibiotics: Active antibiotics for *Neisseria* include third-generation cephalosporin antibiotics such as cefotaxime and ceftriaxone.

Resistance: Some species have been shown to be resistant to the penicillin family of antibiotics.

REFERENCES

Tunkel A R, Hartman B J, Kaplan S L, Kaufman B A, Roos K L, Scheld W M, Whitley R J (November 2004). "Practice guidelines for the management of bacterial meningitis". *Clin Infect Dis* 39 (9): 1267-84. "UK doctors advised gonorrhoea has turned drug resistant BBC News. 10 Oct. 2011.

*Streptococcus* Species:

Antibiotics: Active antibiotics for *Streptococcus* include: penicillin, amoxicillin, intramuscular benzathine penicillin G, erythromycin, clindamycin, cephalosporins, cephalexin, cefuroxime axetil, and cefdinir.

Resistance: Penicillin has been reported to be ineffective in some cases. B-lactams and macrolides have been reported as an inactive antibiotics.

REFERENCES

Hooton T M. A comparison of azithromycin and penicillin V for the treatment of streptococcal pharyngitis. Am J Med. 1991 Sep. 12; 91(3A):23S-26S.PubMed Cohen R, Reinert P, De La Rocque F, Levy C, Boucherat M, Robert M, Navel M, Brahimi N, Deforche D, Palestro B, Bingen E. Comparison of two dosages of azithromycin for three days versus penicillin V for ten days in acute group A streptococcal tonsillopharyngitis. Pediatr Infect Dis J. 2002 April; 21(4):297-303.

Casey J R, Pichichero M E. Meta-analysis of cephalosporin versus penicillin treatment of group A streptococcal tonsillopharyngitis in children. Pediatrics. 2004 April; 113 (4):866-82.

Scholz H. Streptococcal-A tonsillopharyngitis: a 5-day course of cefuroxime axetil versus a 10-day course of penicillin V. results depending on the children's age. Chemotherapy.

Baltimore R S (February 2010). "Re-evaluation of antibiotic treatment of streptococcal pharyngitis". Curr. Opin. Pediatr. 22 (1): 77-82.

Shulman, S T; Bisno, A L; Clegg, H W; Gerber, M A; Kaplan, E L; Lee, G; Martin, J M; Van Beneden, C (2012 Sep. 9). "Clinical Practice Guideline for the Diagnosis and Management of Group A Streptococcal Pharyngitis: 2012 Update by the Infectious Diseases Society of America.". Clinical infectious diseases: an official publication of the Infectious Diseases Society of America.

Choby B A (March 2009). "Diagnosis and treatment of streptococcal pharyngitis". Am F am Physician 79 (5): 383-90.

Albrich, W; Monnet, DL; Harbarth, S (2004). "Antibiotic selection pressure and resistance in *Streptococcus pneumoniae* and *Streptococcus pyogenes*". Emerging Infect. Dis. 10 (3): 514-7. PMC 3322805. PMID 15109426.

*Granulicatella* Species:

Antibiotics: Active antibiotics against *Granulicatella* species include: penicillin and ceftriaxone, vancomycin. ampicillin, ampicillin-sulbactam, amoxicillin-clavulanate, cefazolin, cefmetazole, or meropenem.

Resistance: Inactive antibiotics: penicillin, cefotaxime, and azithromycin. Resistance to beta-lactam and macrolide antibiotics has been described.

REFERENCES

Sheng Kai Tung and Tsung Chain Chang, Molecular Detection of Human Bacterial Pathogens, Edited by Dongyou Liu CRC Press 2011, Pages 249-255.

Levin, Yana D. MD; Petronaci, Carol-Lynn M D. Isolation of *Abiotrophia/Granulicatella* Species from a Brain Abscess in an Adult Patient Without Prior History of Neurosurgical Instrumentation Southern Medical Journal: April 2010—Volume 103—Issue 4—pp 386-387.

Chung-Hsin Liao, Lee-Jene Teng, Po-Ren Hsueh, Yu-Chi Chen, Li-Min Huang, Shan-Chwen Chang, and Shen-Wu Ho. Nutritionally Variant Streptococcal Infections at a University Hospital in Taiwan: Disease Emergence and High Prevalence of β-Lactam and Macrolide Resistance. Oxford Journals, Medicine Clinical Infectious Diseases, Volume 38, Issue 3Pp. 452-455.

Jason C. Gardenier, Tjasa Hranjec, Robert G. Sawyer, and Hugo Bonatti, *Granulicatella adiacens* Bacteremia in an Elderly Trauma Patient. Surgical Infections Volume 12, Number 3, 2011.

Example 12. Analysis of 16S rRNA Variable Regions

The oligonucleotides tested were fusion oligonucleotides as described herein. The oligonucleotides had primer sequences that anneal to the indicated regions on the 16S gene, but they also contain the adapter sequences to make them compatible with sequencing.

An objective of this analysis was to identify important factors for identification of bacteria via 16S sequencing. An equal distribution across four 16S rRNA variable regions (V1/2, V3/2, V3/4, and V5/4) was used to derive this data. The designation "V1/2" indicates that the oligonucleotide allows for sequencing of V1 in the direction of V2, the designation "V3/2" indicates that the oligonucleotide allows for sequencing of V3 in the direction of V2, etc. The fraction of the time that *Ralstonia solanacearum* was correctly identified was plotted based on the length of the obtained reads.

Figure 7A:
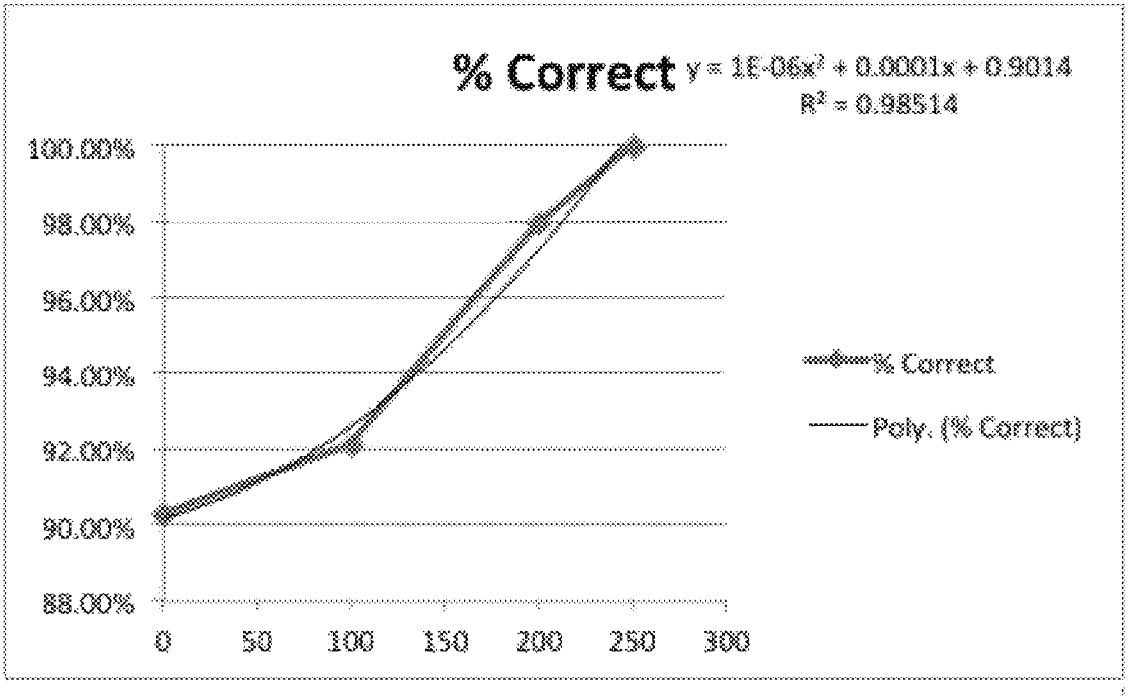
FIG. 7A is a graph illustrating the length of sequencing reads versus the percentage of accurate identifications of the bacterium *Ralstonia solanacearum* in a control sample.

As can be seen in FIG. 7A, the longer reads resulted in more accurate identification of the bacterial species. This analysis was repeated with several other species and similar results were obtained (data not shown). At read lengths of about 250 bp, the accuracy of species identification approached 100% correct identification. Thus, the length of the reads is one of the most important factors to correctly identify a bacterial species. Future selection processes were directly focused on obtaining the longest reads and analyzing the longest reads available.

Figure 7B:
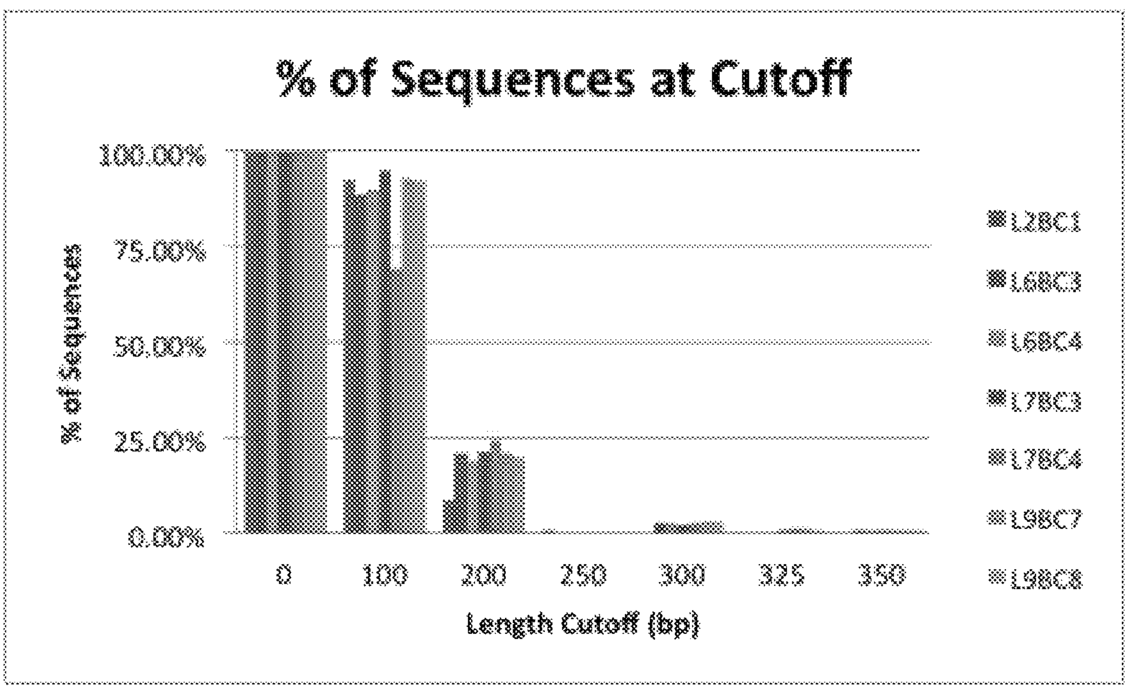
FIG. 7B is a bar graph illustrating that as the cutoff for the length of the sequencing reads increases, the number of available reads at these higher cutoffs decreases.

Also, as expected the number of sequences obtained at longer sizes drop as well. FIG. 7B presents a compilation of cutoffs and the percentage of the sequences in that category from seven different runs.

Having identified the length of the reads as an important factor for accurate identification of bacterial species based on 16S rRNA sequencing, the next objective of the analysis was to determine which 16S variable region resulted in the longest read lengths. As can be seen in Table 12, consistently regions V1/2 and V5/4 produced the longest reads even when the total number of sequences across two different barcodes varied by over double the amount (85574 and 269817, respectively). Ultimately, the extra basepairs translate into longer reads and more accurate identifications.

TABLE 12

Average Read Length Obtained with Oligonucleotides Targeting Specific 16S rRNA Variable Regions

| Bar Code | V1/2 | V3/2 | V3/4 | V5/4 | Total Number of Sequences |
|---|---|---|---|---|---|
| BC005 | 155.23 | 144.86 | 137.70 | 162.94 | 85574 |
| BC006 | 157.70 | 136.69 | 145.72 | 151.81 | 269817 |

These regions were also tested to see if the resulting number of sequences skewed in any particular manner. It was found that for many bacterial species regions V1/2 and V5/4 naturally produced more useable sequences. Table 13 presents an example of one of these analyses.

TABLE 13

Summary of the number of sequences 150 bp or longer obtained from a sample of *Bordatella persussis* with the Oligonucleotides Targeting Specific 16S rRNA Variable Regions

| Library | Bar Code | V1/2 | V3/2 | V3/4 | V5/4 | Unknown | Sum |
|---|---|---|---|---|---|---|---|
| L6 | BC003 | 32566 | 1631 | 74 | 66858 | 1808 | 102937 |
| L6 | BC004 | 46781 | 23247 | 337 | 45510 | 1791 | 117666 |

| Library | Bar Code | V1/2 | V3/2 | V3/4 | V5/4 | Unknown |
|---|---|---|---|---|---|---|
| L6 | BC003 | 31.6% | 1.6% | 0.1% | 65.0% | 1.8% |
| L6 | BC004 | 39.8% | 19.8% | 0.3% | 38.7% | 1.5% |

rRNA variable regions V1/2 and V5/4 were selected for further analysis. Quite a few identification runs were performed using these regions to confirm that they consistently provided longer reads and more accurate genus and species identifications. From this additional experimentation, it was determined that the use of both regions (i.e., V1/2 and V5/4) is preferable because the various bacteria were identified more accurately to the Genus and Species level when both variable regions were sequenced and analyzed (see Table 14). This effect can be seen amongst not only the species tested but with the barcodes selected as well. Using these parameters for bacterial identifications in the samples, generally the genus was accurately identified greater than 95% of the time and the species was accurately identified greater than 30% of the time.

TABLE 14

Identification of bacterial genus and species in control samples using oligonucleotides targeting the V1/2 and V5/4 variable regions of the 16S rRNA. The percentages shown indicate the level of accuracy achieved in correctly identifying the bacterial genus and species in the sample.

| | | Genus Level | | | Species Level | | |
|---|---|---|---|---|---|---|---|
| Barcode | Control ID | % ID | Region 1/2 | Region 5/4 | % ID | Region 1/2 | Region 5/4 |
| 011 | *Mycoplasma pneumoniae* | 98.94% | 94.89% | 5.11% | 98.94% | 94.89% | 5.11% |
| 010 | *Ralstonia solanacearum* | 99.38% | 75.70% | 24.30% | 75.22% | 100.00% | 0.00% |
| 005 | *Ralstonia solanacearum* | 99.60% | 69.17% | 30.83% | 68.82% | 100.00% | 0.00% |
| 005 | *Ralstonia solanacearum* | 99.62% | 77.45% | 22.55% | 77.15% | 100.00% | 0.00% |
| 007 | *Acholeplasma laidlawii* | 99.74% | 71.41% | 28.59% | 97.86% | 72.78% | 27.22% |
| 012 | *Ralstonia solanacearum* | 99.36% | 72.02% | 27.98% | 71.55% | 100.00% | 0.00% |
| 006 | *Mycoplasma arthritidis* | 99.84% | 0.43% | 99.57% | 99.84% | 0.43% | 99.57% |
| 007 | *Mycoplasma fermentans* | 99.86% | 97.05% | 2.95% | 99.86% | 97.05% | 2.95% |
| 012 | *Ralstonia solanacearum* | 99.50% | 45.38% | 54.62% | 45.13% | 99.97% | 0.03% |
| 012 | *Ralstonia solanacearum* | 99.64% | 76.18% | 23.82% | 75.91% | 99.98% | 0.02% |
| 012 | *Ralstonia solanacearum* | 98.90% | 42.44% | 57.56% | 41.93% | 100.00% | 0.00% |
| 012 | *Ralstonia solanacearum* | 99.65% | 68.87% | 31.13% | 68.62% | 100.00% | 0.00% |
| 012 | *Ralstonia solanacearum* | 99.65% | 68.89% | 31.11% | 68.62% | 99.99% | 0.01% |

Figure 8:
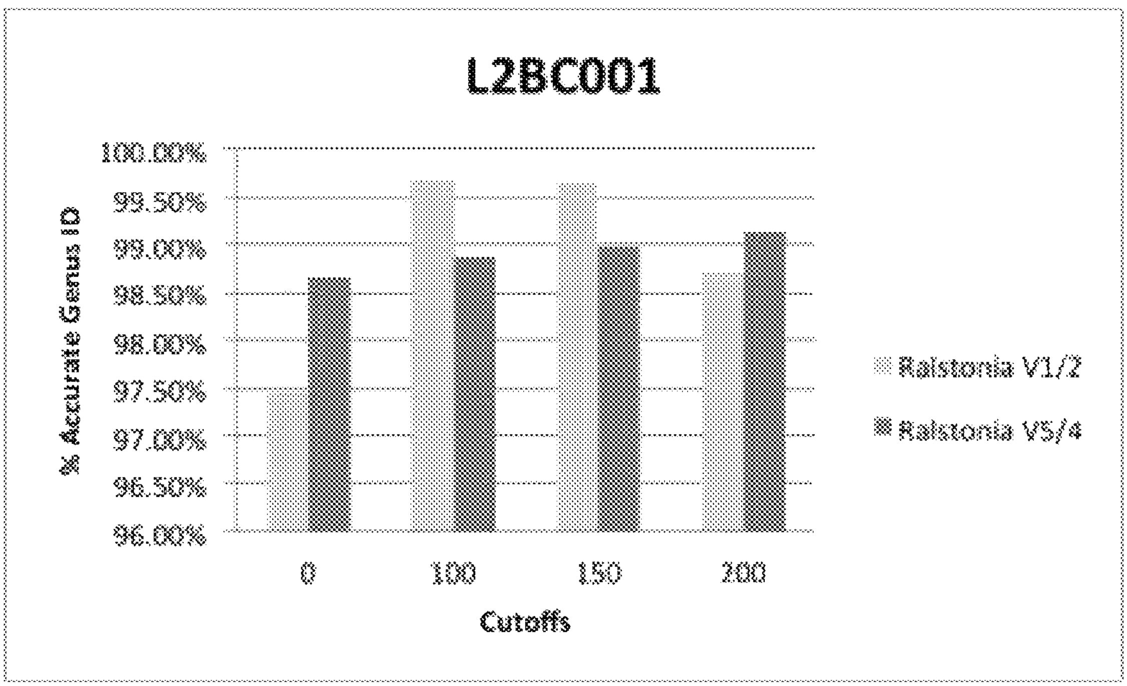
FIG. 8 is a bar graph of the cutoff lengths of sequencing reads using the V1/2 and V5/4 oligonucleotides plotted against the percentage of accurate genus identification with a control sample containing *Ralstonia solanacearum.*
Figure 9A:
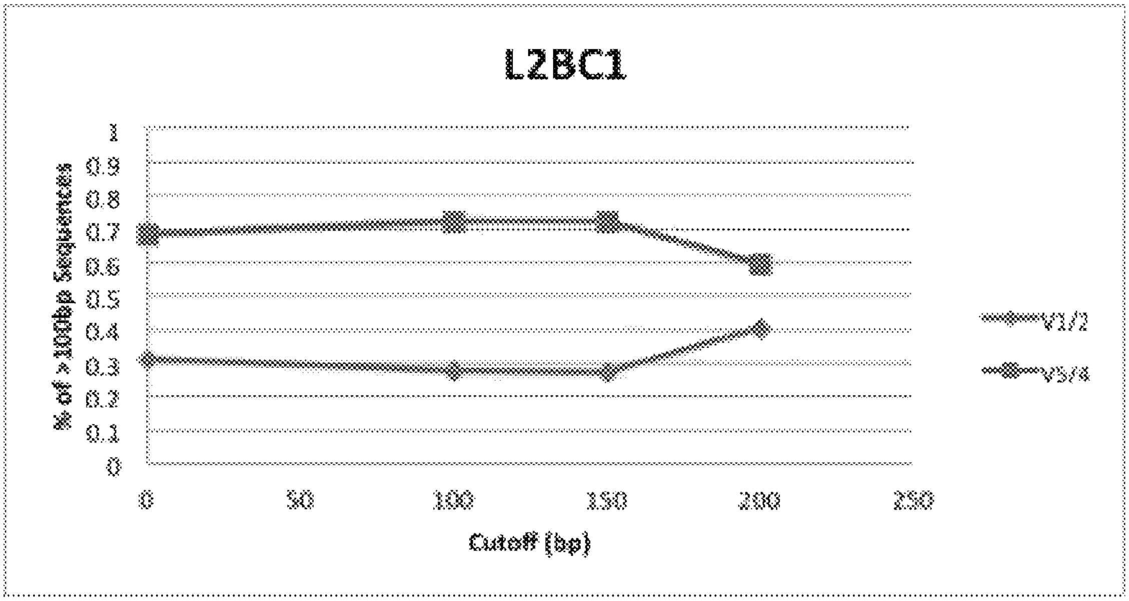
FIGS. 9A, 9B, 10A, and 10B depict line graphs demonstrating that a consistent result is obtained when looking at the two selected 16S rRNA regions of V1/2 and V5/4.
Figure 9B:
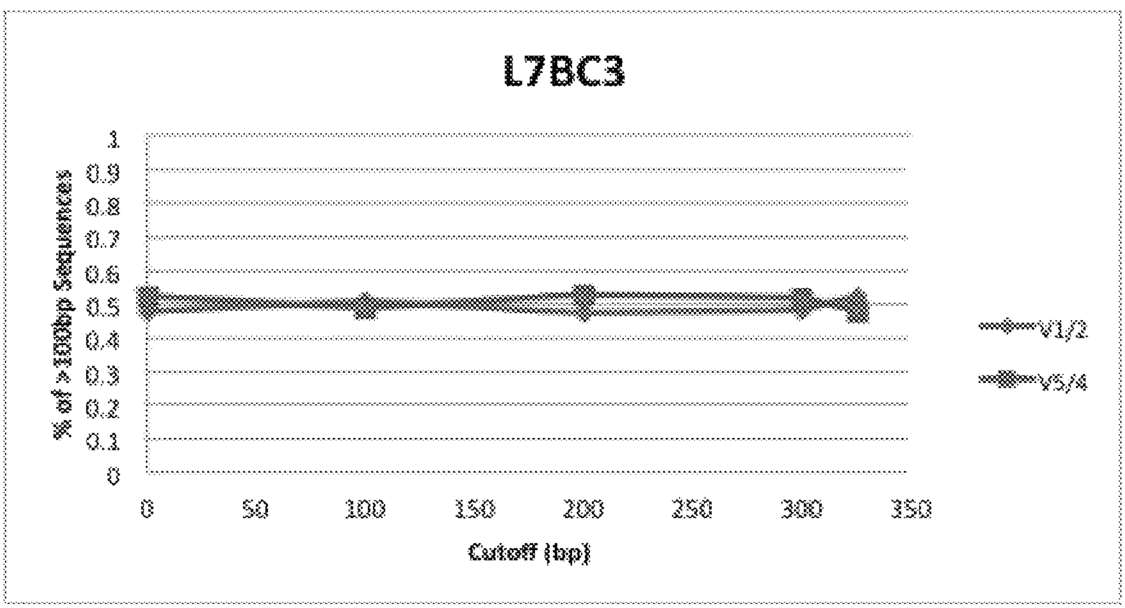
Figure 10A:
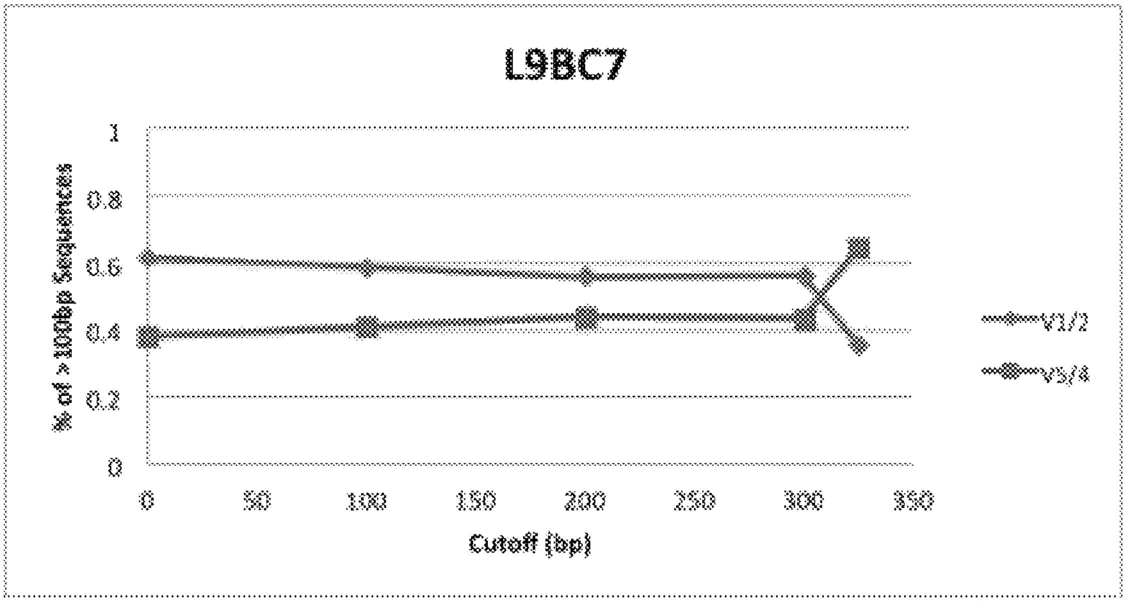
Figure 10B:
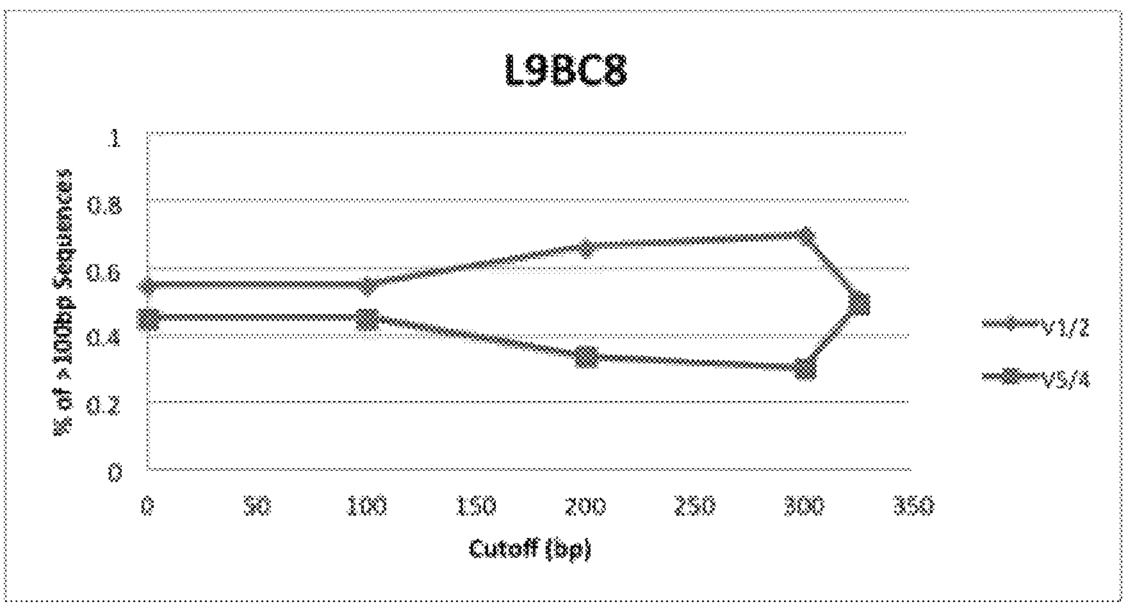

It was also discovered that the number of reads representing any given organism from region V1/2 and V5/4 start to even out given increasingly long read lengths as seen in FIG. 8. Also as the number of >100 bp sequences over various cutoffs were examined it became apparent that there is a consistent result obtained when looking at the two selected regions (see FIGS. 9A, 9B, 10A, and 10B).

Thus, the analysis revealed the surprising result that sequencing the 16S variable regions of V1, V2, V4, and V5 produced the most accurate bacterial identifications. In particular, sequencing from V1 into V2 and from V5 into V4 proved to generate the longest reads and the most accurate identifications of bacterial genera and species.

Example 13. Further Analysis of 16S rRNA Variable Regions

Additional analysis was performed to confirm that 16S rRNA hypervariable regions 1/2 and 5/4 produce superior results over other hypervariable regions. This analysis revealed that regions 1/2 and 5/4 gave total average lengths (before any size filtering) of 156.3 and 171.4 respectively, while regions 3/2 and 3/4 resulted in 120.5 and 140.8, respectively (see Table 15). This length difference was also accompanied by a staggering difference in sequence read number with regions 1/2 and 5/4 resulting in a respective 106151.5 and 90913.7 sequences (on average), while 3/2 and 3/4 resulted in a meager 4942.7 and 433.0 average sequences, respectively (see Table 16).

TABLE 15

Average lengths of sequencing reads using oligonucleotides targeting 16S rRNA variable regions V1/2, V3/2, V3/4, and V5/4.

| | Run/Barcodes | | | | | | |
|---|---|---|---|---|---|---|---|
| Regions | L6BC003 | L6BC004 | L7BC003 | L7BC004 | L9BC007 | L9BC008 | Average |
| 1/2 | 134.2 | 166.7 | 163.7 | 165.5 | 154.6 | 153.0 | 156.3 |
| 3/2 | 133.1 | 108.6 | 119.5 | 118.3 | 118.4 | 125.4 | 120.5 |
| 3/4 | 130.7 | 132.6 | 141.7 | 140.9 | 148.9 | 149.9 | 140.8 |
| 5/4 | 171.3 | 168.3 | 172.8 | 177.6 | 169.2 | 169.0 | 171.4 |

TABLE 16

Average sequence read numbers using oligonucleotides targeting 16S rRNA variable regions V1/2, V3/2, V3/4, and V5/4.

| | Run/Barcodes | | | | | | |
|---|---|---|---|---|---|---|---|
| Regions | L6BC003 | L6BC004 | L7BC003 | L7BC004 | L9BC007 | L9BC008 | Average |
| 1/2 | 32957 | 47370 | 159605 | 163316 | 131133 | 102528 | 106151.5 |
| 3/2 | 1641 | 23420 | 2159 | 1486 | 651 | 299 | 4942.7 |
| 3/4 | 81 | 356 | 569 | 533 | 545 | 514 | 433.0 |
| 5/4 | 68107 | 46325 | 96003 | 210504 | 81332 | 43211 | 90913.7 |

All of this taken together resulted in higher identification rates from regions 1/2 and 5/4 over 3/2 and 3/4. This is shown in looking at the correct identification rates to the genus level with 1/2 identifying 52.2% of the sequences correctly, 5/4 identifying 44.3%, 3/2 only identifying 2.4%, and 3/4 identifying 0.2% (see Tables 17 and 18). This result was not expected based on previous results and could be due to inherent bias or aspects of the sequencing set up.

It was found that using both of V1/2 and V5/4 oligonucleotides for sequencing was preferable because they had slightly different effectiveness identifying various bacterial genera and species. Increasing the detection depth was useful by including both and allowed verification of some of the sequenced organisms by having independent sequence confirmation from two regions (see Table 19).

TABLE 17

Percentage of sequence counts that correctly identified the genus of control samples containing known bacterial microorganisms using oligonucleotides targeting 16S rRNA variable regions V1/2, V3/2, V3/4, and V5/4.

| | Identification | | |
|---|---|---|---|
| Regions | Correct | Incorrect | Region Total |
| 1/2 | 52.2% | 0.2% | 52.4% |
| 3/2 | 2.4% | 0.1% | 2.4% |
| 3/4 | 0.2% | 0.0% | 0.2% |
| 5/4 | 44.3% | 0.6% | 44.9% |

TABLE 18

Total sequence read numbers resulting in correct identification of the bacterial genus of control samples using oligonucleotides targeting 16S rRNA variable regions V1/2, V3/2, V3/4, and V5/4.

| | Identification | | |
|---|---|---|---|
| Regions | Correct | Incorrect | Region Total |
| 1/2 | 634646 | 2263 | 636909 |
| 3/2 | 28836 | 820 | 29656 |
| 3/4 | 2335 | 263 | 2598 |
| 5/4 | 537587 | 7895 | 545482 |
| | | Total | 1214645 |

TABLE 19

Percentages of correctly identified bacterial genera using oligonucleotides targeting 16S rRNA variable regions V1/2, V3/2, V3/4, and V5/4.

| Region 1/2 | Reads | % Identified | Region 1/2 | Reads | % Identified |
|---|---|---|---|---|---|
| *Borrelia* | 13876 | 42.1% | *Bartonella* | 30974 | 65.4% |
| *Bordatella* | 18707 | 56.8% | *Borrelia* | 7689 | 16.2% |
| Off Target | 374 | 1.1% | *Bordatella* | 8414 | 17.8% |
| Total | 32957 | 100.0% | Off Target | 293 | 0.6% |
| | | | Total | 47370 | 100.0% |
| Region 1/2 | Reads | % Identified | Region 1/2 | Reads | % Identified |
| Myoplasma | 67152 | 42.1% | Myoplasma | 74691 | 45.7% |
| *Bordatella* | 92142 | 57.7% | *Bordatella* | 88239 | 54.0% |
| Off Target | 311 | 0.2% | Off Target | 386 | 0.2% |
| Total | 159605 | 100.0% | Total | 163316 | 100.0% |
| Region 1/2 | Reads | % Identified | Region 1/2 | Reads | % Identified |
| *Borrelia* | 41133 | 31.4% | *Borrelia* | 36449 | 35.6% |
| *Bordatella* | 89428 | 68.2% | *Bordatella* | 65752 | 64.1% |
| Off Target | 572 | 0.4% | Off Target | 327 | 0.3% |
| Total | 131133 | 100.0% | Total | 102528 | 100.0% |
| Region 3/2 | Reads | % Identified | Region 3/2 | Reads | % Identified |
| *Borrelia* | 543 | 33.1% | *Bartonella* | 22513 | 96.1% |
| *Bordatella* | 970 | 59.1% | *Borrelia* | 0 | 0.0% |
| Off Target | 128 | 7.8% | *Bordatella* | 604 | 2.6% |
| Total | 1641 | 100.0% | Off Target | 303 | 1.3% |
| | | | Total | 23420 | 100.0% |

TABLE 19-continued

Percentages of correctly identified bacterial genera using oligonucleotides targeting 16S rRNA variable regions V1/2, V3/2, V3/4, and V5/4.

| Region 3/2 | Reads | % Identified | Region 3/2 | Reads | % Identified |
|---|---|---|---|---|---|
| Myoplasma | 345 | 16.0% | Myoplasma | 203 | 13.7% |
| *Bordatella* | 1682 | 77.9% | *Bordatella* | 1183 | 79.6% |
| Off Target | 132 | 6.1% | Off Target | 100 | 6.7% |
| Total | 2159 | 100.0% | Total | 1486 | 100.0% |
| **Region 3/2** | **Reads** | **% Identified** | **Region 3/2** | **Reads** | **% Identified** |
| *Borrelia* | 146 | 22.4% | *Borrelia* | 67 | 22.4% |
| *Bordatella* | 381 | 58.5% | *Bordatella* | 199 | 66.6% |
| Off Target | 124 | 19.0% | Off Target | 33 | 11.0% |
| Total | 651 | 100.0% | Total | 299 | 100.0% |
| **Region 3/4** | **Reads** | **% Identified** | **Region 3/4** | **Reads** | **% Identified** |
| *Borrelia* | 30 | 37.0% | *Bartonella* | 241 | 67.7% |
| *Bordatelia* | 37 | 45.7% | *Borrelia* | 0 | 0.0% |
| Off Target | 14 | 17.3% | *Bordatella* | 42 | 11.8% |
| Total | 81 | 100.0% | Off Target | 73 | 20.5% |
| | | | Total | 356 | 100.0% |
| **Region 3/4** | **Reads** | **% Identified** | **Region 3/4** | **Reads** | **% Identified** |
| Myoplasma | 62 | 10.9% | Mycoplasma | 46 | 8.6% |
| *Bordatella* | 470 | 82.6% | *Bordatella* | 453 | 85.0% |
| Off Target | 37 | 6.5% | Off Target | 34 | 6.4% |
| Total | 569 | 100.0% | Total | 533 | 100.0% |
| **Region 3/4** | **Reads** | **% Identified** | **Region 3/4** | **Reads** | **% Identified** |
| *Borrelia* | 104 | 19.1% | *Borrelia* | 72 | 14.0% |
| *Bordatella* | 382 | 70.1% | *Bordatella* | 396 | 77.0% |
| Off Target | 59 | 10.8% | Off Target | 46 | 8.9% |
| Total | 545 | 100.0% | Total | 514 | 100.0% |
| **Region 5/4** | **Reads** | **% Identified** | **Region 5/4** | **Reads** | **% Identified** |
| *Borrelia* | 44599 | 65.5% | *Bartonella* | 32806 | 70.8% |
| *Bordatella* | 22984 | 33.7% | *Borrelia* | 68 | 0.1% |
| Off Target | 524 | 0.8% | *Bordatella* | 12588 | 27.2% |
| Total | 68107 | 100.0% | Off Target | 863 | 1.9% |
| | | | Total | 46325 | 100.0% |
| **Region 5/4** | **Reads** | **% Identified** | **Region 5/4** | **Reads** | **% Identified** |
| Myoplasma | 18177 | 18.9% | Myoplasma | 49079 | 23.3% |
| *Bordatella* | 76160 | 79.3% | *Bordatella* | 158274 | 75.2% |
| Off Target | 1666 | 1.7% | Off Target | 3151 | 1.5% |
| Total | 96003 | 100.0% | Total | 210504 | 100.0% |
| **Region 5/4** | **Reads** | **% Identified** | **Region 5/4** | **Reads** | **% Identified** |
| *Borrelia* | 36411 | 44.8% | *Borrelia* | 17302 | 40.0% |
| *Bordatella* | 43794 | 53.8% | *Bordatella* | 25345 | 58.7% |
| Off Target | 1127 | 1.4% | Off Target | 564 | 1.3% |
| Total | 81332 | 100.0% | Total | 43211 | 100.0% |

Example 14. Pan-Bacterial Metagenomics Analysis No. 4

A blood sample from a patient was processed to extract the nucleic acids, prepare an ion amplicon library, purify the ion amplicon library, sequence the 16S rRNA in the library, and identify the species of microorganisms present in the biological sample with a computer-based genomic analysis using the procedures described in Examples 1-8. PCR primers were selected from those listed in Tables 4 and 5.

Sequence Information: 703297 sequence reads were obtained for DNA extracted from a blood sample. The longest 332,906 sequences were analyzed and compared to all available prokaryotic species.

Results Confidence Profile: At the provided quality control cut-off it is estimated that >95% of the sequence reads correctly list the genus, while >30% of the sequence reads correctly list the species.

Figure 11:
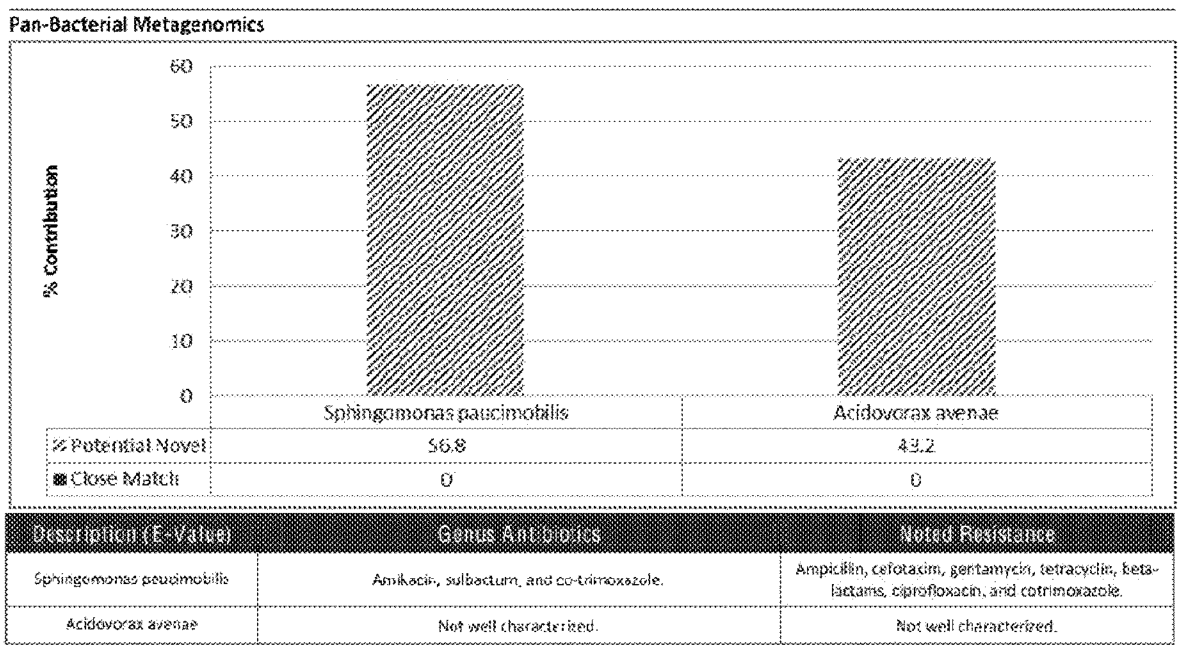
FIG. 11 presents the results of a computer-based genomics analysis of a patient sample with *Sphingomonas paucimobilis* as the most abundant microorganisms identified.

The identified species are shown in FIG. 11.

Figure 18:
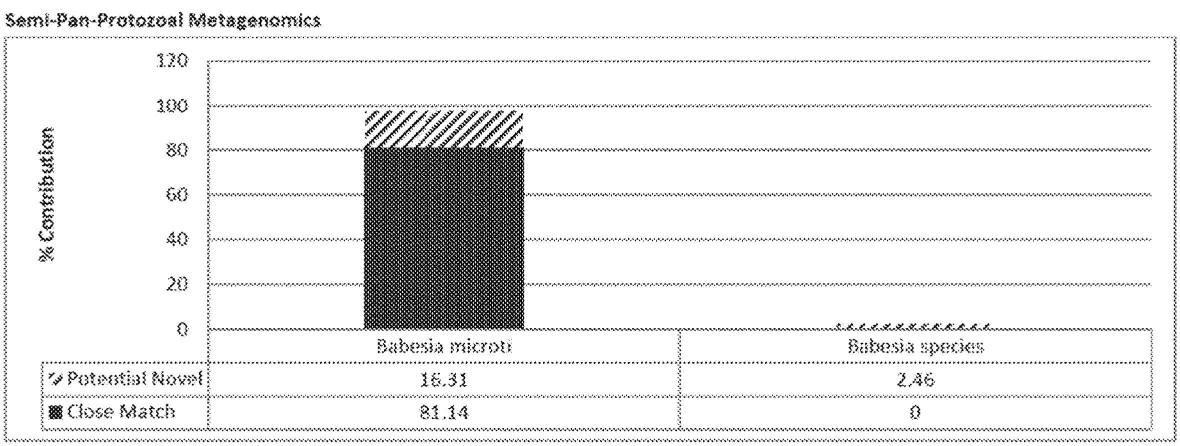
FIGS. 18-21 illustrate results of a computer-based genomics analysis is accordance with further exemplary embodiments of the disclosure.
Figure 19:
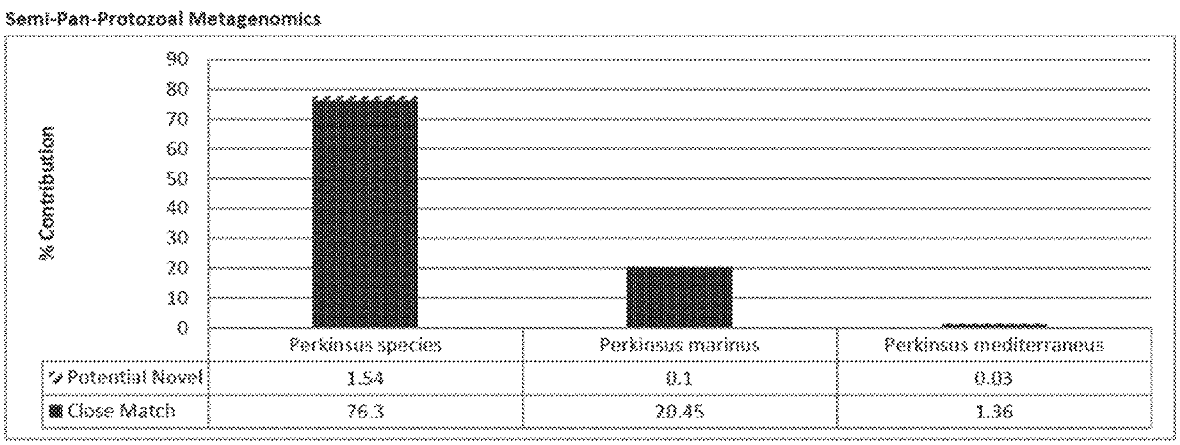
Figure 20:
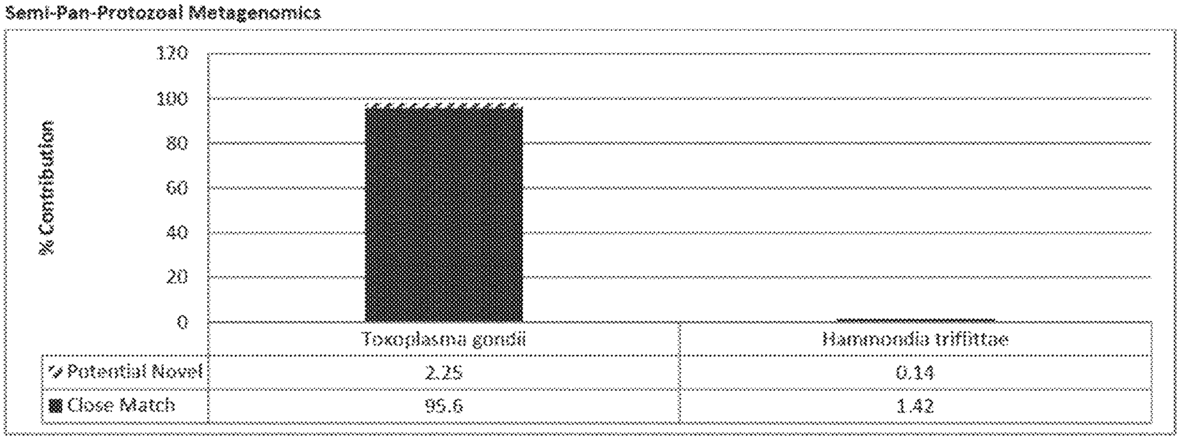
Figure 21:
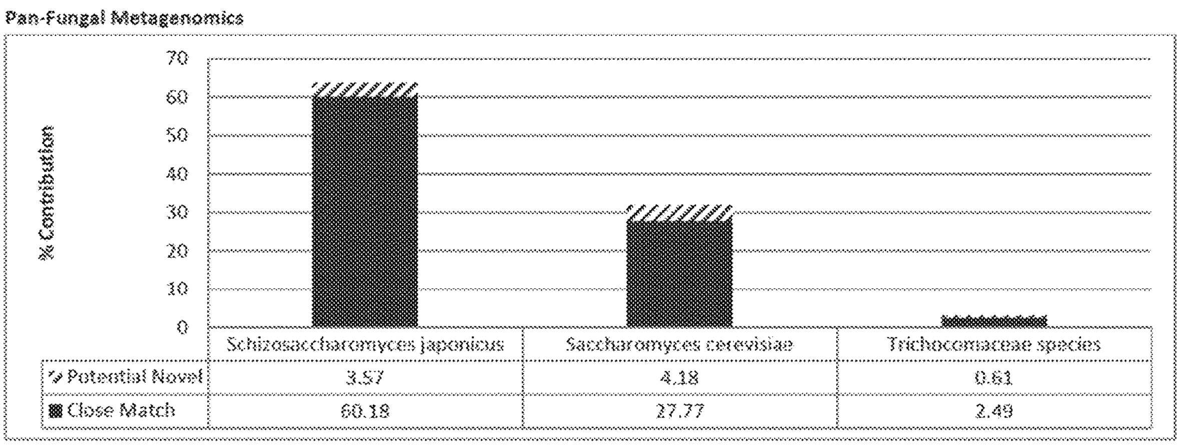

Further examples include using the systems, methods and/or kits as described herein to characterize other microorganisms, such as protozoa, viruses, and fungi. FIGS. 18-20 illustrate reports generated from a method that detected protozoa. A PCR procedure suitable for amplification of protozoa is disclosed in application Ser. No. 13/834,441, entitled SEMI-PAN-PROTOZOAL BY QUANTITATIVE PCR, filed on Mar. 15, 2013, the contents of which are hereby incorporated herein by reference, to the extend such contents do not conflict with the present disclosure. FIG. 21 illustrates a report generated from a method that detected fungi. Further, by way of specific example, Adenovirus type 2 was detected using a method as described herein.

Additional Nonlimiting Examples of the Disclosure Include:

1. A method of characterizing one or more microorganisms, the method comprising the steps of:
   preparing an amplicon library with a polymerase chain reaction (PCR) of nucleic acids;
   sequencing a characteristic gene sequence in the amplicon library to obtain a gene sequence; and
   characterizing the one or more microorganisms based on the gene sequence using a computer-based genomic analysis of the gene sequence.
2. The method of example 1, wherein the amplicon library comprises an ion amplicon library.
3. The method of any of examples 1-2, further comprising a step of extracting nucleic acids from a biological sample of a subject.
4. The method of any of examples 1-3, further comprising a step of purifying the amplicon library from the PCR reaction.
5. The method of any of examples 1-4, wherein the one or more microorganisms comprise bacteria and the characteristic gene comprises 16S ribosomal RNA (16S rRNA).
6. The method of any of examples 1-5, wherein the one or more microorganisms comprise protozoa.
7. The method of any of examples 1-6, wherein the one or more microorganisms comprise fungi.
8. The method of any of examples 1-7, wherein the one or more microorganisms comprise viruses.
9. The method of any of examples 1-8, wherein the step of sequencing comprises using an ion semiconductor sequencing platform or a platform based on stepwise addition of reversible terminator nucleotides.
10. The method of any of examples 1-9, further comprising a step of identifying the one or more microorganisms using a computer-based genomic analysis of the gene sequence.
11. The method of any of examples 1-10, further comprising a step of determining a nearest characterized microorganism.
12. The method of any of examples 1-11, wherein the PCR reaction uses at least one forward primer.
13. The method of example 12, wherein the forward primer comprises a target sequence that comprises a sequence from the characteristic gene.
14. The method of example 13, wherein the target sequence comprises a sequence from a 16S rRNA gene selected from a hypervariable region selected from the group consisting of V1, V2, V4, and V5.
15. The method of any of examples 13-14, wherein the target sequence comprises a sequence from the 16S rRNA gene selected from the group consisting of (i) a sequence beginning in V1 and extending towards V2, (ii) a sequence beginning in V5 and extending towards V4, (iii) a sequence beginning in V2 and extending towards V1, and (iv) a sequence beginning in V4 and extending towards V5.
16. The method of any of examples 13-15, wherein the target sequence from the 16S rRNA comprises SEQ ID NO: 18 or SEQ ID NO: 19.
17. The example of any of examples 1-16, wherein the PCR reaction uses at least a first forward primer and a second forward primer, each comprising a barcode, a barcode adapter, and a target sequence;
   wherein a target sequence of the first forward primer comprises a sequence from a 16S rRNA gene beginning in V1 and extending towards V2 and a target sequence of the second forward primer comprises a sequence beginning in V5 and extending towards V4.
18. The method of any of examples 13-17, wherein the target sequence comprises a sequence from a 16S rRNA gene selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.
19. The method of any of examples 12-18, wherein the forward primer comprises a sequence from a 16S rRNA gene selected from the group consisting of SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, and SEQ ID NO: 50.
20. The method of any of examples 1-19, wherein the PCR reaction uses a reverse primer comprising SEQ ID NO: 33.
21. The method of any of examples 12-20, wherein the forward primer comprises a sequence from a 16S rRNA gene selected from the group consisting of SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, and SEQ ID NO: 66.
22. The method of any of examples 1-21, wherein the PCR reaction uses a reverse primer comprising SEQ ID NO: 34.
23. The method of any of examples 3-22, wherein the biological sample comprises material selected from a urine sample, a blood sample, a joint sample, a dental sample, a bronchioalveolar lavage, a nasal swab, cerebrospinal fluid, synovial fluid, brain tissue, cardiac tissue, bone, skin, and a lymph node tissue.

24. The method of any of examples 3-23, wherein the biological sample comprises a dental sample and the one or more microorganisms comprises a microorganism from a genus selected from the group consisting of *Bacteroides, Tannerella, Prevotella, Peptostreptococcus, Streptococcus, Staphylococcus, Porphyromonas, Fusobacterium, Clostridium, Treponema, Atopobium, Cryptobacterium, Eubacterium, Mogibacterium, Filifactor, Dialister, Centipeda, Selenomonas, Granulicatella*, and *Kingella.*
25. The method of any of examples 3-24, wherein the biological sample comprises a joint sample and the one or more microorganisms comprises a microorganism from a genus selected from the group consisting of *Staphylococcus, Streptococcus, Kingella, Aeromonas, Mycobacterium, Actinomyces, Fusobacterium, Salmonella, Haemophilus, Borrelia, Neisseria, Escherichia, Brucella, Pseudomonas, Mycoplasma, Salmonella, Propionibacterium, Acinetobacter, Treponema*, and *Erysipelothrix.*
26. The method of any of examples 3-25, wherein the biological sample comprises a blood sample and the one or more microorganisms comprises a microorganism from a genus selected from the group consisting of *Capnocytophaga, Rickettsia, Staphylococcus, Streptococcus, Neisseria, Mycobacterium, Klebsiella, Haemophilus, Fusobacterium, Chlamydia, Enterococcus, Escherichia, Enterobacter, Proteus, Legionella, Pseudomonas, Clostridium, Listeria, Serratia*, and *Salmonella.*
27. The method of any of examples 1-26, wherein the one or more microorganisms comprises at least one nonculturable pathogen.
28. The method of any of examples 1-27, further comprising a step of generating a report with a one or more of a genera and species of the one or more microorganisms.
29. The method of example 28, wherein the report includes a relative measure of the one or more of genera and species contribution and diversity in the biological sample and antimicrobial resistance and susceptibility information for each genus and/or species.
30. The method of any of examples 1-29, further comprising treating the subject with a treatment identified in the report.
31. The method of any of examples 1-30, wherein the computer-based genomic analysis comprises application of a procedural algorithm to sequencing data.
32. The method of example 31, wherein the procedural algorithm excludes sequences that are present less than five times or constitute less than one percent of the sequencing data.
33. A kit for characterizing at least one microorganism, the kit comprising:

a) at least one forward primer comprising an adapter sequence and a priming sequence, for a target sequence, wherein the target sequence comprises a sequence from a characteristic gene sequence; and b) at least one reverse primer.

34. The kit of example 33, wherein the target sequence comprises a sequence from a hypervariable region from a 16S rRNA gene selected from the group consisting of V1, V2, V4, and V5.
35. The kit of any of examples 33-34, wherein the forward primer comprises a barcode and a barcode adapter.
36. The kit of any of examples 33-35, wherein the target sequence comprises a 16S rRNA gene sequence selected from the group consisting of (i) a sequence beginning in V1 and extending towards V2, (ii) a sequence beginning in V5 and extending towards V4, (iii) a sequence beginning in V2 and extending towards V1, and (iv) a sequence beginning in V4 and extending towards V5.
37. The kit of any of examples 33-36, wherein the at least one forward primer comprises a sequence selected from the group consisting of SEQ ID NO: 18 and SEQ ID NO: 19.
38. The kit of any of examples 33-37, wherein the at least one forward primer comprises a first forward primer and a second forward primer, each comprising a barcode, a barcode adapter, and a target sequence;

wherein the target sequence of the first forward primer comprises a sequence beginning in V1 and extending towards V2 and the target sequence of the second forward primer comprises a sequence beginning in V5 and extending towards V4.

39. The kit of any of examples 33-38, wherein the first forward primer comprises SEQ ID NO: 18 and a second forward primer comprises SEQ ID NO: 19.
40. The kit of any of examples 33-39, wherein the at least one reverse primer comprises a sequence selected from the group consisting of SEQ ID NO: 33 and SEQ ID NO: 34.
41. The kit of any of examples 33-40, wherein the target sequence is selected from the group consisting of SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.
42. The kit of any of examples 33-38, wherein the target sequence is about 10 nucleotides in length to about 30 nucleotides in length.
43. A method of characterizing one or more microorganisms in a biological sample, the method comprising the steps of:

providing at least one forward primer comprising an adapter sequence and a primer sequence for a target sequence, wherein the target sequence comprises a sequence from a hypervariable region from a 16S rRNA gene selected from the group consisting of V1, V2, V4, and V5;

providing at least one reverse primer;

providing a biological sample comprising nucleic acids;

preparing an amplicon library with a polymerase chain reaction (PCR) of the nucleic acids;

purifying the amplicon library from the PCR reaction;

sequencing a 16S ribosomal RNA (16S rRNA) gene in the ion amplicon library to obtain a gene sequence; and characterizing the one or more microorganisms based on the gene sequence using a computer-based genomic analysis of the 16S rRNA gene sequence.

Although any methods and materials, similar or equivalent to those described herein, can be used in the practice or testing of the present invention, the preferred methods and materials are described herein. All publications, patents, and patent publications cited are incorporated by reference herein in their entirety for all purposes, to the extent such references do not conflict with the present disclosure.

It is understood that the disclosed invention is not limited to the particular methodology, protocols and materials described as these can vary. It is also understood that the terminology used herein is for the purposes of describing particular embodiments only and is not intended to limit the scope of the present invention that will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying a species of one or more microorganisms in a biological sample, comprising:

providing a first set of primers for amplifying a first target sequence comprising hypervariable regions V1 and V2 but not V3 of a 16S rRNA gene;

providing a second set of primers for amplifying a second target sequence comprising hypervariable regions V4 and V5 but not V3 of the 16S rRNA gene, wherein the second set of primers comprises at least one forward primer and at least one reverse primer, and wherein the at least one forward primer comprises a sequence from the 16S rRNA gene selected from the group consisting of SEQ ID NO: 35, SEQ ID NO: 36, SEQ ID NO: 37, SEQ ID NO: 38, SEQ ID NO:39, SEQ ID NO:40, SEQ ID NO 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66;

extracting nucleic acids from the biological sample, the biological sample comprising the one or more microorganisms;

amplifying the first and second target sequences from the extracted nucleic acids using the first and second set of primers;

sequencing from 5' to 3' V1 and V2 of the first target sequence and sequencing from 5' to 3' V5 and V4 of the second target sequence to obtain one or more sequence reads of the first and second target sequences, the sequencing being based on detection of hydrogen ions released during amplification of the first and second target sequences;

defining a first target sequence subset, wherein the first target sequence subset is part or all of the first target sequence;

defining a second target sequence subset, wherein the second target sequence subset is part or all of the second target sequence;

performing, by a computer, a set of alignments of the first and second target sequences by comparing each of the first target sequence subset and the second target sequence subset to a set of microbial nucleic acid sequences stored in a database;

determining, by the computer, one or more sequence portions from among the first and second target sequence subsets that have at least one alignment match to the set of microbial nucleic acid sequences stored in the database;

identifying, by the computer, the species and/or genus of the one or more microorganisms in the biological sample based on the at least one alignment match of the first and second target sequences to the set of microbial nucleic acid sequences stored in the database; and correlating, by the computer, one or more antibiotic treatments to the species and/or genus of the one or more microorganisms in the biological sample, wherein the species and/or genus of the one or more microorganisms is identified by the computer.

2. The method of claim 1, wherein at least one first primer in the first set of primers and at least one second primer in the second set of primers comprise a barcode used to identify the one or more microorganisms.

3. The method of claim 1, wherein the one or more microorganisms comprise a pathogenic community of microorganisms.

4. The method of claim 1, wherein the biological sample comprises a urine sample, a blood sample, a joint sample, a bronchioalveolar lavage sample, a nasal swab sample, cerebrospinal fluid, synovial fluid, brain tissue, cardiac tissue, bone, skin, or a lymph node tissue.

5. The method of claim 1, wherein the one or more microorganisms comprise at least one nonculturable pathogenic bacterium.

6. The method of claim 1, further comprising generating a report with at least one genus or at least one species of the one or more microorganisms, and wherein the report comprises the one or more antibiotic treatments corresponding to the species and/or genus of the one or more microorganisms in the biological sample.

7. The method of claim 1, wherein the one or more microorganisms is identified by:

comparing, by the computer, each of one or more subsets of the first and second target sequences having the at least one alignment match and having at least a predetermined number of base pairs, to the set of microbial nucleic acid sequences stored in the database; and determining, by the computer, each of the one or more subsets of the first and second target sequences having the at least one alignment match to the set of microbial nucleic acid sequences stored in the database based on at least one alignment match criterion, wherein the one or more subsets of the first and second target sequences meeting the at least one alignment match criterion identify the one or more microorganisms.

8. The method of claim 7, wherein determining, by the computer, each of the first and second target sequences that have an alignment match to the set of microbial nucleic acid sequences stored in the database comprises determining whether a confidence of the alignment match is within a confidence percentage.

9. The method of claim 8, wherein the confidence percentage is 95%.

10. The method of claim 8, wherein the predetermined number of base pairs is 100 base pairs.

11. The method of claim 8, wherein the at least one criterion comprises a 95% alignment match.

12. The method of claim 1, wherein performing, by the computer, the set of alignments of the first and second target sequences by comparing the first target sequence subset and the second target sequence subset to the set of microbial nucleic acid sequences stored in the database comprises employing a comparison window having between 10 and 65 base pairs.

13. The method of claim 1, wherein determining, by the computer, the one or more sequence portions from among the first portions of the first and second target sequences that have the at least one alignment match to the set of microbial nucleic acid sequences stored in the database comprises selecting first and second target sequences having between 50 and 150 base pairs.

14. The method of claim 1, wherein the database is a first database, the set of microbial nucleic acid sequences is a first set of microbial nucleic acid sequences, and wherein the method further comprises:

defining a third target sequence subset, wherein the third target sequence subset is part of the first target sequence;

defining a fourth target sequence subset, wherein the fourth target sequence subset is part of the second target sequence;

performing, by the computer, one or more alignments of the first target sequence and the second target sequence by comparing the third target sequence subset and the fourth target sequence subset to a second set of microbial nucleic acid sequences stored in the second database;

determining, by the computer, one or more alignment matches to the second set of microbial nucleic acid sequences stored in the second database; and identifying, by the computer, the species and/or genus of the one or more microorganisms in the biological sample based on the one or more one alignment matches of the third and fourth target sequence subsets to the second set of microbial nucleic acid sequences stored in the second database.

15. The method of claim 14, wherein identifying, by the computer, the species and/or the genus of the one or more microorganisms in the biological sample comprises:

determining, by the computer, a first certainty of a first alignment match of the first target sequence subset and the second target sequence subset to sequences to the first set of microbial nucleic acid sequences stored in the first database;

determining, by the computer, a second certainty of a second alignment match of the third target sequence subset and the fourth target sequence subset to the second set of microbial nucleic acid sequences stored in the second database; and comparing, by the computer, the first certainty to the second certainty to determine a closeness of match either to the first database or to the second database.

16. The method of claim 15, further comprising:

determining a first number of alignment matches having at least a 90% or greater certainty of one or more alignment matches between:

the first, second, third and fourth target sequence subsets and the first set of microbial nucleic acid sequences in the first database, wherein the closeness of match to the first database is greater than the closeness of match to the second database; or the first, second, third and fourth target sequence subsets and the second set of microbial nucleic acid sequences in the second database, wherein the closeness of match to the second database is greater than the closeness of match to the first database, and wherein any of the first, second, third and fourth target sequence subsets having at least a 90% or greater certainty of an alignment match correspond to a characterized microorganism.

17. The method of claim 16, further comprising determining a second number of alignment matches having less than the 90% or greater certainty of the alignment match between:

the first, second, third and fourth target sequence subsets and the first set of microbial nucleic acid sequences in the first database, wherein the closeness of match to the first database is greater than the closeness of match to the second database; or the first, second, third and fourth target sequence subsets and the second set of microbial nucleic acid sequences in the second database, wherein the closeness of match to the second database is greater than the closeness of match to the first database, wherein the second number of alignment matches having less than the 90% or greater certainty do not correspond to the characterized microorganism.

* * * * *